(12) United States Patent
Watanabe et al.

(10) Patent No.: US 10,340,471 B2
(45) Date of Patent: Jul. 2, 2019

(54) ORGANIC ELECTROLUMINESCENT ELEMENT AND NOVEL IRIDIUM COMPLEX

(71) Applicant: UDC Ireland Limited, Dublin (IE)

(72) Inventors: Kousuke Watanabe, Kanagawa (JP); Yuichirou Itai, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 1034 days.

(21) Appl. No.: 14/240,109

(22) PCT Filed: Sep. 25, 2012

(86) PCT No.: PCT/JP2012/074554
§ 371 (c)(1),
(2) Date: May 13, 2014

(87) PCT Pub. No.: WO2013/047517
PCT Pub. Date: Apr. 4, 2013

(65) Prior Publication Data
US 2014/0252333 A1 Sep. 11, 2014

(30) Foreign Application Priority Data
Sep. 30, 2011 (JP) .................. 2011-218507

(51) Int. Cl.
H01L 51/50 (2006.01)
C09K 11/06 (2006.01)
H01L 51/00 (2006.01)
H05B 33/14 (2006.01)
C07F 15/00 (2006.01)

(52) U.S. Cl.
CPC ...... *H01L 51/5012* (2013.01); *C07F 15/0033* (2013.01); *C09K 11/06* (2013.01); *H01L 51/0085* (2013.01); *H05B 33/14* (2013.01); *C09K 2211/1007* (2013.01); *C09K 2211/1029* (2013.01); *C09K 2211/185* (2013.01); *H01L 51/5016* (2013.01)

(58) Field of Classification Search
CPC .................................................. H01L 51/0085
See application file for complete search history.

(56) References Cited

U.S. PATENT DOCUMENTS 8,669,547 B2 * 3/2014 Lecloux ................ C09K 11/06
257/40
2007/0202358 A1 8/2007 Sano et al.
2008/0009627 A1 1/2008 Tsuboyama et al.
2008/0220265 A1 9/2008 Xia
2009/0108737 A1 4/2009 Kwong
2011/0204339 A1 8/2011 Dobbs et al.
2012/0313087 A1 12/2012 Buchholz et al.

FOREIGN PATENT DOCUMENTS

| DE | 102010009193 A | 8/2011 |
|---|---|---|
| EP | 1754267 A | 2/2007 |
| JP | 2005-536565 | 12/2005 |
| JP | 2007266598 A | 10/2007 |
| JP | 2007-305783 | 11/2007 |
| JP | 200813700 A | 1/2008 |
| JP | 2008504371 A | 2/2008 |
| JP | 2011176250 A | 9/2011 |
| JP | 2013-539206 | 10/2013 |
| KR | 1020110088457 A | 8/2011 |
| WO | 2005124889 A1 | 12/2005 |
| WO | 2009073245 A1 | 6/2009 |
| WO | 2011028479 A2 | 3/2011 |
| WO | 2011103953 A1 | 9/2011 |

OTHER PUBLICATIONS

Hohenleutner et al. Rapid Combinatorial Synthesis and Chromatography Based Screening of Phosphorescent Iridium Complexes for Solution Processing, Adv. Funct. Mater. 2012, 22, 3406-3413.*
International Patent Application No. PCT/JP2012/074554, International Preliminary Report on Patentability, dated Apr. 1, 2014, 7 pages.

* cited by examiner

Primary Examiner — Brian E McDowell
(74) Attorney, Agent, or Firm — Riverside Law LLP

(57) ABSTRACT

An iridium complex which has a phenylpyridine bidentate ligand containing a group represented by the following general formula (A):

General Formula (A)

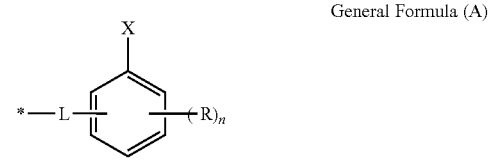

wherein X represents a cyano group or a halogenated alkyl group; L represents a single bond or a divalent linking group; R represents a substituent; n represents an integer of 0 to 4; * represents a binding site to a phenylpyridine bidentate ligand.

3 Claims, 2 Drawing Sheets

ORGANIC ELECTROLUMINESCENT ELEMENT AND NOVEL IRIDIUM COMPLEX

CROSS-REFERENCE TO RELATED APPLICATIONS

This application is a national stage entry of International Patent Application No. PCT/JP2012/074554, filed 25 Sep. 2012, which in turn claims priority to, and the benefit of, Japanese Patent Application No. 2011-218507, filed 30 Sep. 2011, all of which are incorporated herein by reference in their entireties.

TECHNICAL FIELD

The present invention relates to an organic electroluminescent element and a novel iridium complex. More specifically, the present invention relates to an organic electroluminescent element using an iridium complex, in which the iridium complex has three phenylpyridine bidentate ligands and at least one phenylpyridine ligand has a phenyl group substituted with a cyano group or a halogenated alkyl group.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have organic layers between a pair of electrodes, and utilize, for light emitting, energy of the exciton generated as a result of recombination of electrons injected from a cathode and holes injected from an anode in the organic layer.

Recently, by using phosphorescent light emitting materials such as an iridium complex, the efficiency of the elements is increasingly increased (see PTLs 1 to 4).

However, elements using iridium complexes in the related art need to be further improved from the viewpoint of durability.

CITATION LIST

Patent Literature

[PTL 1] WO09/073,245
[PTL 2] WO09/146,770
[PTL 3] JP-A-2001-357977
[PTL 4] JP-A-2006-86482

SUMMARY OF INVENTION

Technical Problem

It is an object of the present invention to provide an organic electroluminescent element having a low driving voltage, excellent efficiency, and excellent durability, and an iridium complex used for fabrication of the element.

Further, it is another object of the present invention to provide a compound useful for the organic electroluminescent elements as described above. Further, it is still another object of the present invention to provide a light emitting device, a display device, and an illumination device, each including the organic electroluminescent element of the present invention.

Solution to Problem

The present inventors have investigated and as a result, they have found that by introducing a phenyl group substituted with a cyano group or a halogenated alkyl group into an iridium complex containing three bidentate ligands having phenylpyridine skeletons, the durability of the organic electroluminescent element is improved significantly.

The present invention can be achieved by the following means.

[1] An organic electroluminescent element including a substrate, a pair of electrodes including an anode and a cathode, disposed on the substrate, and at least one organic layer including a light emitting layer, disposed between the electrodes, in which at least one kind of compound represented by the following general formula (1) is contained in at least one of the organic layers.

[Chem. 1]

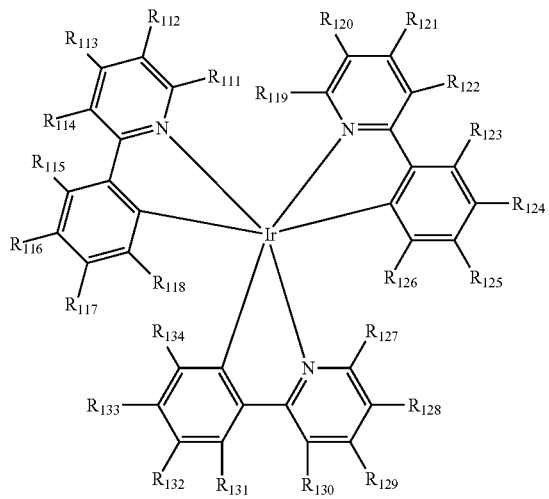

(1)

In the general formula (1), $R_{111}$ to $R_{134}$ each independently represent a hydrogen atom or a substituent. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, at least two adjacent groups out of $R_{127}$ to $R_{130}$, $R_{130}$ and $R_{131}$, or at least two adjacent groups out of $R_{131}$ to $R_{134}$ may be bonded to each other to form a ring, provided that at least one of $R_{111}$ to $R_{134}$ represents a group represented by the following general formula (A).

[Chem. 2]

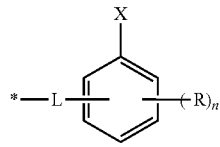

General formula (A)

In the general formula (A), X represents a cyano group or a halogenated alkyl group. L represents a single bond or a divalent linking group. R represents a substituent. In the case where a plurality of R's are present, they may be the same as or different from each other. n represents an integer of 0 to 4. * represents a binding site.

[2]

The organic electroluminescent element as described in [1], in which the compound represented by the general formula (1) is a compound represented by the following general formula (2).

[Chem. 3]

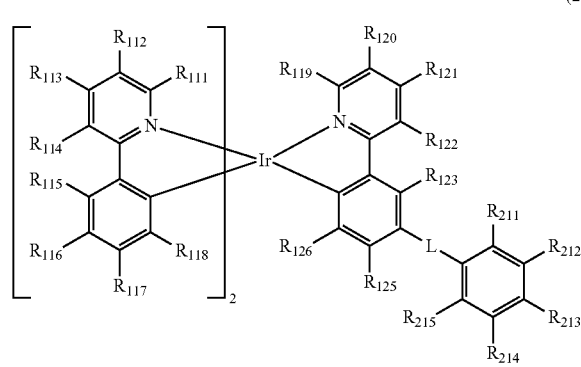

(2)

In the general formula (2), $R_{111}$ to $R_{123}$, $R_{125}$, $R_{126}$, and $R_{211}$ to $R_{215}$ each independently represent a hydrogen atom or a substituent. Two groups out of $R_{111}$ to $R_{118}$ may be the same as or different from each other. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{125}$ and $R_{126}$, or at least two adjacent groups out of $R_{211}$ to $R_{215}$ may be bonded to each other to form a ring. L represents a single bond or a divalent linking group, provided that at least one of $R_{211}$ to $R_{215}$ represents a cyano group or a halogenated alkyl group.

[3]

The organic electroluminescent element as described in [1], in which the compound represented by the general formula (1) is a compound represented by the following general formula (3).

[Chem. 4]

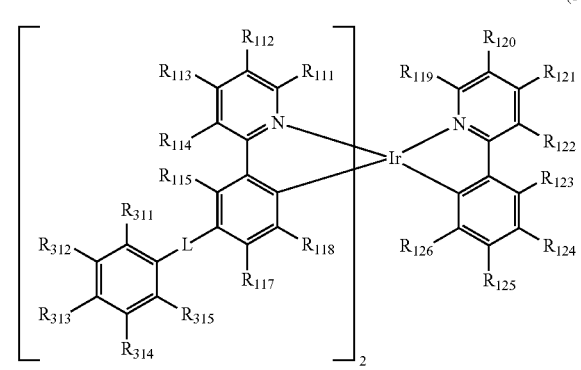

(3)

In the general formula (3), $R_{111}$ to $R_{115}$, $R_{117}$, $R_{118}$, $R_{119}$ to $R_{126}$, and $R_{311}$ to $R_{315}$ each independently represent a hydrogen atom or a substituent. Two groups out of $R_{111}$ to $R_{115}$, $R_{117}$, $R_{118}$, and $R_{311}$ to $R_{315}$ may be the same as or different from each other. At least two adjacent groups out of $R_{111}$ to $R_{114}$, $R_{114}$ and $R_{115}$, $R_{117}$ and $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{311}$ to $R_{315}$ may be bonded to each other to form a ring. L represents a single bond or a divalent linking group, provided that at least one of $R_{311}$ to $R_{315}$ represents a cyano group or a halogenated alkyl group.

[4]

The organic electroluminescent element as described in [1], in which the compound represented by the general formula (1) is a compound represented by the following general formula (4).

[Chem. 5]

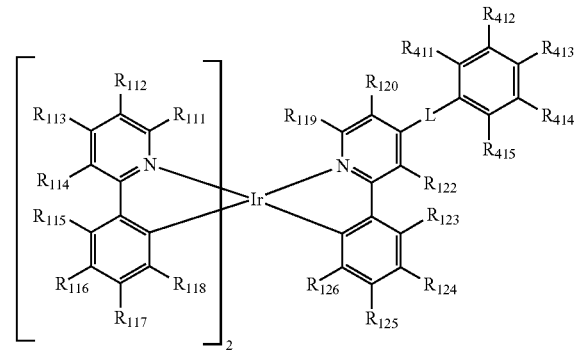

(4)

In the general formula (4), $R_{111}$ to $R_{120}$, $R_{122}$ to $R_{126}$, and $R_{411}$ to $R_{415}$ each independently represent a hydrogen atom or a substituent. Two groups out of $R_{111}$ to $R_{118}$ may be the same as or different from each other. At least two adjacent groups out of $R_{111}$ to $R_{114}$, $R_{114}$ and $R_{115}$, at least two adjacent groups out of $R_{115}$ to $R_{118}$, $R_{119}$ and $R_{120}$, $R_{122}$ and $R_{123}$, at least two adjacent groups out of $R_{123}$ to $R_{126}$, or at least two adjacent groups out of $R_{411}$ to $R_{415}$ may be bonded to each other to form a ring. L represents a single bond or a divalent linking group, provided that at least one of $R_{411}$ to $R_{415}$ represents a cyano group or a halogenated alkyl group.

[5]

The organic electroluminescent element as described in [1], in which the compound represented by the general formula (1) is a compound represented by the following general formula (5).

[Chem. 6]

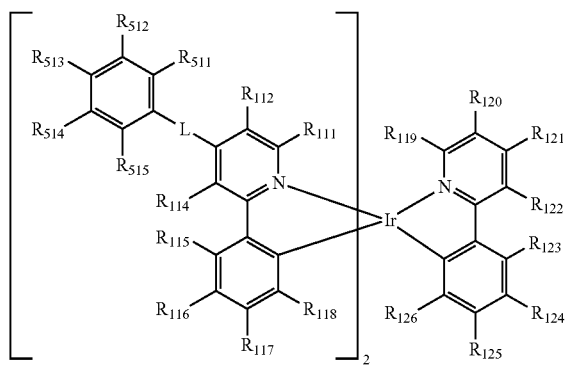

(5)

In the general formula (5), $R_{111}$, $R_{112}$, $R_{114}$, $R_{115}$ to $R_{126}$, and $R_{511}$ to $R_{515}$ each independently represent a hydrogen atom or a substituent. Two groups out of $R_{111}$, $R_{112}$, $R_{114}$, $R_{115}$ to $R_{118}$, and $R_{511}$ to $R_{515}$ may be each the same as or different from each other. $R_{111}$ and $R_{112}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{511}$ to $R_{515}$ may be bonded to each other to form a ring. L represents a single bond or a divalent linking group, provided that at least one of $R_{511}$ to $R_{515}$ represents a cyano group or a halogenated alkyl group.

[6]

The organic electroluminescent element as described in [1], in which the compound represented by the general formula (1) is a compound represented by the following general formula (6).

[Chem. 7]

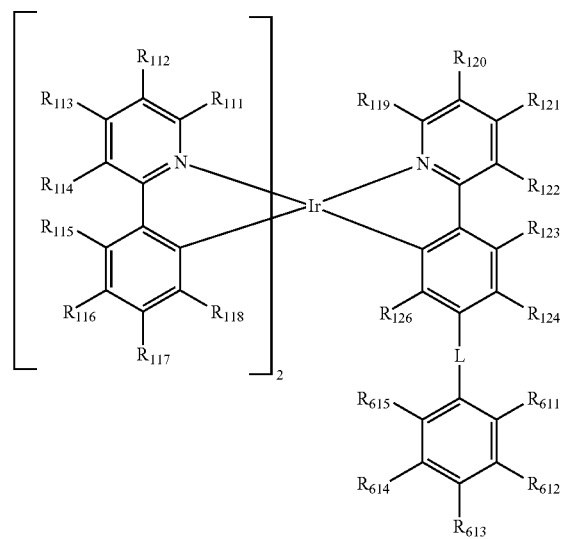

(6)

In the general formula (6), $R_{111}$ to $R_{124}$, $R_{126}$, and $R_{611}$ to $R_{615}$ each independently represent a hydrogen atom or a substituent. Two groups out of $R_{111}$ to $R_{118}$ may be each the same as or different from each other. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{123}$ and $R_{124}$, or at least two adjacent groups out of $R_{611}$ to $R_{615}$ may be bonded to each other to form a ring. L represents a single bond or a divalent linking group, provided that at least one of $R_{611}$ to $R_{615}$ represents a cyano group or a halogenated alkyl group.

[7]

The organic electroluminescent element as described in any one of [1] to [6], in which X in the general formula (A), at least one of $R_{211}$ to $R_{215}$ in the general formula (2), at least one of $R_{311}$ to $R_{315}$ in the general formula (3), at least one of $R_{411}$ to $R_{415}$ in the general formula (4), at least one of $R_{511}$ to $R_{515}$ in the general formula (5), and at least one of $R_{611}$ to $R_{615}$ in the general formula (6) are cyano groups.

[8]

The organic electroluminescent element as described in any one of [1] to [7], in which a compound represented by any one of the general formulae (1) to (6) is contained in the light emitting layer.

[9]

The organic electroluminescent element as described in [8], further containing a compound having a cyano group, in addition to the compound represented by any one of the general formulae (1) to (6), in the light emitting layer.

[10] A light emitting device using the organic electroluminescent element as described in any one of [1] to [9].

[11] A display device using the organic electroluminescent element as described in any one of [1] to [9].

[12] An illumination device using the organic electroluminescent element as described in any one of [1] to [9].

[13]

A compound represented by the following general formula (2).

[Chem. 8]

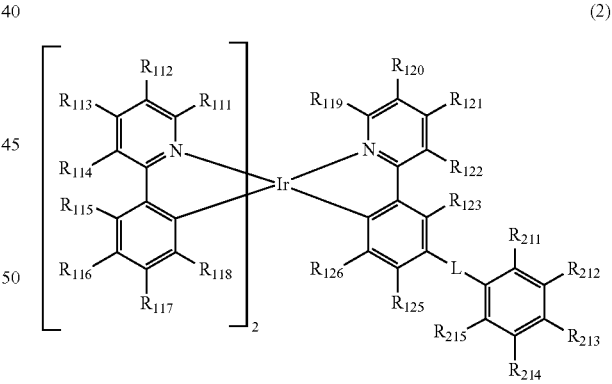

(2)

In the general formula (2), $R_{111}$ to $R_{123}$, $R_{125}$, $R_{126}$, and $R_{211}$ to $R_{215}$ each independently represent a hydrogen atom or a substituent. Two groups out of $R_{111}$ to $R_{118}$ may be each the same as or different from each other. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{125}$ and $R_{126}$, or at least two adjacent groups out of $R_{211}$ to $R_{215}$ may be bonded to each other to form a ring. L represents a single bond or a divalent linking group, provided that at least one of $R_{211}$ to $R_{215}$ represents a cyano group or a halogenated alkyl group.

Advantageous Effects of Invention

According to the present invention, an organic electroluminescent element having a low driving voltage, excellent efficiency, and excellent durability can be provided. Further, a light emitting device, a display device, and an illumination device, each using the organic electroluminescent element, can be provided.

In addition, according to the present invention, an iridium complex used for fabrication of an organic electroluminescent element having a low driving voltage, excellent efficiency, and excellent durability can be provided.

DESCRIPTION OF EMBODIMENTS

Figure 1:
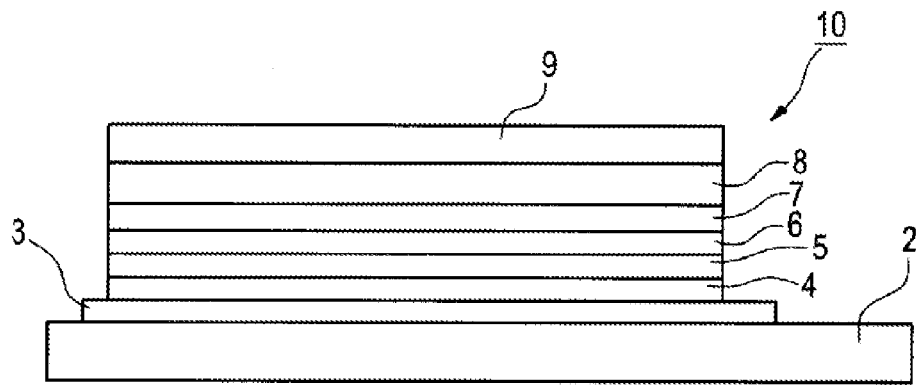
FIG. 1 is a schematic view showing one example of a configuration of an organic electroluminescent element according to the present invention.

In the description of the general formula (1), the hydrogen atom includes isotopes thereof (deuterium atom and the like), and the atom additionally constituting the substituent includes isotopes thereof.

In the present invention, when referring to a "substituent", the substituent may be further substituted. For example, when the "alkyl group" is referred to in the present invention, it includes an alkyl group substituted with a fluorine atom (for example, a trifluoromethyl group) and an alkyl group substituted with an aryl group (for example, a triphenylmethyl group), but when "an alkyl group having 1 to 6 carbon atoms" is referred to herein, it represents any of alkyl groups having 1 to 6 carbon atoms, including the alkyl groups which are substituted.

In the present invention, the Substituent Group A is defined as follows.

(Substituent Group A)

An alkyl group (preferably having 1 to 30 carbon atoms, more preferably having 1 to 20 carbon atoms, and particularly preferably having 1 to 10 carbon atoms; for example, methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), an amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and an aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), a phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxyl group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). [Compound Represented by General Formula (1)]

Hereinbelow, the compound represented by the general formula (1) will be described.

[Chem. 9]

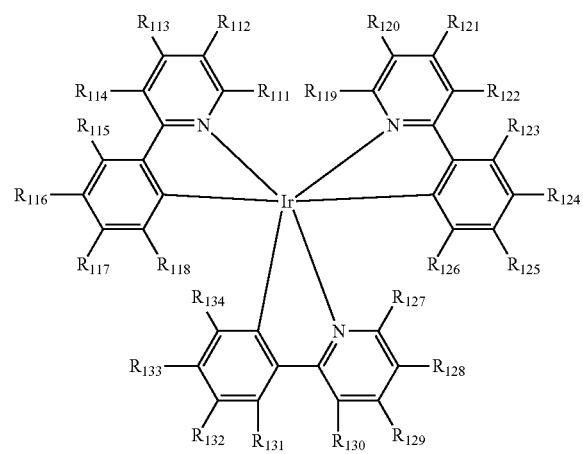

(1)

In the general formula (1), $R_{111}$ to $R_{134}$ each independently represent a hydrogen atom or a substituent. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, at least two adjacent groups out of $R_{127}$ to $R_{130}$, $R_{130}$ and $R_{131}$, or at least two adjacent groups out of $R_{131}$ to $R_{134}$ may be bonded to each other to form a ring, provided that at least one of $R_{111}$ to $R_{134}$ represents a group represented by the following general formula (A).

[Chem. 10]

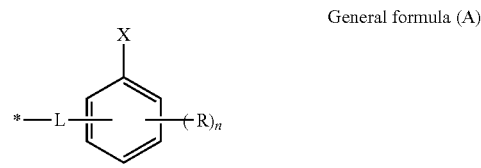

General formula (A)

In the general formula (A), X represents a cyano group or a halogenated alkyl group. L represents a single bond or a divalent linking group. R represents a substituent. In the case where a plurality of R's are present, they may be the same as or different from each other. n represents an integer of 0 to 4. * represents a binding site.

In the general formula (1), a bond between an iridium atom and a nitrogen atom, and a bond between an iridium atom and a carbon atom are represented by solid lines, but the bonds may be covalent bonds or coordinate bonds. Further, this also applies to the general formulae (2) to (6) as described later.

In the general formula (1), $R_{111}$ to $R_{134}$ each independently represent a hydrogen atom or a substituent. Examples of the substituent include the groups selected from the Substituent Group A.

$R_{111}$ to $R_{134}$ are each preferably a hydrogen atom, an alkyl group, an aryl group, a heteroaryl group, or a cyano group, and for the reason that the durability is excellent, a hydrogen atom, an alkyl group, an aryl group, or a cyano group is more preferred, and a hydrogen atom, an alkyl group, or an aryl group is still more preferred. With regard to the alkyl group, the preferred range of the alkyl groups in the Substituent Group A preferably includes an alkyl group having 1 to 5 carbon atoms, more preferably an alkyl group having 1 to 3 carbon atoms, particularly preferably a methyl group, an ethyl group, or a propyl group, still more preferably a methyl group or an ethyl group, and most preferably a methyl group. With regard to the aryl group, the preferred range of the aryl groups in the Substituent Group A preferably includes an aryl group having 6 to 10 carbon atoms, particularly preferably a phenyl group or a naphthyl group, and most preferably a phenyl group. Preferred examples the heteroaryl group include a pyridyl group, a pyrazinyl group, a pyrimidyl group, a pyridazinyl group, a pyrrolyl group, a pyrazolyl group, a triazolyl group, an imidazolyl group, an oxazolyl group, a triazolyl group, an isoxazolyl group, and an isothiazolyl group.

In the case where $R_{111}$ to $R_{134}$ each represent a substituent, the substituent may be further substituted with an additional substituent, examples of the additional substituent include the groups selected from the Substituent Group A, and the additional substituent is preferably an alkyl group, an aryl group, a heteroaryl group, or a cyano group, and more preferably an alkyl group or an aryl group. The preferred ranges of the alkyl group and the aryl group as the additional substituents are the same as the preferred ranges in the case where $R_{111}$ to $R_{134}$ as described above are each an alkyl group or an aryl group.

At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, at least two adjacent groups out of $R_{127}$ to $R_{130}$, $R_{130}$ and $R_{131}$, or at least two adjacent groups out of $R_{131}$ to $R_{134}$ may be bonded to each other to form a ring.

From the viewpoint of obtaining light emitting materials in a yellow color through a red color, the aspect of forming a ring is preferably at least one aspect selected from an aspect in which $R_{111}$ and $R_{112}$ are bonded to each other to form a ring, an aspect in which $R_{119}$ and $R_{120}$ are bonded to each other to form a ring, an aspect in which $R_{127}$ and $R_{128}$ are bonded to each other to form a ring, an aspect in which $R_{112}$ and $R_{113}$ are bonded to each other to form a ring, an aspect in which $R_{120}$ and $R_{121}$ are bonded to each other to form a ring, an aspect in which $R_{128}$ and $R_{129}$ are bonded to each other to form a ring, an aspect in which $R_{113}$ and $R_{114}$ are bonded to each other to form a ring, an aspect in which $R_{121}$ and $R_{122}$ are bonded to each other to form a ring, and an aspect in which $R_{129}$ and $R_{130}$ are bonded to each other to form a ring.

Examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring, and a cycloalkane ring, and preferably a benzene ring.

These rings thus formed may have a substituent, examples of the substituent include the Substituent Group A, and the substituent is preferably an alkyl group, an aryl group, or a cyano group, and more preferably an alkyl group or an aryl group.

At least one of $R_{111}$ to $R_{134}$ in general formula (1) represents a group represented by the general formula (A).

The number of the groups out of $R_{111}$ to $R_{134}$ in the general formula (1) which represent a group represented by general formula (A) is preferably 3 or less from the viewpoint of easiness of deposition, and more preferably 1 to 3, more preferably 1 or 2, and still more preferably 1.

X in the general formula (A) represents a cyano group or a halogenated alkyl group. Examples of the halogen in the halogenated alkyl group include a fluorine atom, a chlorine atom, a bromine atom, and an iodine atom, and preferably a fluorine atom. As the halogenated alkyl group, a fluoroalkyl group having 1 to 3 carbon atoms is preferred, and a fluoroalkyl group having one carbon atom is more preferred.

From the viewpoint of improvement of the durability of an organic EL element, X in the general formula (A) is preferably a cyano group.

L in the general formula (A) represents a single bond or a divalent linking group. Examples of the divalent linking group include an arylene group or an alkylene group.

L is preferably a single bond or an arylene group. As the arylene group, an arylene group consisting of 1 to 3 benzene rings is preferred, an arylene group consisting of 1 or 2 benzene rings is more preferred, and specifically, a phenylene group, a biphenylene group, or a terphenylene group is preferred, and a phenylene group or a biphenylene group is still more preferred.

In the case where L represents an arylene group, specific examples of L include the following L1 to L15, and for the reason of excellent element characteristics, L1, L2, L4, L5, L7, L8, L13, or L14 is preferred, and L2 or L8 is more preferred.

Furthermore, in L1 to L15 below, * represents a binding site. L1 to L15 may have additional substituents.

[Chem. 11]

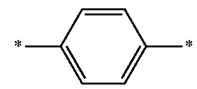 L1

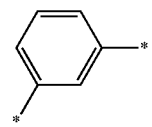 L2

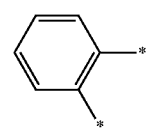 L3

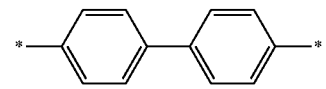 L4

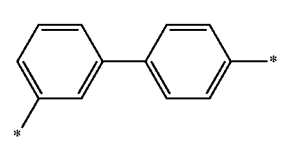 L5

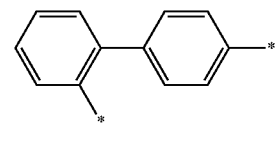 L6

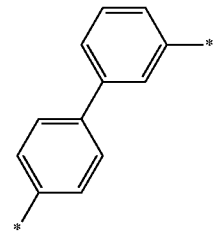 L7

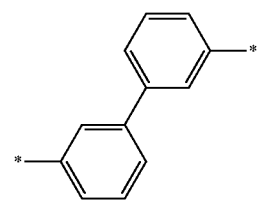 L8

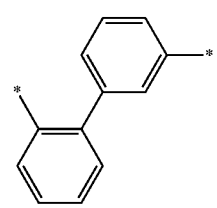 L9

-continued

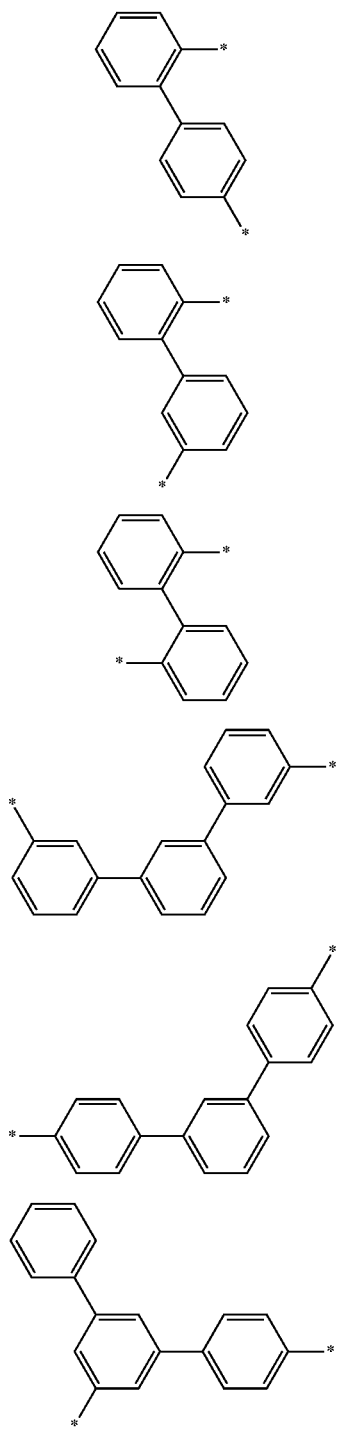

In the case where L represents a divalent linking group, it may have a substituent. Examples of the substituent include the groups selected from the Substituent Group A, and the substituent is preferably an alkyl group, an aryl group, or a cyano group.

R in the general formula (A) represents a substituent. Examples of the substituent include the groups selected from the Substituent Group A, and the substituent is preferably an alkyl group, an aryl group, or a cyano group, more preferably an alkyl group or an aryl group, and still more prefer-ably an aryl group. The preferred ranges of the alkyl group and the aryl group as the substituent are the same as the preferred ranges in the case where $R_{111}$ to $R_{134}$ as described above are each an alkyl group or an aryl group.

R may be substituted with another substituent, examples of the substituent include the groups selected from the Substituent Group A, and the substituent is preferably an alkyl group, an aryl group, a heteroaryl group, or a cyano group, more preferably an alkyl group or an aryl group, and still more preferably an aryl group.

n in the general formula (A) represents an integer of 0 to 4. n is preferably an integer of 0 to 3, more preferably an integer of 0 to 2, still more preferably 0 or 1, and particularly preferably 0.

The group represented by the general formula (A) is preferably substituted with two or less groups selected from $R_{116}$, $R_{124}$, and $R_{132}$, two or less groups selected from $R_{113}$, $R_{121}$, and $R_{129}$, two or less groups selected from $R_{112}$, $R_{120}$, and $R_{128}$, or two or less groups selected from $R_{117}$, $R_{125}$, and $R_{133}$; more preferably substituted with two or less groups selected from $R_{116}$, $R_{124}$, and $R_{132}$, two or less groups selected from $R_{113}$, $R_{121}$, and $R_{129}$, or two or less groups selected from $R_{117}$, $R_{125}$, and $R_{133}$; and still more preferably substituted with two or less groups selected from $R_{116}$, $R_{124}$, and $R_{132}$, or two or less groups selected from $R_{117}$, $R_{125}$, and $R_{133}$, in the general formula (1).

From the viewpoint of excellent durability, the compound represented by the general formula (1) is preferably a compound represented by any one of the following general formulae (2) to (6); and from the viewpoint of easiness of deposition, the compound represented by the general formula (1) is more preferably a compound represented by the following general formula (2), (4), or (6), still more preferably a compound represented by the following general formula (2) or (4), and particularly preferably a compound represented by the following general formula (2).

[Chem. 12]

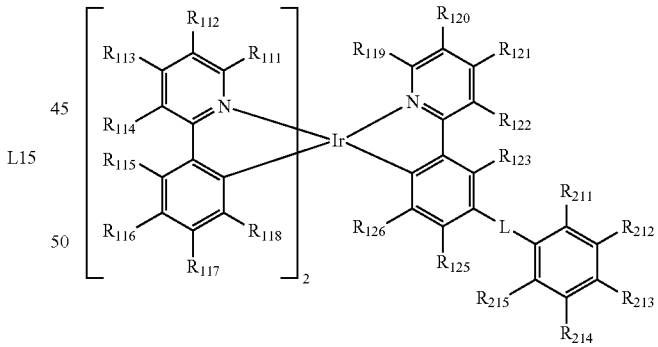

(2)

In the general formula (2), $R_{111}$ to $R_{123}$, $R_{125}$, $R_{126}$, and $R_{211}$ to $R_{215}$ each independently represent a hydrogen atom or a substituent. Two groups out of $R_{111}$ to $R_{118}$ may be each the same as or different from each other. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{125}$ and $R_{126}$, or at least two adjacent groups out of $R_{211}$ to $R_{215}$ may be bonded to each other to form a ring. L represents a single bond or a divalent linking group, provided that at least one of $R_{211}$ to $R_{215}$ represents a cyano group or a halogenated alkyl group.

In the general formula (2), the specific examples and the preferred ranges of $R_{111}$ to $R_{123}$, $R_{125}$, $R_{126}$, and $R_{211}$ to $R_{215}$ are the same as those of $R_{111}$ to $R_{134}$ in the general formula (1), and the specific examples and the preferred ranges of the additional substituents in the case where $R_{111}$ to $R_{123}$, $R_{125}$, $R_{126}$, and $R_{211}$ to $R_{215}$ represent a substituent are also the same as the specific examples and the preferred ranges of the additional substituents in the case where $R_{111}$ to $R_{134}$ in the general formula (1) represent a substituent.

In the general formula (2), $R_{111}$ to $R_{118}$ are each present in pairs, but each of them may be each the same as or different from each other, and are preferably the same as each other for the easiness of synthesis.

At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{125}$ and $R_{126}$, or at least two adjacent groups out of $R_{211}$ to $R_{215}$ may be bonded to each other to form a ring.

From the viewpoint of obtaining yellow through red light emitting materials, at least one aspect selected from an aspect where $R_{111}$ and $R_{112}$ are bonded to each other to form a ring, an aspect where $R_{119}$ and $R_{120}$ are bonded to each other to form a ring, an aspect where $R_{112}$ and $R_{113}$ are bonded to each other to form a ring, an aspect where $R_{120}$ and $R_{121}$ are bonded to each other to form a ring, an aspect where $R_{113}$ and $R_{114}$ are bonded to each other to form a ring, and an aspect where $R_{121}$ and $R_{122}$ are bonded to each other to form a ring is preferred.

The specific examples and the preferred ranges of the ring thus formed are the same as specific examples and the preferred ranges of the ring in the case where $R_{111}$ to $R_{134}$ in the general formula (1) form a ring. Further, the ring may have a substituent, and the specific examples and the preferred range of the substituent are the same as described in the general formula (1).

In the general formula (2), L represents a single bond or a divalent linking group, and the specific examples and the preferred range of L are the same as the specific examples and the preferred range of L in the general formula (1), and a single bond or a phenylene group is particularly preferred. Further, the substituent which L may have is the same as described in the general formula (1).

At least one of $R_{211}$ to $R_{215}$ in the general formula (2) represents a cyano group or a halogenated alkyl group, or preferably a cyano group.

The number of groups out of $R_{211}$ to $R_{215}$ in the general formula (2), which represent a cyano group or a halogenated alkyl group, is preferably 1 to 3, more preferably 1 to 2, and still more preferably 1.

The groups other than the cyano group or the halogenated alkyl group out of $R_{211}$ to $R_{215}$ in the general formula (2) is preferably a hydrogen atom, an alkyl group, or an aryl group, more preferably a hydrogen atom or an aryl group, and still more preferably a hydrogen atom.

A case where the compound represented by the general formula (1) is a compound represented by the following general formula (3) is also preferred.

[Chem. 13]

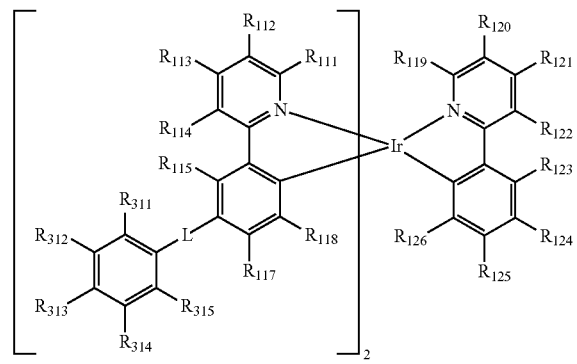

(3)

In the general formula (3), $R_{111}$ to $R_{115}$, $R_{117}$, $R_{118}$, $R_{119}$ to $R_{126}$, and $R_{311}$ to $R_{315}$ each independently represent a hydrogen atom or a substituent. Two groups out of $R_{111}$ to $R_{115}$, $R_{117}$, $R_{118}$, and $R_{311}$ to $R_{315}$ may be each the same as or different from each other. At least two adjacent groups out of $R_{111}$ to $R_{114}$, $R_{114}$ and $R_{115}$, $R_{117}$ and $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{311}$ to $R_{315}$ may be bonded to each other to form a ring. L represents a single bond or a divalent linking group, provided that at least one of $R_{311}$ to $R_{315}$ represents a cyano group or a halogenated alkyl group.

In the general formula (3), the specific examples and the preferred ranges of $R_{111}$ to $R_{115}$, $R_{117}$, $R_{118}$, $R_{119}$ to $R_{126}$, and $R_{311}$ to $R_{315}$ are the same as those of $R_{111}$ to $R_{134}$ in the general formula (1); the specific examples and the preferred ranges of the additional substituents which may be contained in the case where $R_{111}$ to $R_{115}$, $R_{117}$, $R_{118}$, $R_{119}$ to $R_{126}$, and $R_{311}$ to $R_{315}$ represent substituents are the same as the specific examples and the preferred ranges of the additional substituents in the case where $R_{111}$ to $R_{134}$ in the general formula (1) represent substituents.

In the general formula (3), $R_{111}$ to $R_{115}$, $R_{117}$, $R_{118}$, and $R_{311}$ to $R_{315}$ are present in pairs, but they may be each the same as or different from each other, and are preferably the same as each other for the easiness of synthesis.

At least two adjacent groups out of $R_{111}$ to $R_{114}$, $R_{114}$ and $R_{115}$, $R_{117}$ and $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{311}$ to $R_{315}$ may be bonded to each other to form a ring.

The specific examples and the preferred range of the ring thus formed are the same as the specific examples and the preferred range of the ring in the case where $R_{111}$ to $R_{134}$ in the general formula (1) form a ring. Further, the ring may have a substituent, and the specific examples and the preferred range of the substituent are the same as described in the general formula (1).

In the general formula (3), L represents a single bond or a divalent linking group, the specific examples and the preferred range of L are the same as the specific examples and the preferred range of L in the general formula (1), and a single bond or a phenylene group is particularly preferred. Further, the substituents which L may have are also the same as described in the general formula (1).

At least one of $R_{311}$ to $R_{315}$ in the general formula (3) represents a cyano group or a halogenated alkyl group, and preferably a cyano group.

The number of groups out of $R_{311}$ to $R_{315}$ in the general formula (3), which represent a cyano group or a halogenated alkyl group, is preferably 1 to 3, more preferably 1 to 2, and still more preferably 1.

The groups other than the cyano group or the halogenated alkyl group out of $R_{311}$ to $R_{315}$ in the general formula (3) is preferably a hydrogen atom, an alkyl group, or an aryl group, more preferably a hydrogen atom or an aryl group, and still more preferably a hydrogen atom.

Also preferred is a case where the compound represented by the general formula (1) is a compound represented by the following general formula (4).

[Chem. 14]

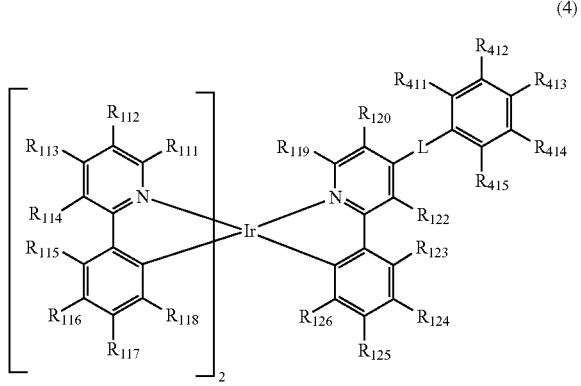

(4)

In the general formula (4), $R_{111}$ to $R_{120}$, $R_{122}$ to $R_{126}$, and $R_{411}$ to $R_{415}$ each independently represent a hydrogen atom or a substituent. Two groups out of $R_{111}$ to $R_{118}$ may be each the same as or different from each other. At least two adjacent groups out of $R_{111}$ to $R_{114}$, $R_{114}$ and $R_{115}$, at least two adjacent groups out of $R_{115}$ to $R_{118}$, $R_{119}$ and $R_{120}$, $R_{122}$ and $R_{123}$, at least two adjacent groups out of $R_{123}$ to $R_{126}$, or at least two adjacent groups out of $R_{411}$ to $R_{415}$ may be bonded to each other to form a ring. L represents a single bond or a divalent linking group, provided that at least one of $R_{411}$ to $R_{415}$ represents a cyano group or a halogenated alkyl group.

In the general formula (4), the specific examples and the preferred ranges of $R_{111}$ to $R_{120}$, $R_{122}$ to $R_{126}$, and $R_{411}$ to $R_{415}$ are the same as those of $R_{111}$ to $R_{134}$ in the general formula (1), and the specific examples and the preferred ranges of the additional substituents in the case where $R_{111}$ to $R_{120}$, $R_{122}$ to $R_{126}$, and $R_{411}$ to $R_{415}$ represent a substituent are also the same as the specific examples and the preferred ranges of the additional substituents in the case where $R_{111}$ to $R_{134}$ in the general formula (1) represent a substituent.

In the general formula (4), $R_{111}$ to $R_{118}$ are present in pairs, but each of them may be each the same as or different from each other, and are preferably the same as each other for the easiness of synthesis.

At least two adjacent groups out of $R_{111}$ to $R_{114}$, $R_{114}$ and $R_{115}$, at least two adjacent groups out of $R_{115}$ to $R_{118}$, $R_{119}$ and $R_{120}$, $R_{122}$ and $R_{123}$, at least two adjacent groups out of $R_{123}$ to $R_{126}$, and at least two adjacent groups out of $R_{411}$ to $R_{415}$ may be bonded to each other to form a ring.

The specific examples and the preferred range of the ring thus formed are the same as the specific examples and the preferred range of the ring in the case where $R_{111}$ to $R_{134}$ in the general formula (1) form a ring. Further, the ring may have a substituent, and the specific examples and the preferred range of the substituent are the same as described in the general formula (1).

In the general formula (4), L represents a single bond or a divalent linking group, the specific examples and the preferred range of L are the same as the specific examples and the preferred range of L in the general formula (1), and a single bond or a phenylene group is particularly preferred. Further, the substituents which L may have are also the same as described in the general formula (1).

At least one of $R_{411}$ to $R_{415}$ in the general formula (4) represents a cyano group or a halogenated alkyl group, or preferably a cyano group.

The number of groups out of $R_{411}$ to $R_{415}$ in the general formula (4), which represent a cyano group or a halogenated alkyl group, is preferably 1 to 3, more preferably 1 to 2, and still more preferably 1.

The groups other than the cyano group or the halogenated alkyl group out of $R_{411}$ to $R_{415}$ in the general formula (4) is preferably a hydrogen atom, an alkyl group, or an aryl group, more preferably a hydrogen atom or an aryl group, and still more preferably a hydrogen atom.

Also preferred is a case where the compound represented by the general formula (1) is a compound represented by the following general formula (5).

[Chem. 15]

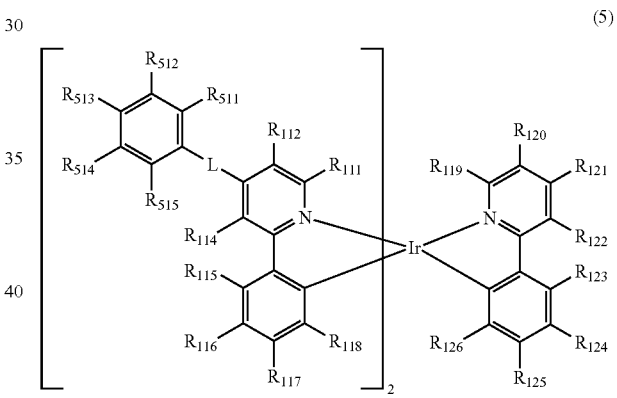

(5)

In the general formula (5), $R_{111}$, $R_{112}$, $R_{114}$, $R_{115}$ to $R_{126}$, and $R_{511}$ to $R_{515}$ each independently represent a hydrogen atom or a substituent. Two groups out of $R_{111}$, $R_{112}$, $R_{114}$, $R_{115}$ to $R_{118}$, and $R_{511}$ to $R_{515}$ may be each the same as or different from each other. $R_{111}$ and $R_{112}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{511}$ to $R_{515}$ may be bonded to each other to form a ring. L represents a single bond or a divalent linking group, provided that at least one of $R_{511}$ to $R_{515}$ represents a cyano group or a halogenated alkyl group.

In the general formula (5), the specific examples and the preferred ranges of $R_{111}$, $R_{112}$, $R_{114}$, $R_{115}$ to $R_{126}$, and $R_{511}$ to $R_{515}$ are the same as those of $R_{111}$ to $R_{134}$ in the general formula (1), and the specific examples and the preferred ranges of the additional substituents in the case where $R_{111}$, $R_{112}$, $R_{114}$, $R_{115}$ to $R_{126}$, and $R_{511}$ to $R_{515}$ represent a substituent are also the same as the specific examples and the preferred ranges of the additional substituents in the case where $R_{111}$ to $R_{134}$ in the general formula (1) represent a substituent.

In the general formula (5), $R_{111}$, $R_{112}$, $R_{114}$, $R_{115}$ to $R_{118}$, and $R_{511}$ to $R_{515}$ are each present in pairs, but each of them may be each the same as or different from each other, and are preferably the same as each other for the easiness of synthesis.

$R_{111}$ and $R_{112}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, or at least two adjacent groups out of $R_{511}$ to $R_{515}$ may be bonded to each other to form a ring.

The specific examples and the preferred range of the ring thus formed are the same as the specific examples and the preferred range of the ring in the case where $R_{111}$ to $R_{134}$ in the general formula (1) form a ring. Further, the ring may have a substituent, and the specific examples and the preferred range of the substituent are the same as described in the general formula (1).

In the general formula (5), L represents a single bond or a divalent linking group, the specific examples and the preferred range of L are the same as the specific examples and the preferred range of L in the general formula (1), and a single bond or a phenylene group is particularly preferred. Further, the substituents which L may have are also the same as described in the general formula (1).

At least one of $R_{511}$ to $R_{515}$ in the general formula (5) represents a cyano group or a halogenated alkyl group, or preferably a cyano group.

The number of groups out of $R_{511}$ to $R_{515}$ in the general formula (5), which represent a cyano group or a halogenated alkyl group, is preferably 1 to 3, more preferably 1 to 2, and still more preferably 1.

The groups other than the cyano group or the halogenated alkyl group out of $R_{511}$ to $R_{515}$ in the general formula (5) is preferably a hydrogen atom, an alkyl group, or an aryl group, more preferably a hydrogen atom or an aryl group, and still more preferably a hydrogen atom.

Also preferred is a case where the compound represented by the general formula (1) is a compound represented by the following general formula (6).

[Chem. 16]

(6)

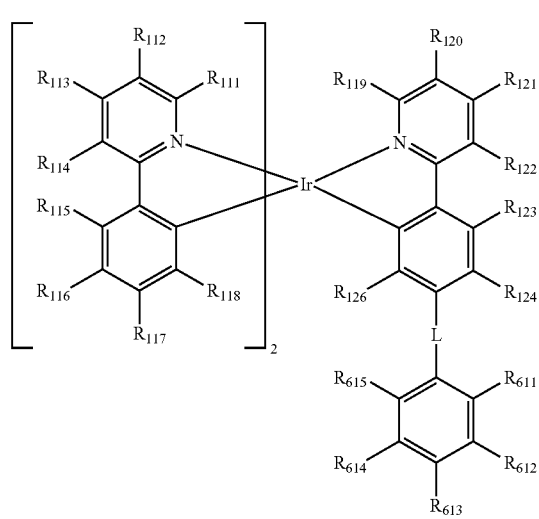

In the general formula (6), $R_{111}$ to $R_{124}$, $R_{126}$, and $R_{611}$ to $R_{615}$ each independently represent a hydrogen atom or a substituent. Two groups out of $R_{111}$ to $R_{118}$ may be each the same as or different from each other. At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{123}$ and $R_{124}$, or at least two adjacent groups out of $R_{611}$ to $R_{615}$ may be bonded to each other to form a ring. L represents a single bond or a divalent linking group, provided that at least one of $R_{611}$ to $R_{615}$ represents a cyano group or a halogenated alkyl group.

In the general formula (6), the specific examples and the preferred ranges of $R_{111}$ to $R_{124}$, $R_{126}$, and $R_{611}$ to $R_{615}$ are the same as those of $R_{111}$ to $R_{134}$ in the general formula (1), and the specific examples and the preferred ranges of the additional substituents in the case where $R_{111}$ to $R_{124}$, $R_{126}$, and $R_{611}$ to $R_{615}$ represent a substituent are also the same as the specific examples and the preferred ranges of the additional substituents in the case where $R_{111}$ to $R_{134}$ in the general formula (1) represent a substituent.

In the general formula (6), $R_{111}$ to $R_{118}$ are each present in pairs, but each of them may be each the same as or different from each other, and are preferably the same as each other for the easiness of synthesis.

At least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, $R_{123}$ and $R_{124}$, or at least two adjacent groups out of $R_{611}$ to $R_{615}$ may be bonded to each other to form a ring.

The specific examples and the preferred ranges of the ring thus formed are the same as specific examples and the preferred ranges of the ring in the case where $R_{111}$ to $R_{134}$ in the general formula (1) form a ring. Further, the ring may have a substituent, and the specific examples and the preferred range of the substituent are the same as described in the general formula (1).

In the general formula (6), L represents a single bond or a divalent linking group, the specific examples and the preferred range of L are the same as the specific examples and the preferred range of L in the general formula (1), and a single bond or a phenylene group is particularly preferred. Further, the substituents which L may have are also the same as described in the general formula (1).

At least one of $R_{611}$ to $R_{615}$ in the general formula (6) represents a cyano group or a halogenated alkyl group, or preferably a cyano group.

The number of groups out of $R_{611}$ to $R_{615}$ in the general formula (6), which represent a cyano group or a halogenated alkyl group, is preferably 1 to 3, more preferably 1 to 2, and still more preferably 1.

The groups other than the cyano group or the halogenated alkyl group out of $R_{611}$ to $R_{615}$ in the general formula (6) is preferably a hydrogen atom, an alkyl group, or an aryl group, more preferably a hydrogen atom or an aryl group, and still more preferably a hydrogen atom.

The molecular weight of the compound represented by the general formula (1) is preferably 400 to 1000, and more preferably 450 to 900, from the viewpoint of the sublimation suitability.

The glass transition temperature (Tg) of the compound represented by the general formula (1) is preferably 80° C. or higher, more preferably 90° C. or higher, still more preferably 100° C. or higher, and particularly preferably 110° C. or higher, from the viewpoint of stable operation during driving of an organic electroluminescent element at a high temperature or against heat generation during driving of the element.

Specific examples of the compound represented by the general formula (1) are listed below, but the present invention is not limited thereto.
[Chem. 17]
(1-1)
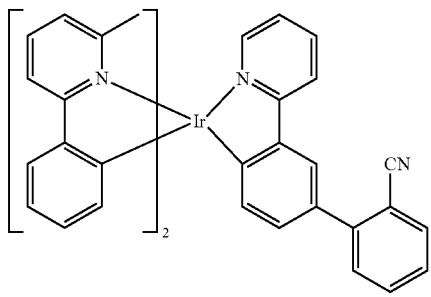
(1-2)
(1-3)
(1-4)
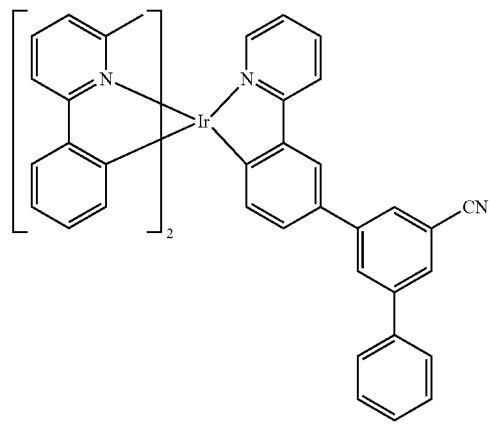
(1-5)
(1-6)
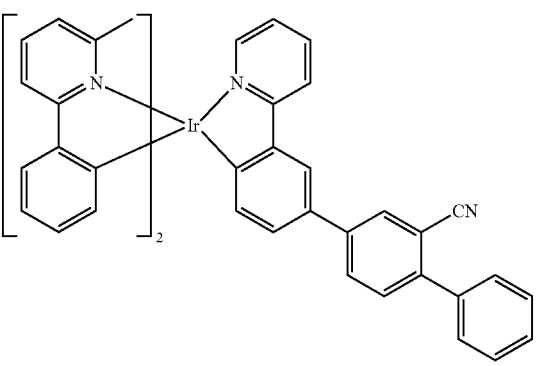
(1-7)
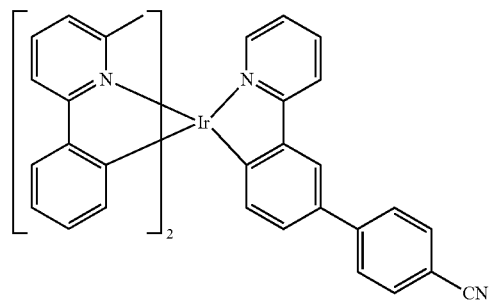
(1-8)
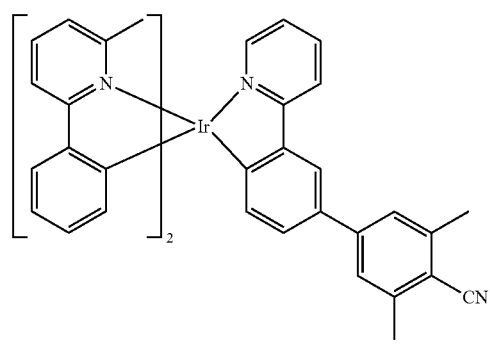

(1-9)
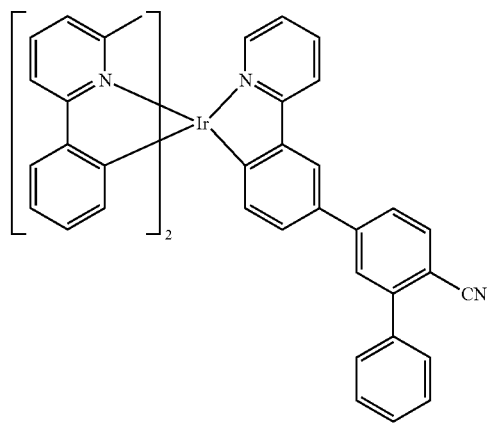
(1-12)
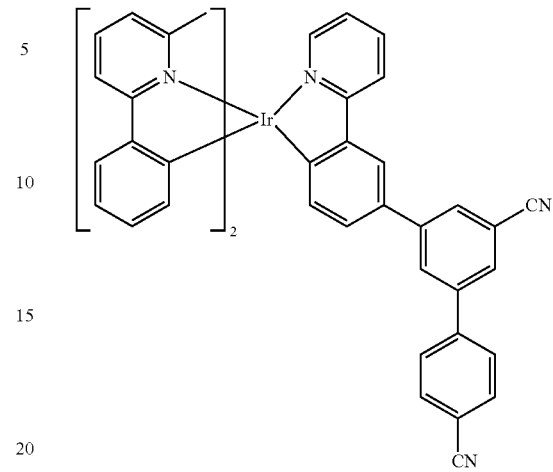
(1-10)
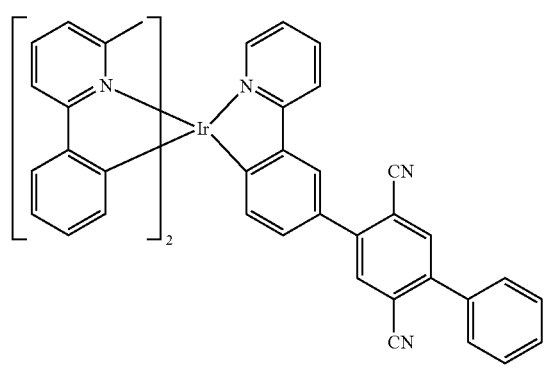
[Chem. 18]
(2-1)
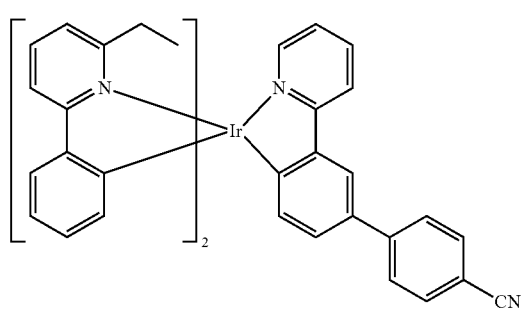
(2-2)
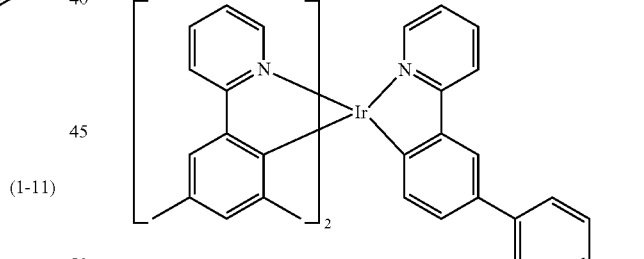
(1-11)
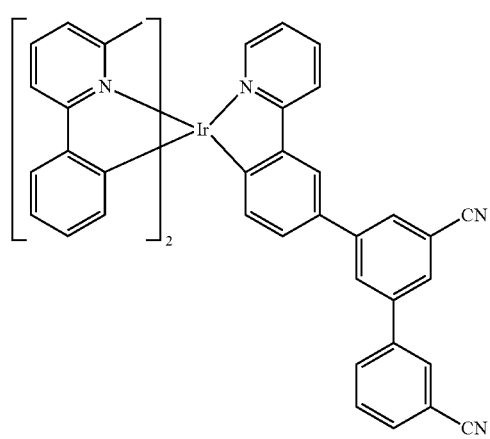
(2-3)

(2-4)
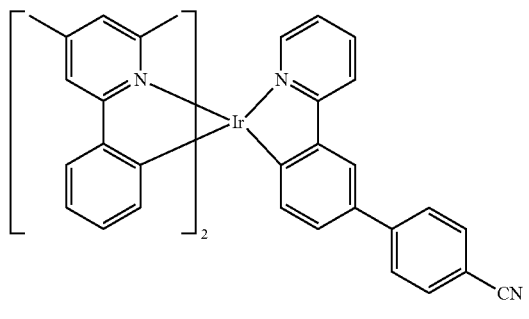
(2-5)
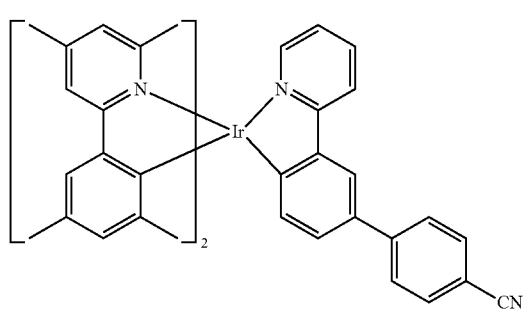
(2-6)
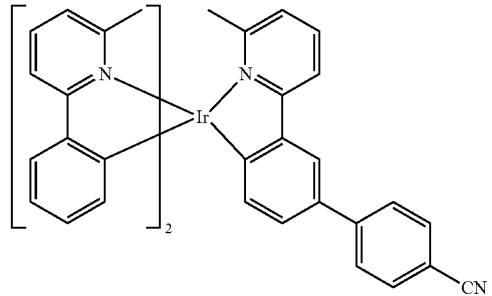
(2-7)
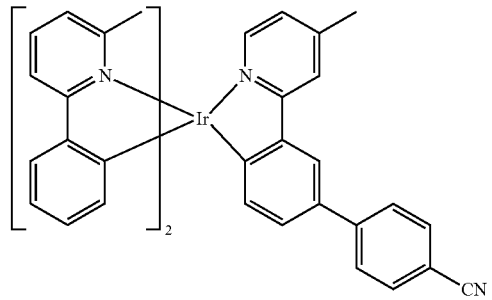
(2-8)
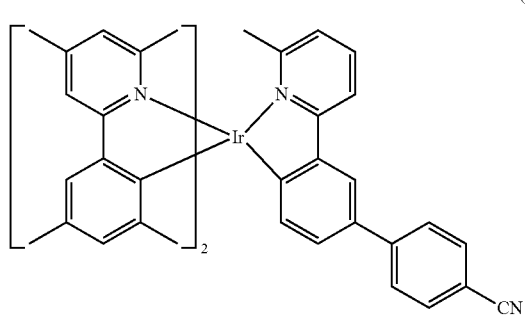
(2-9)
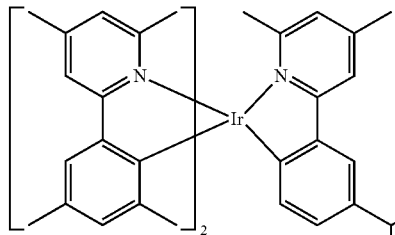
(2-10)
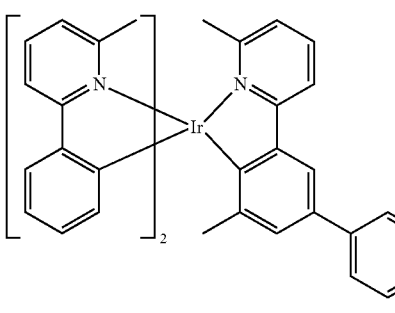
(2-11)
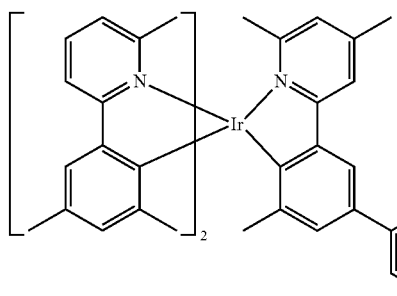
(2-12)
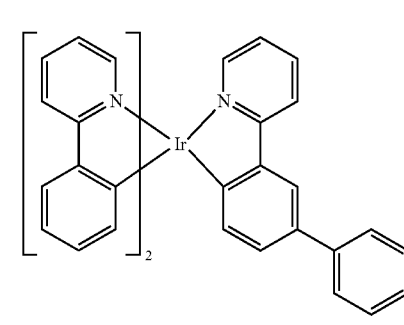
(2-13)
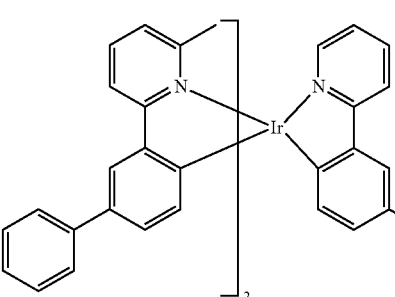

(2-14)
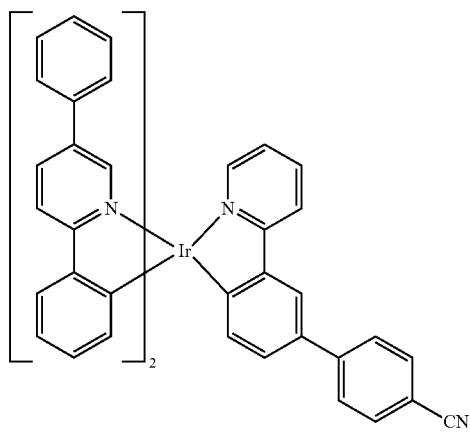
(2-15)
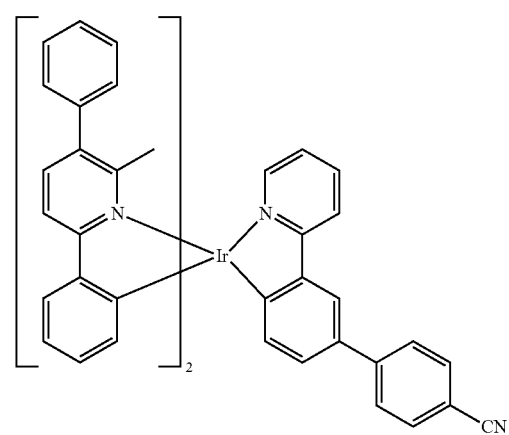
(2-16)
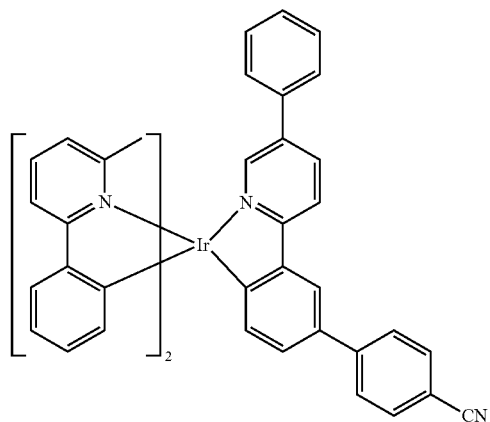
(2-17)
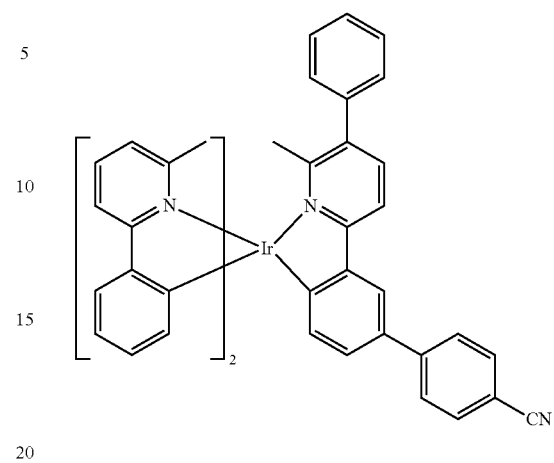
(2-18)
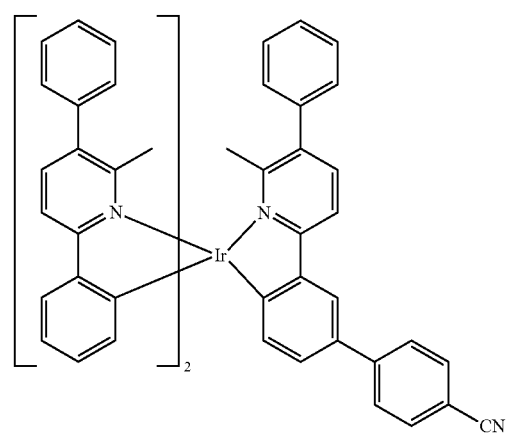
[Chem. 19]
(3-1)
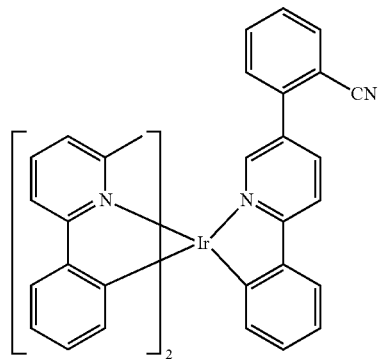

(3-2)
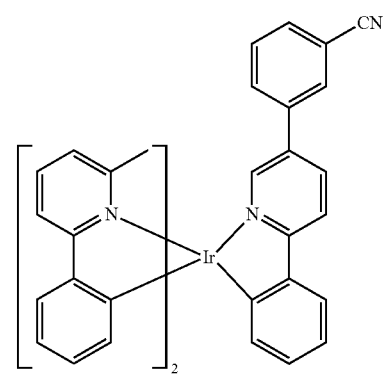
(3-3)
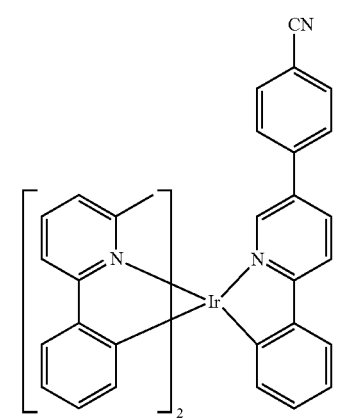
(3-4)
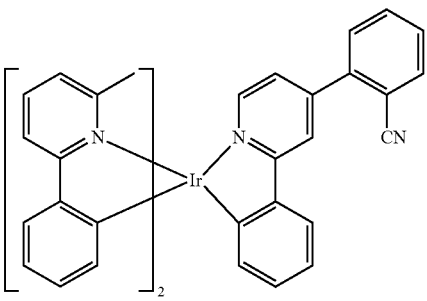
(3-5)
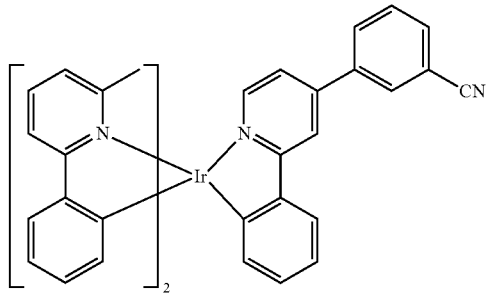
(3-6)
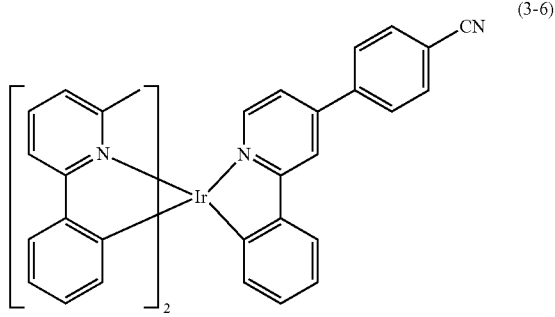
(3-7)
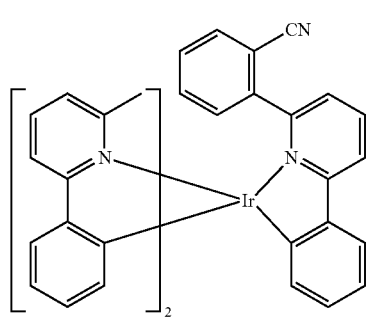
(3-8)
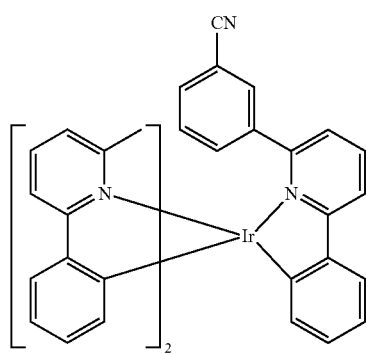
(3-9)
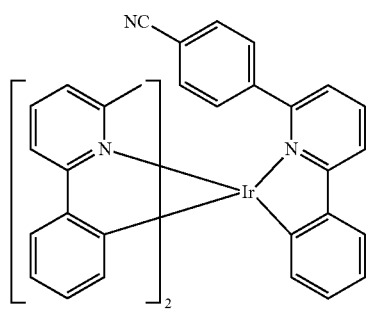
(3-10)
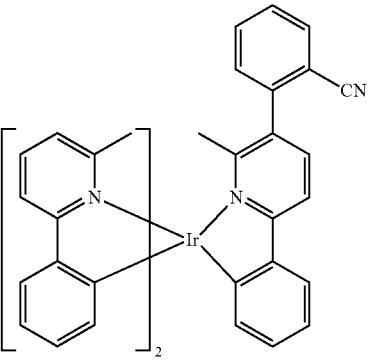

-continued
(3-11)
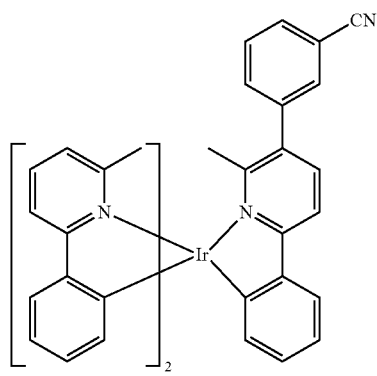
(3-12)
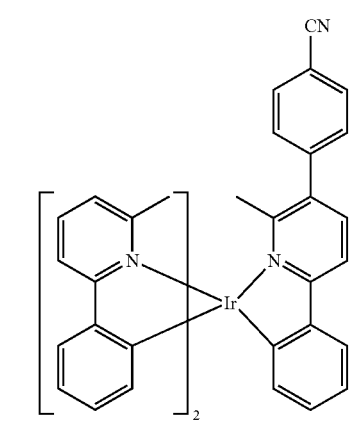
(3-13)
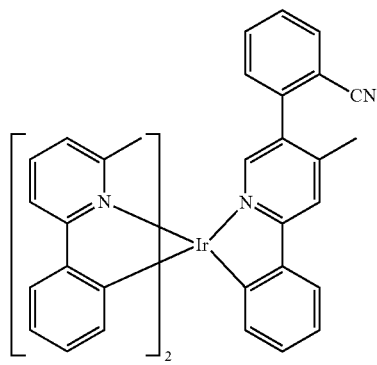
(3-14)
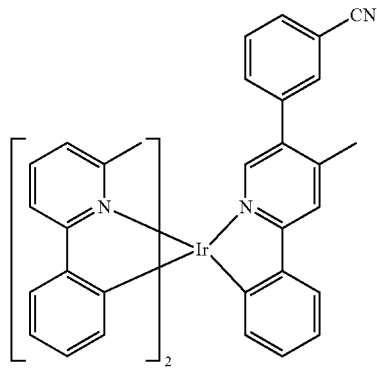
-continued
(3-15)
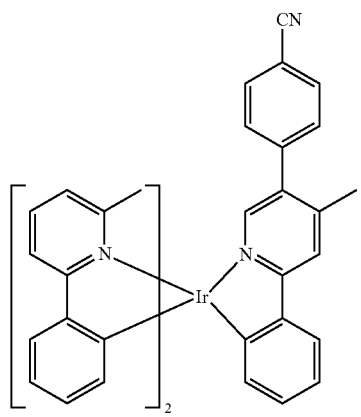
[Chem. 20]
(4-1)
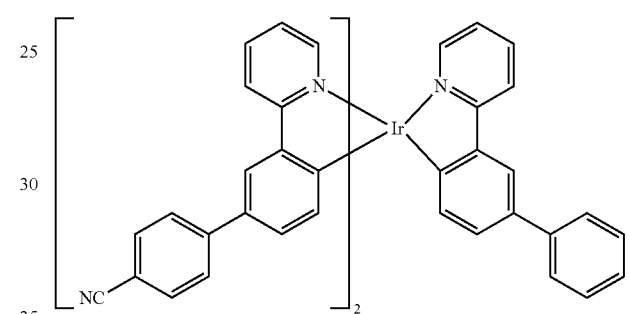
(4-2)
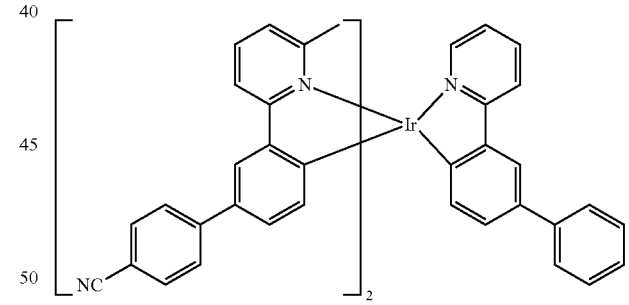
(4-3)
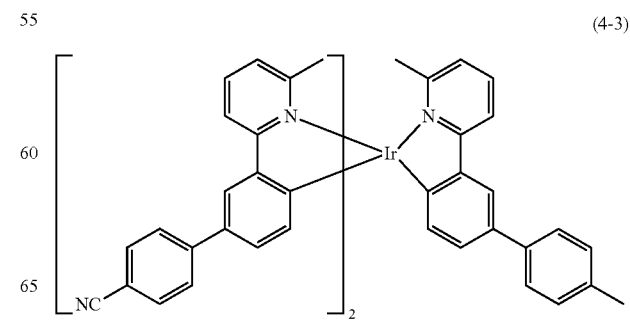

(4-4)
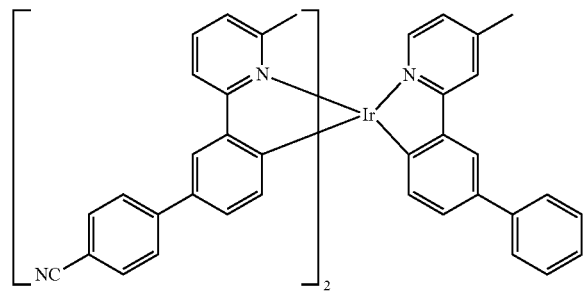
(4-5)
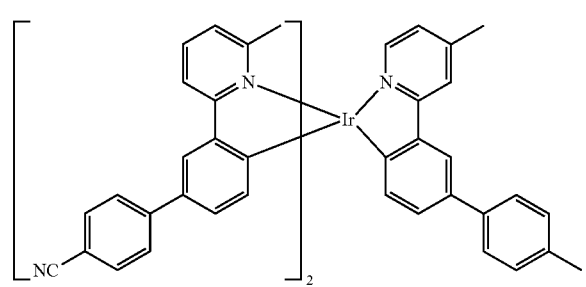
(4-6)
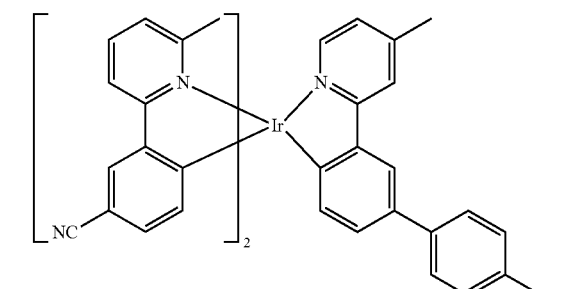
(4-7)
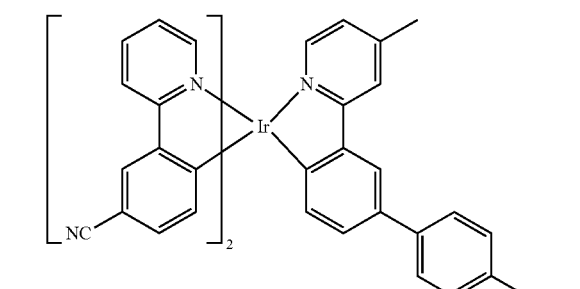
(4-8)
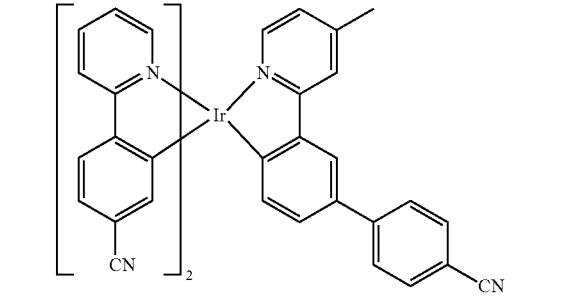
(4-9)
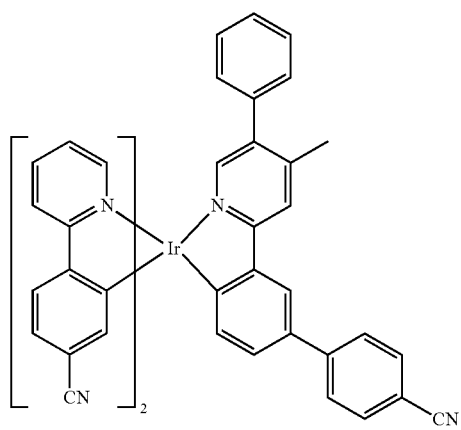
(4-10)
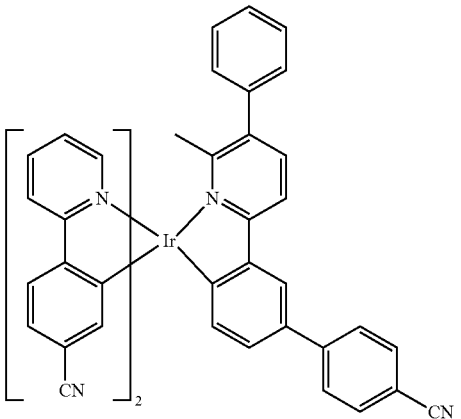
[Chem. 21]
(5-1)
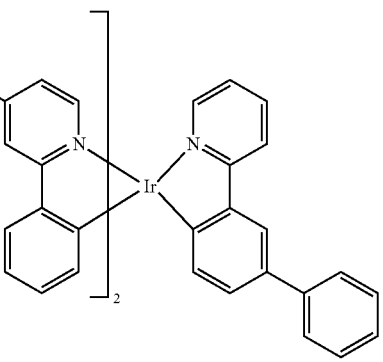

-continued
(5-2)
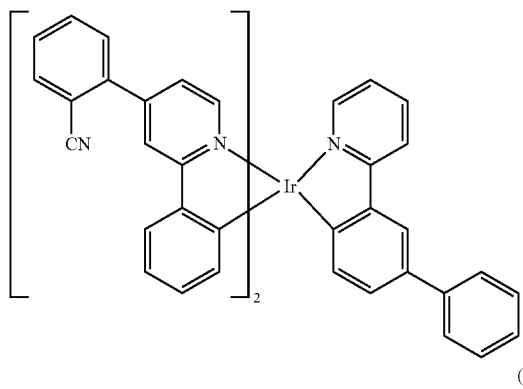
(5-3)
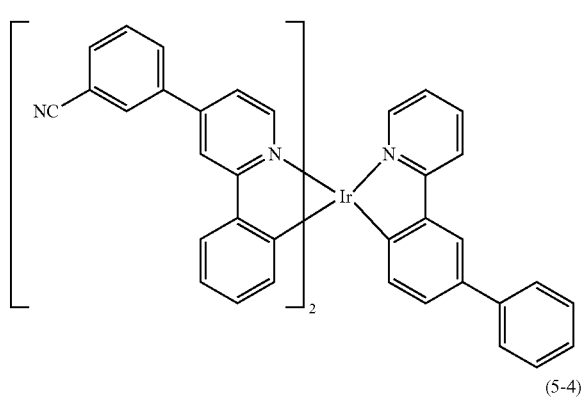
(5-4)
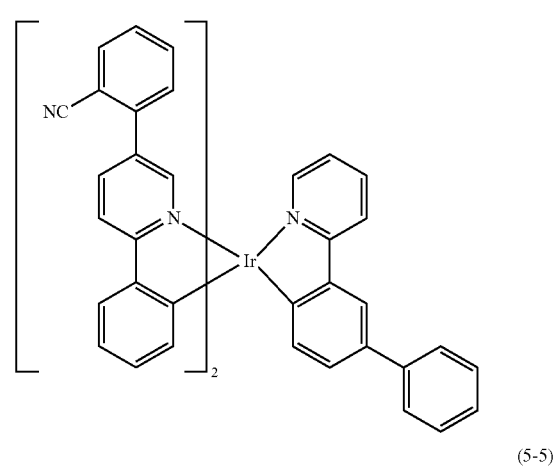
(5-5)
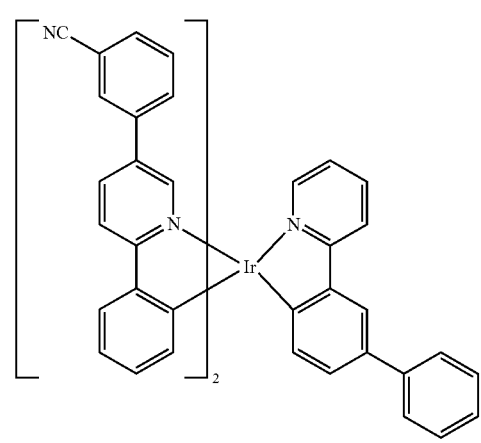
-continued
(5-6)
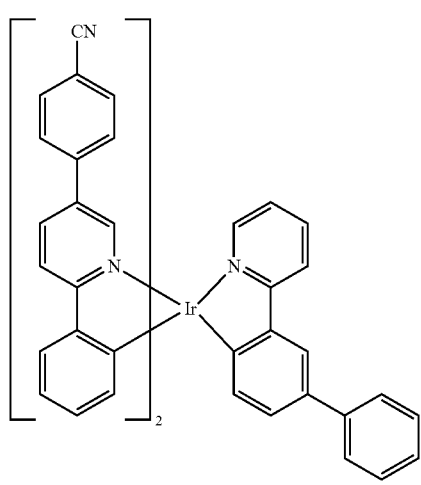
(5-7)
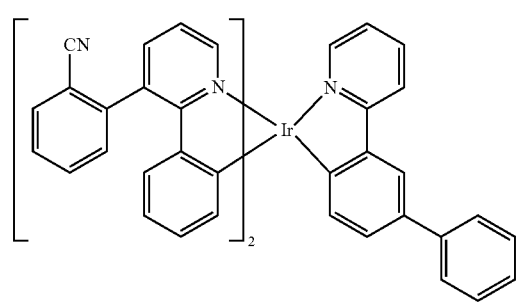
(5-8)
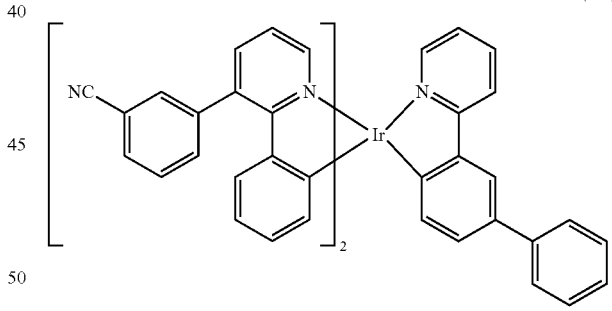
(5-9)

(5-10) 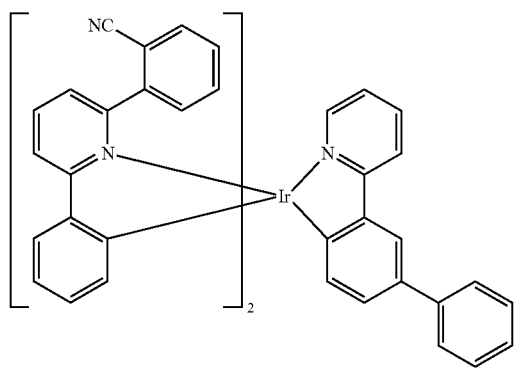
(5-11) 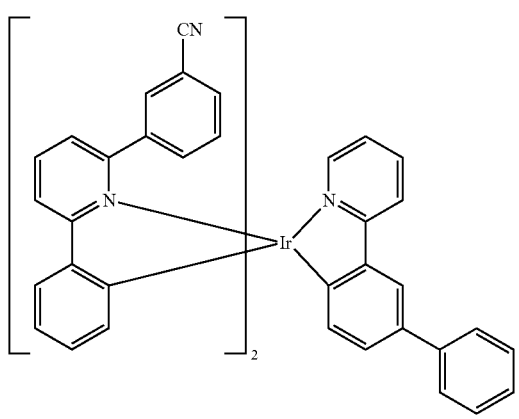
(5-12) 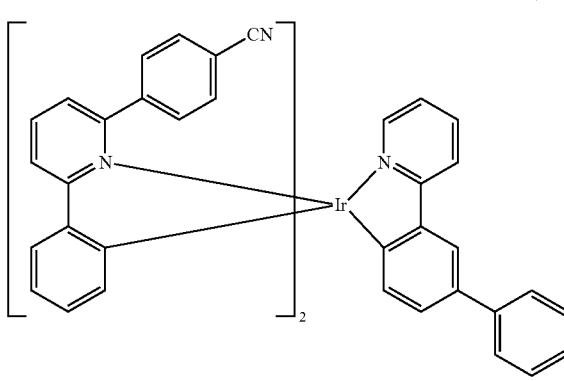
[Chem. 22]
(6-1) 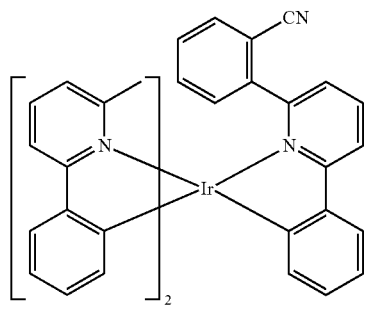
(6-2) 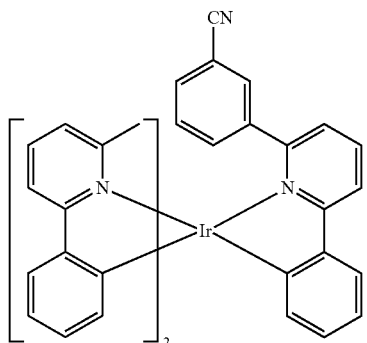
(6-3) 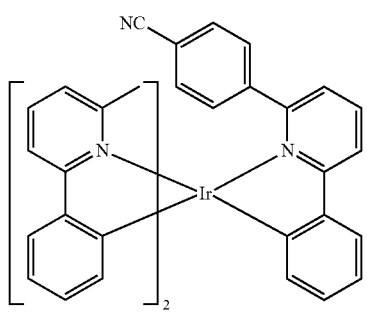
(6-4) 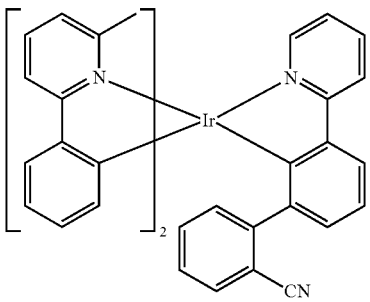
(6-5) 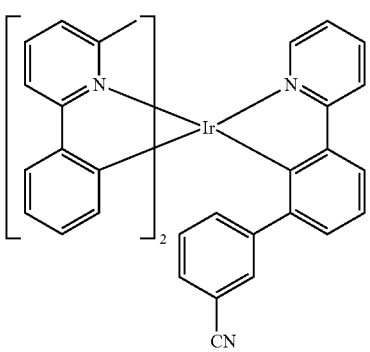
(6-6) 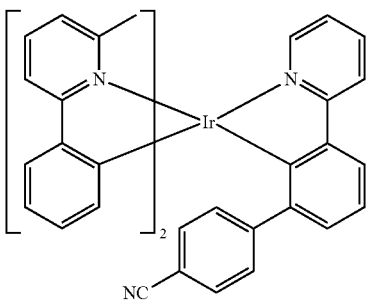

(6-7)
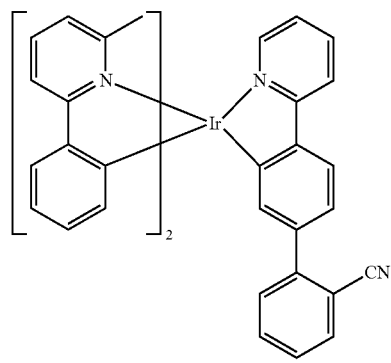
(6-8)
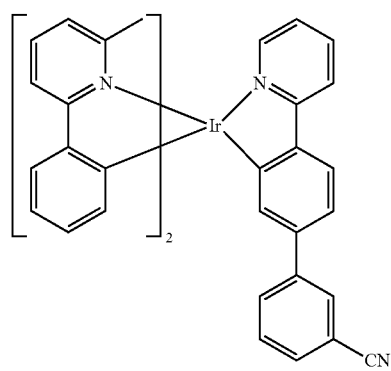
(6-9)
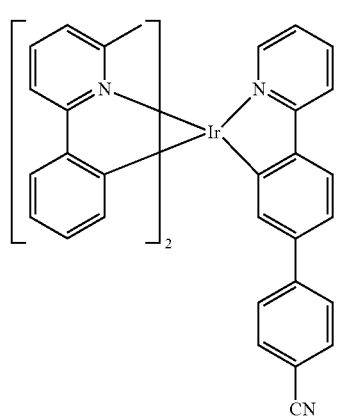
(6-10)
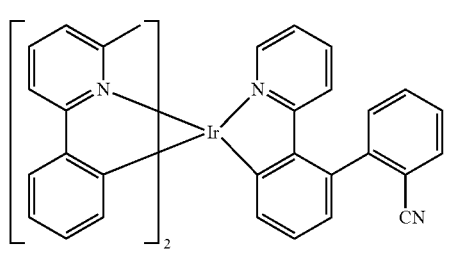
(6-11)
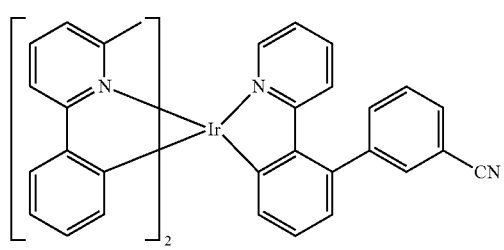
(6-12)
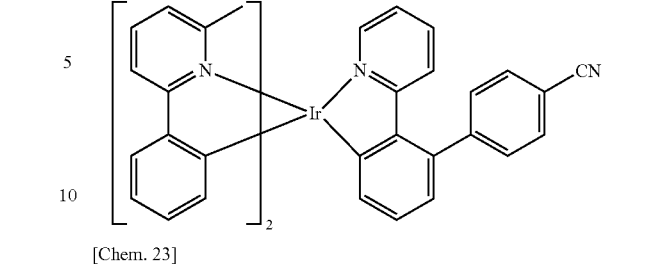
[Chem. 23]
(7-1)
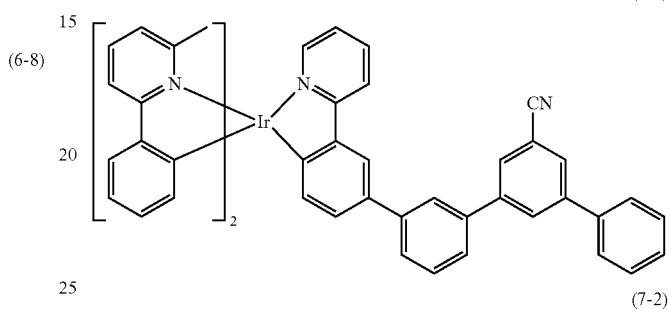
(7-2)
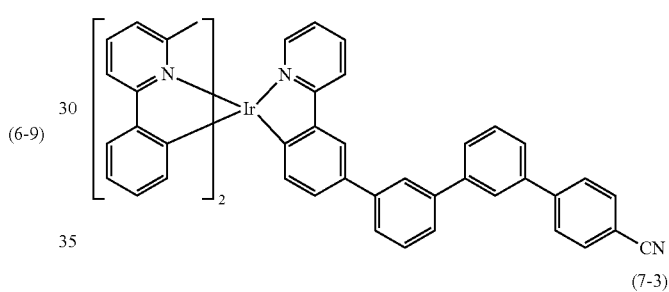
(7-3)
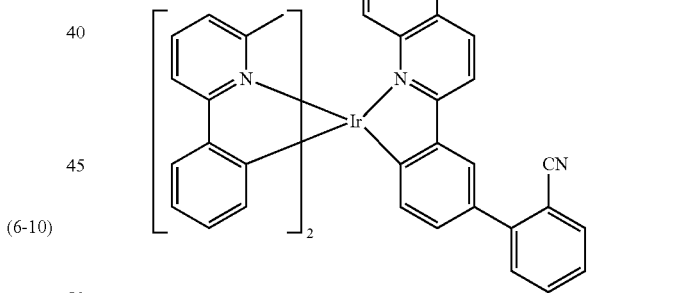
(7-4)
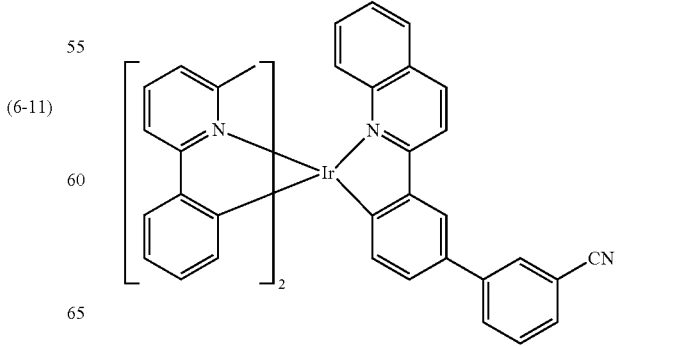

(7-5)
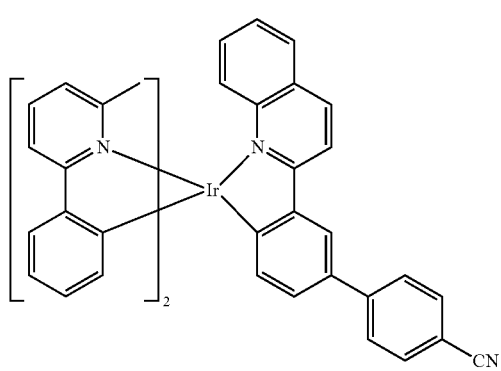
(7-6)
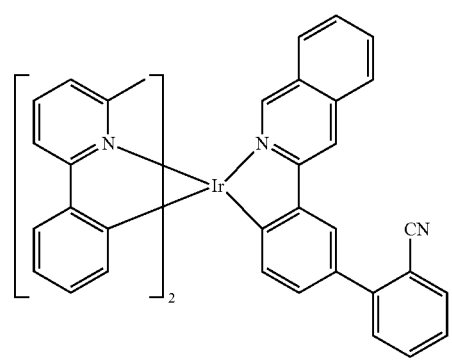
(7-7)
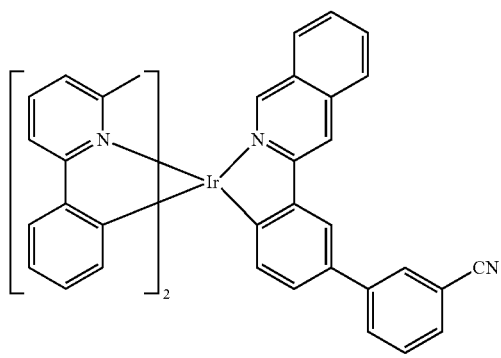
(7-8)
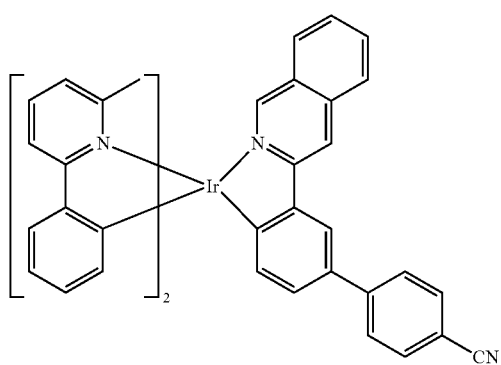
(7-9)
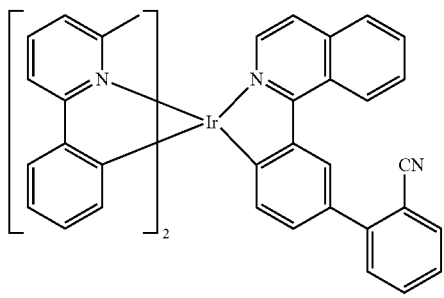
(7-10)
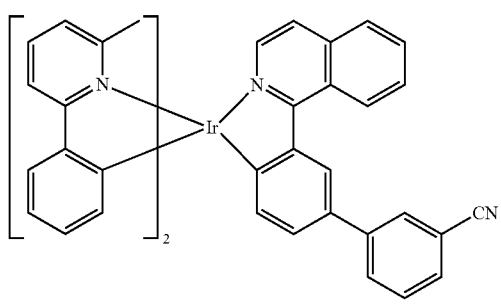
(7-11)
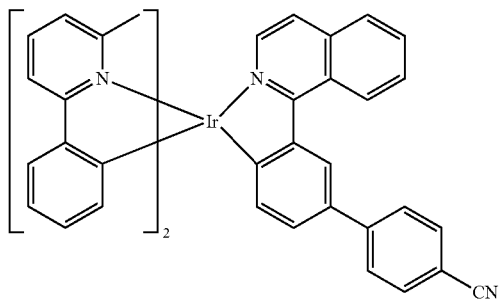
(7-12)
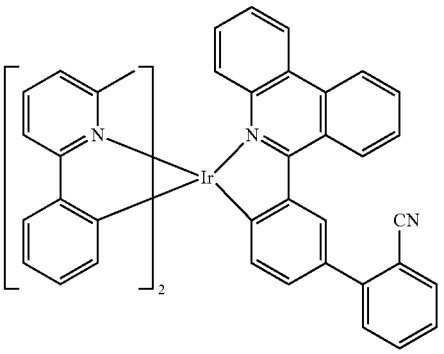
(7-13)
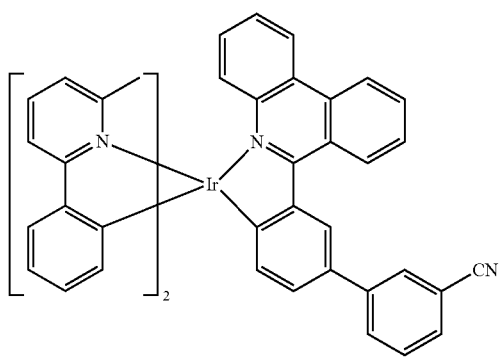

(7-14)
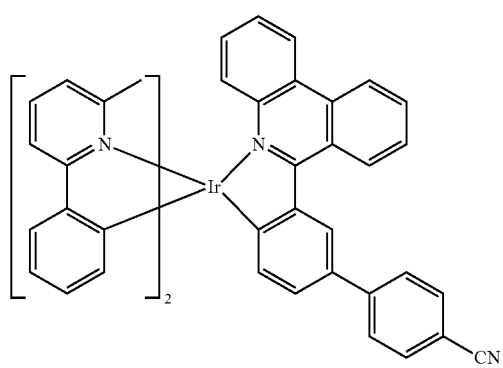
[Chem. 24]
(8-1)
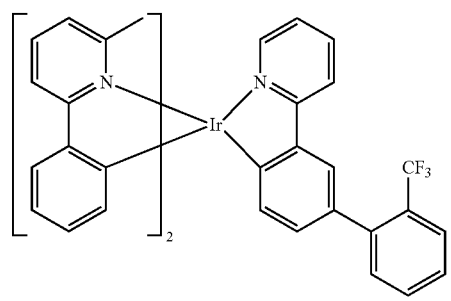
(8-2)
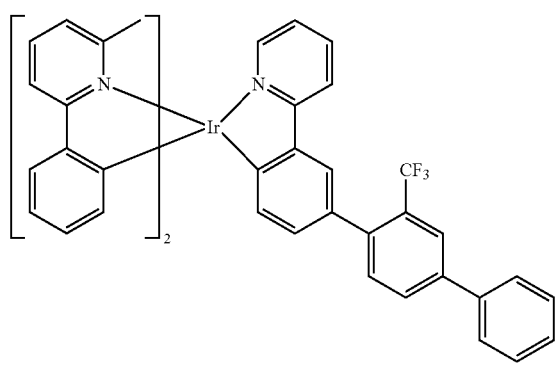
(8-3)
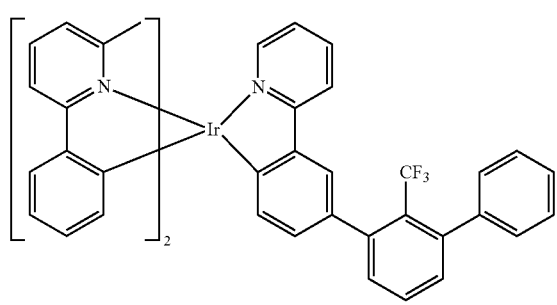
(8-4)
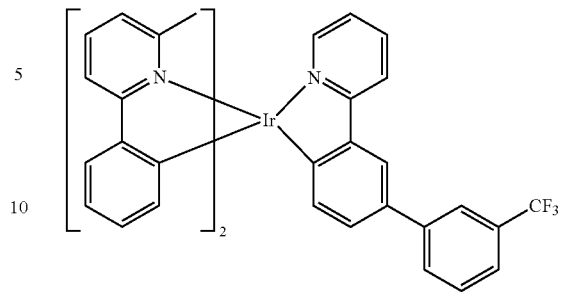
(8-5)
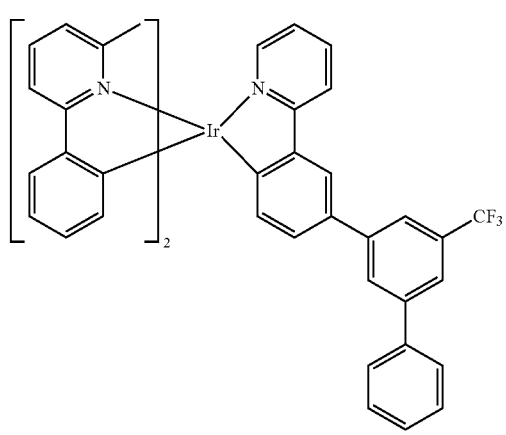
(8-6)
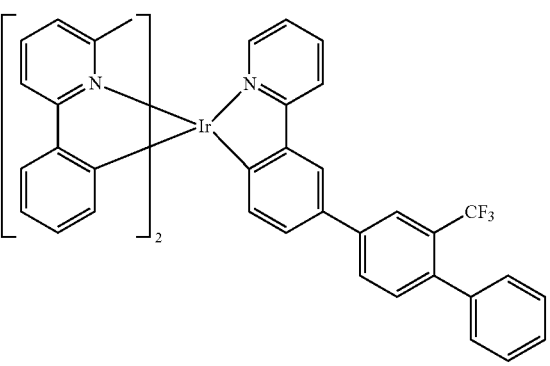
(8-7)
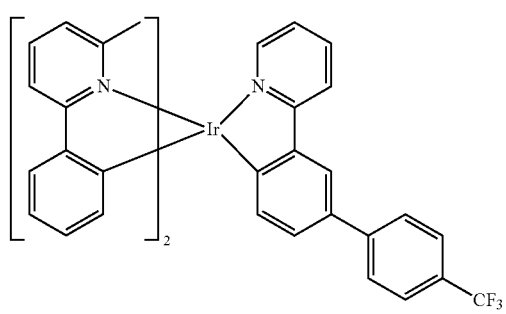

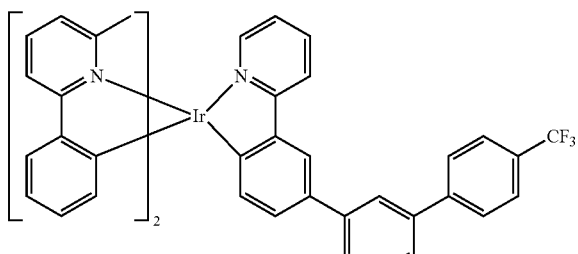
(8-8)

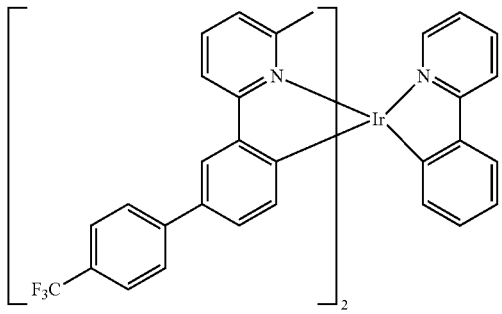
(8-12)

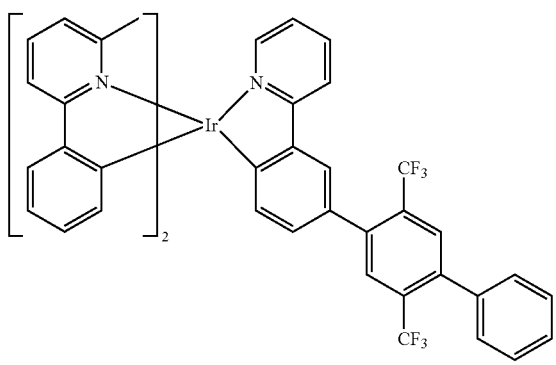
(8-9)

(8-10)

(8-11)

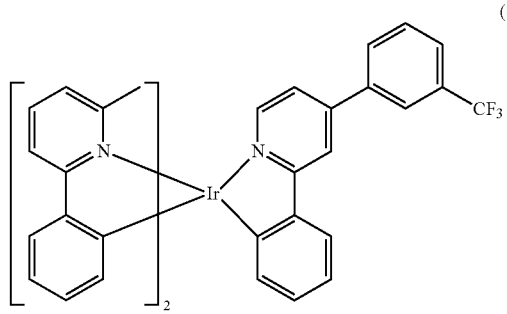

The compound represented by the general formula (1) can be synthesized by the method described in WO2009/073245, WO2010/028151, or the like.

The present invention also relates to a compound represented by the general formula (1) (further, a compound represented by the general formula (2), (3), (4), (5) or (6)).

The compound represented by the general formula (1) is not limited in terms of its uses and may be contained in any organic layers of the organic electroluminescent element, but the layer to which the compound represented by the general formula (1) is introduced is preferably a light emitting layer, and particularly preferably used as a light emitting material.

[Light Emitting Material Represented by General Formula (1)]

The present invention also relates to a light emitting material represented by the general formula (1).

The compound represented by the general formula (1) and the light emitting material of the present invention can be preferably used for organic electronic elements such as electrophotographs, organic transistors, organic photoelectric conversion elements (energy conversion applications, sensor applications, or the like), and organic electroluminescent elements, and particularly preferably used for organic electroluminescent elements.

[Thin Film Containing Compound Represented by General Formula (1)]

The present invention also relates to a thin film containing the compound represented by the general formula (1). The thin film of the present invention can be formed by any of dry film forming methods such as a deposition method and a sputtering method, and wet type film forming methods such as a transfer method and a printing method. The film thickness of the thin film can be any one, depending on the uses, but is preferably 0.1 nm to 1 mm, more preferably 0.5 nm to 1 μm, still more preferably 1 nm to 200 nm, and particularly preferably 1 nm to 100 nm.

[Organic Electroluminescent Element]

The organic electroluminescent element of the present invention is an organic electroluminescent element including a substrate, a pair of electrodes including an anode and a cathode, disposed on the substrate, and at least one organic layer including a light emitting layer, disposed between the electrodes, in which at least one kind of compound represented by the following general formula (1) is contained in any layer of the at least one organic layer. In view of the properties of the organic electroluminescent element, at least one electrode of a pair of electrodes, the anode and the cathode, is preferably transparent or semi-transparent.

Examples of the organic layer other than the light emitting layer include a hole injecting layer, a hole transporting layer, a blocking layer (a hole blocking layer, an exciton blocking layer, and the like), an electron transporting layer, and an electron injecting layer. These organic layers may be provided as a single layer or a plurality of layers, and in the case where a plurality of layers are provided, they may be formed of the same materials or different materials in every layer.

FIG. 1 shows one example of the configuration of the organic electroluminescent element according to the present invention. The organic electroluminescent element 10 in FIG. 1 has an organic layer including a light emitting layer 6 between a pair of electrodes (an anode 3 and a cathode 9) on a substrate 2. A hole injecting layer 4, a hole transporting layer 5, a light emitting layer 6, a hole blocking layer 7, and an electron transporting layer 8 are laminated in this order as the organic layer from the anode 3 side.

<Configuration of Organic Layer>

The layer configuration of the organic layer is not particularly limited and can be suitably selected depending on the use and purpose of the organic electroluminescent element. However, the organic layer is preferably formed on a transparent electrode or a semi-transparent electrode. In that case, the organic layer is formed on the entire surface or the partial surface of the transparent electrode or the semi-transparent electrode.

The shape, the size, the thickness, and the like of the organic layer are not particularly limited and can be suitably selected depending on the purpose.

Specific examples of the layer configuration include the following, but the present invention is not limited to these configurations.

Anode/light emitting layer/cathode

Anode/hole transporting layer/light emitting layer/cathode

Anode/light emitting layer/electron transporting layer/cathode

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode Anode/hole injecting layer/hole transporting layer/blocking layer/light emitting layer/blocking layer/electron transporting layer/electron injecting layer/cathode The element configuration, the substrate, the cathode, and the anode of the organic electroluminescent element are described in detail in, for example, JP-A-2008-270736, and the detailed descriptions in the publication can be applied to the present invention.

<Substrate>

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Anode>

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

<Cathode>

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic layer of the present invention will be described.

(Formation Organic Layer)

The respective organic layers in the organic electroluminescent element of the present invention can be suitably formed by any of dry film forming methods such as a deposition method and a sputtering method, and solution coating methods such as a transfer method, a printing method, a spin coating method, and a bar coating method.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting.

(Light Emitting Material)

In the present invention, at least one kind of light emitting material is preferably contained in the light emitting layer, and more preferably at least one kind of phosphorescent light emitting material in the light emitting layer. As the phosphorescent light emitting material, the compound represented by the general formula (1) is preferred.

In the present invention, a fluorescent light emitting material or a phosphorescent light emitting material different from the compound represented by the general formula (1) can be used, in addition to the compound represented by the general formula (1), as the light emitting material in the light emitting layer.

The fluorescent light emitting materials or the phosphorescent light emitting materials are described in detail in, for example, paragraph Nos. [0100] to [0164] of JP-A-2008-270736 and paragraph Nos. [0088] to [0090] of JP-A-2007-266458, and the detailed descriptions in these publications can be applied to the present invention.

Examples of the phosphorescent light emitting material which can be used in the present invention include phosphorescent light emitting materials described in Patent Literatures, for example, U.S. Pat. Nos. 6,303,238B1, 6,097,147, WO00/57676, WO00/70655, WO01/08230, WO01/39234A2, WO01/41512A1, WO02/02714A2, WO02/15645A1, WO02/44189A1, WO05/19373A2, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, with Ir complexes, Pt complexes, and Re complexes being particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, and chromaticity, Ir complexes and Pt complexes are particularly preferred, and Ir complexes are the most preferred.

These phosphorescent light emitting metal complex compounds are preferably contained in the light emitting layer, together with the compound represented by the general formula (1).

The compound represented by the general formula (1) in the light emitting layer is preferably contained in the amount of 0.1% by mass to 50% by mass, based on the total mass of the compound forming the light emitting layer, and from the viewpoints of durability and external quantum efficiency, it is preferably contained in the amount of 1% by mass to 50% by mass, and more preferably in the amount of 2% by mass to 40% by mass.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

The light emitting layer in the element of the present invention may be constituted of only the light emitting material or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

(Host Material)

The host material is a compound that usually plays a role in injecting or transporting charges in the light emitting layer and is also a compound which does not substantially emit light in itself. As used herein, the phrase "which does not substantially emit light" means that the amount of light emitting from the compound which does not substantially emit light is preferably 5% or less, more preferably 3% or less, and still more preferably 1% or less of the total amount of light emitting in the whole of the element.

Examples of the host material include compounds having the following structures in the partial structures: conductive high-molecular oligomers such as aromatic hydrocarbon, pyrrole, indole, carbazole, azaindole, azacarbazole, triazole, oxazole, oxadiazole, pyrazole, imidazole, thiophene, dibenzothiophene, polyarylalkane, pyrazoline, pyrazolone, phenylenediamine, arylamine, amino-substituted chalcone, styrylanthracene, hydrazone, stilbene, silazane, aromatic tertiary amine compounds, styrylamine compounds, porphyrin-based compounds, polysilane-based compounds, poly(N-vinylcarbazole), aniline-based copolymers, thiophene oligomers, and polythiophene, organic silanes, carbon films, pyridine, pyrimidine, triazine, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring).

The organic electroluminescent element of the present invention preferably contains the compound represented by the general formula (1) and a compound having a cyano group, and more preferably contains the compound represented by the general formula (1) as the light emitting material and a compound having a cyano group as a host material.

Preferred examples of the host material include carbazole derivatives, dibenzofuran derivatives, dibenzothiophene derivatives, and triphenylene derivatives.

As the dibenzofuran derivatives and the dibenzothiophene derivatives, the compounds represented by the following general formula (S-1) are preferred.

[Chem. 25]

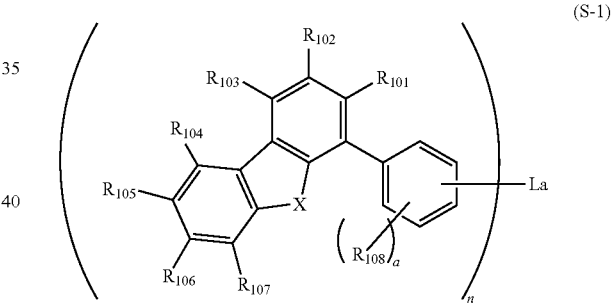

In the general formula (S-1), X represents an oxygen atom or a sulfur atom. $R_{101}$ to $R_{107}$ each independently represent a hydrogen atom or a substituent, and $R_{108}$ represents a substituent. a represents an integer of 0 to 4. n represents an integer of 1 or more. La represents an n-valent aromatic hydrocarbon groups and may have a substituent.

X represents an oxygen atom or a sulfur atom.

Examples of the substituents represented by $R_{101}$ to $R_{108}$ each independently represent the Substituent Group A. The substituents may further have a substituent, and examples of the additional substituent include the groups selected from the Substituent Group A.

As $R_{101}$ to $R_{107}$, a hydrogen atom, an alkyl group, a cyano group, or an aryl group is preferred.

n represents an integer of 1 or more, preferably 1 to 3, more preferably 1 or 2, and still more preferably 2. In the case where n represents an integer of 2 or more, each of the X, $R_{101}$ to $R_{108}$, and a which are present in plural in the general formula (S-1) may be different from each other.

La represents an n-valent aromatic hydrocarbon group, examples of the aromatic hydrocarbon group include a phenyl group, a fluorenyl group, a naphthyl group, and a triphenylenyl group, but a group formed by the linkage of 1 to 3 benzene rings being preferred, which includes L1 to L15 described as the specific examples of L in the general formula (A).

La may further have a substituent. Examples of the substituent in the case where La has an additional substituent include the Substituent Group A; preferably a cyano group, a substituted or unsubstituted aryl group (a phenyl group or a biphenyl group), a heterocyclic group (preferably a nitrogen-containing aromatic heterocyclic group, and more preferably a carbazolyl group, an acridinyl group, and the like), or a diarylamino group (as the aryl group, a phenyl group is preferred, and the aryl groups may be bonded to each other or the aryl group may be bonded to La to form a ring); more preferably a cyano group or a substituted or unsubstituted aryl group (a phenyl group or a biphenyl group); still more preferably a cyano group or a phenyl group; and particularly preferably a cyano group. The substituent in the case where the aryl group has a substituent is preferably a cyano group or a phenyl group.

From the viewpoint of durability, at least one cyano group is preferably contained in the general formula (S-1). Further, from the viewpoint of the chemical stability of charge transporting molecules, it is preferable that a cyano group be only a substituent of $R_{108}$ or La, and from the same viewpoint, it is preferable that a cyano group be only a substituent of La.

Specific examples of the compound represented by general formula (S-1) are listed below, but are not limited thereto.

[Chem. 26]

Compound 1A-1

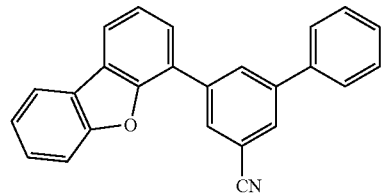

Compound 1A-2

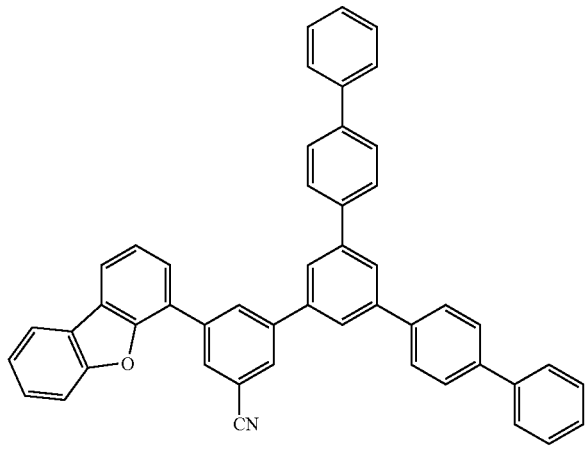

Compound 1A-3

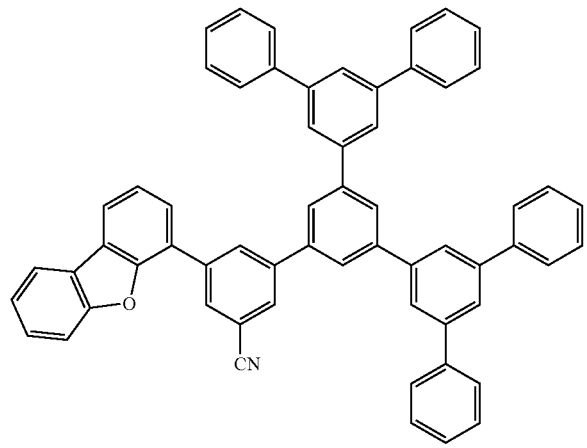

Compound 1A-4

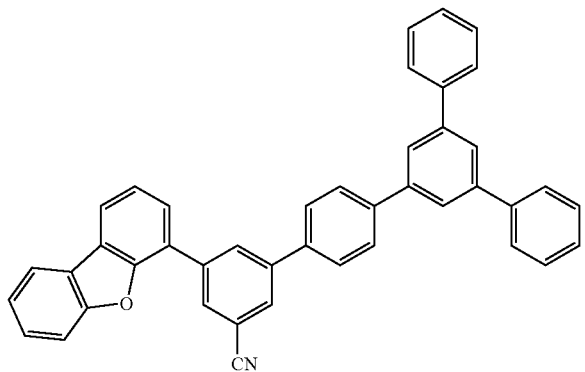

Compound 1A-5

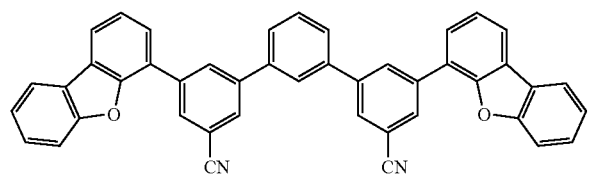

Compound 1A-6

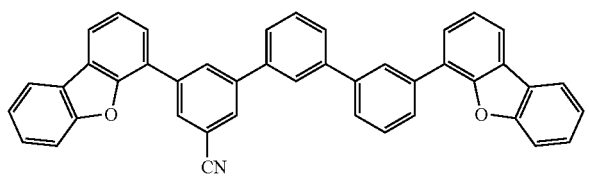

-continued
Compound 1A-7
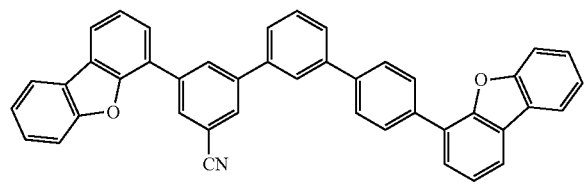
Compound 1A-8
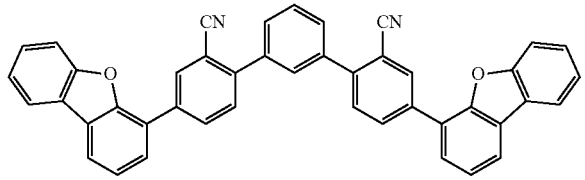
Compound 1A-9
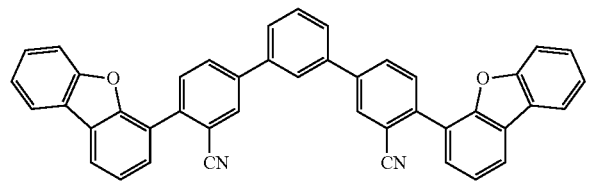
Compound 1A-10
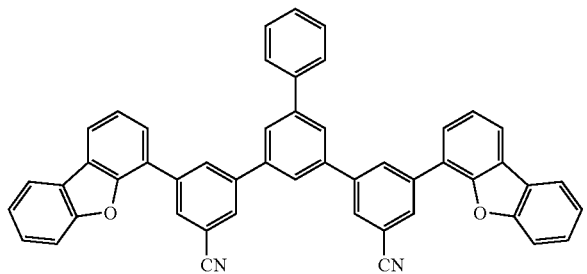
Compound 1A-11
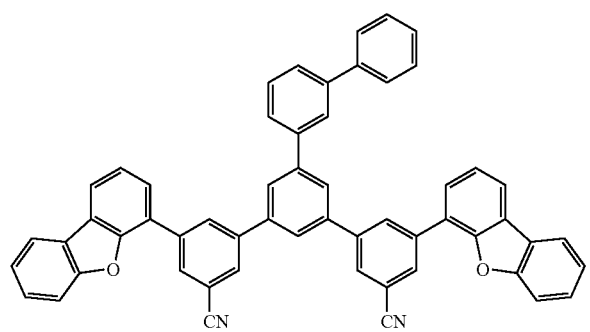
Compound 1A-12
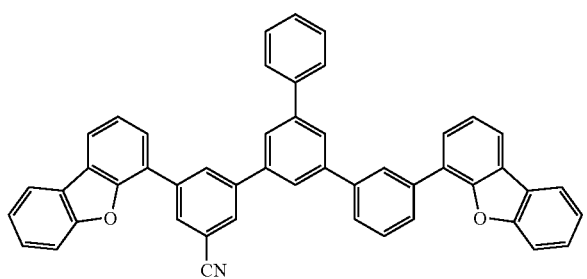
Compound 1A-13
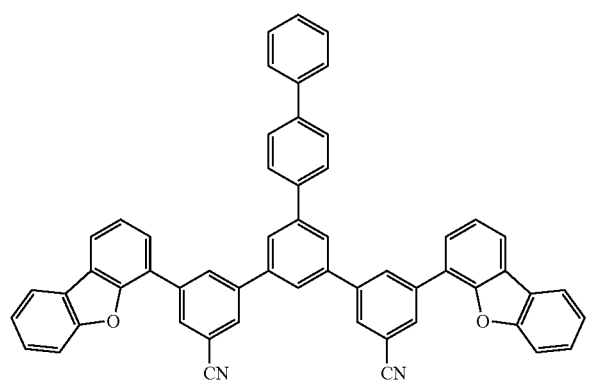
Compound 1A-14
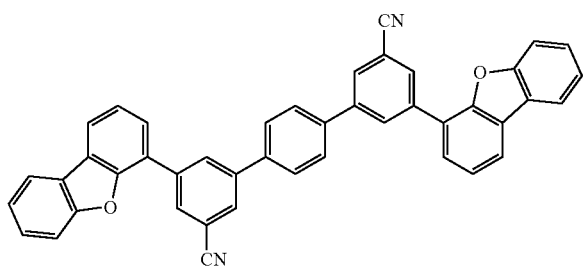
Compound 1A-15
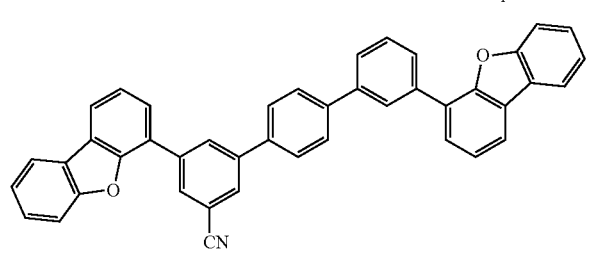
Compound 1A-16
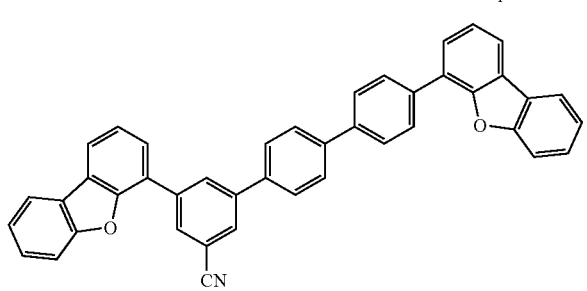

Compound 1A-17
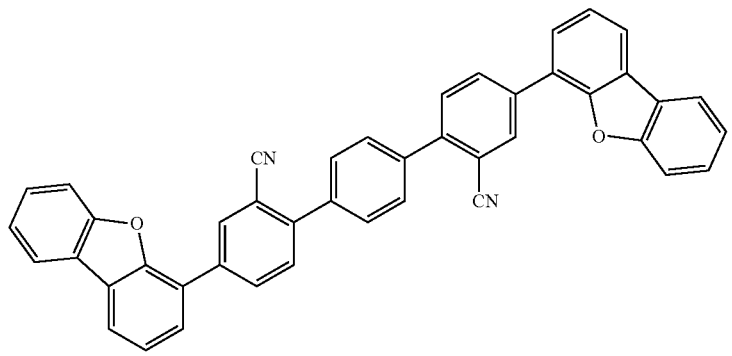
[Chem. 27]
compound 1A-32
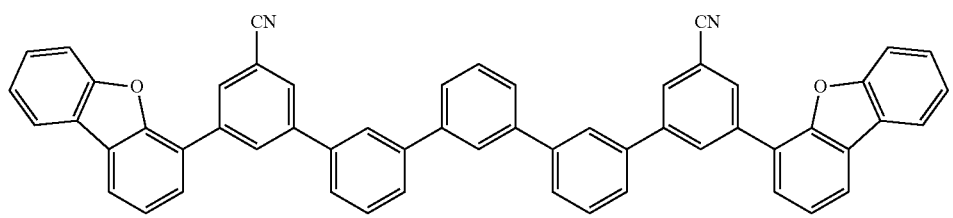
compound 1A-33
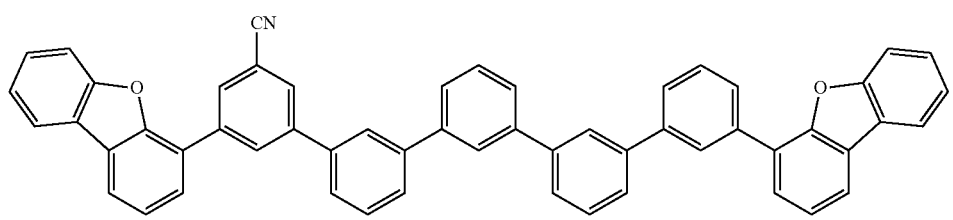
compound 1A-34
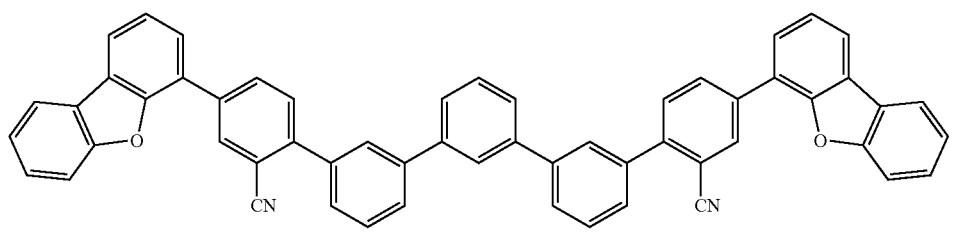
compound 1A-35
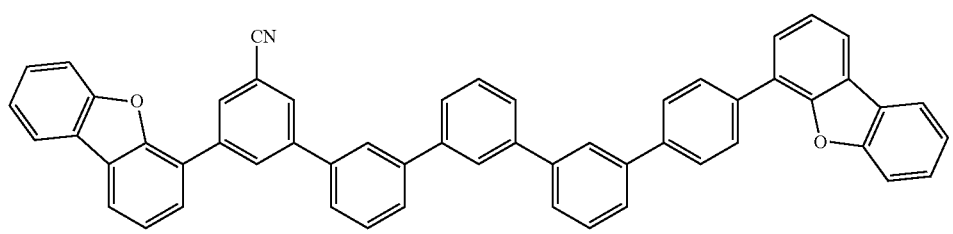
compound 1A-36
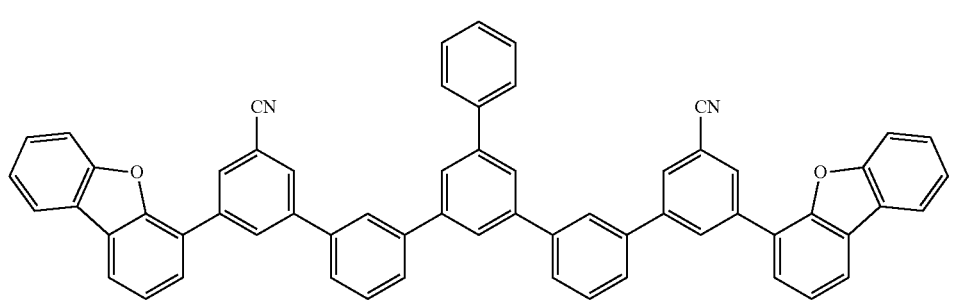

-continued
compound 1A-37
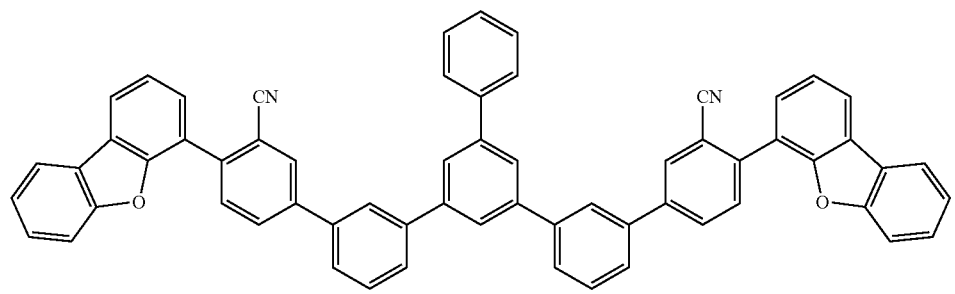
compound 1A-38
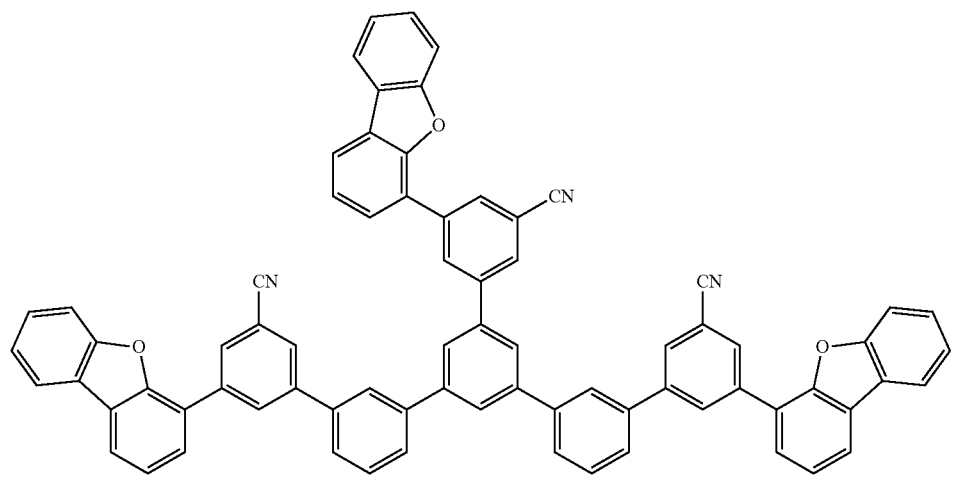
compound 1A-39
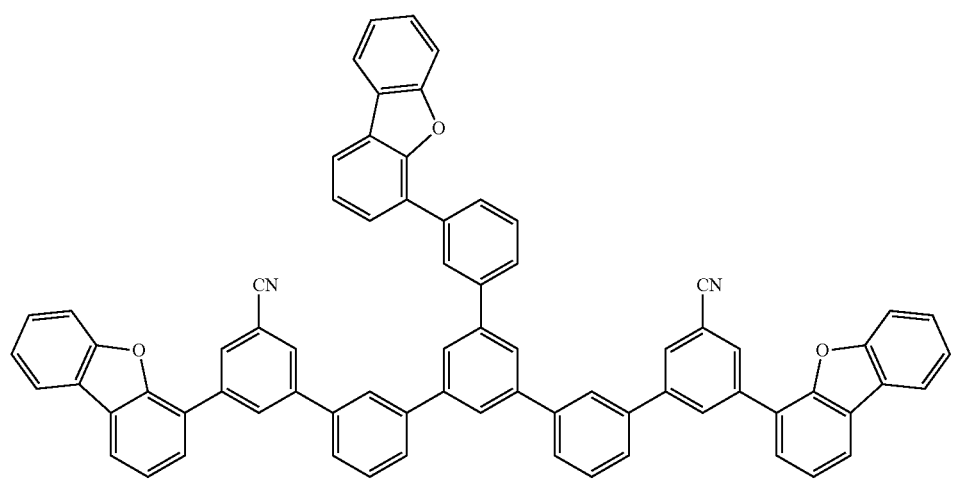

copound 1A-40
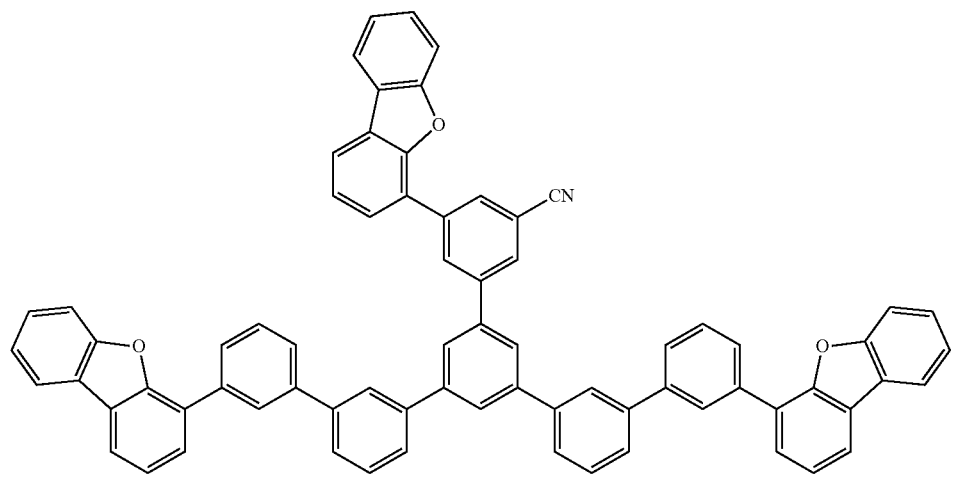
compound 1A-41
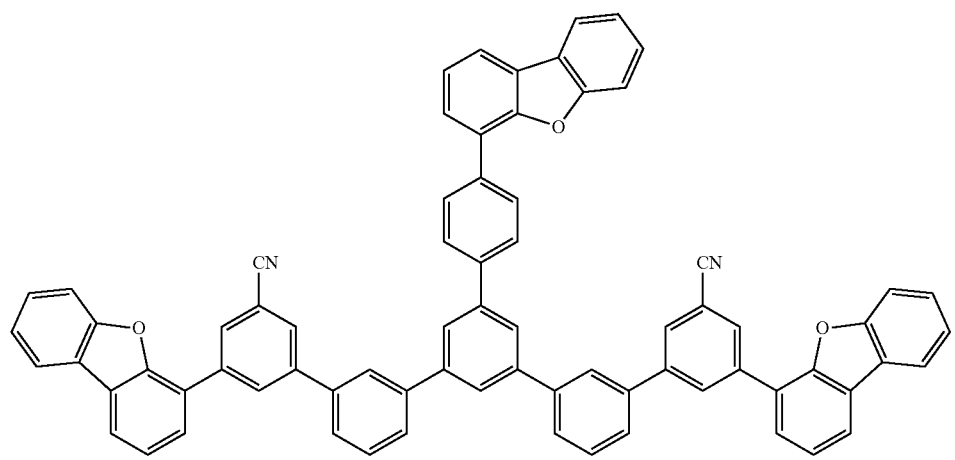
compound 1A-42
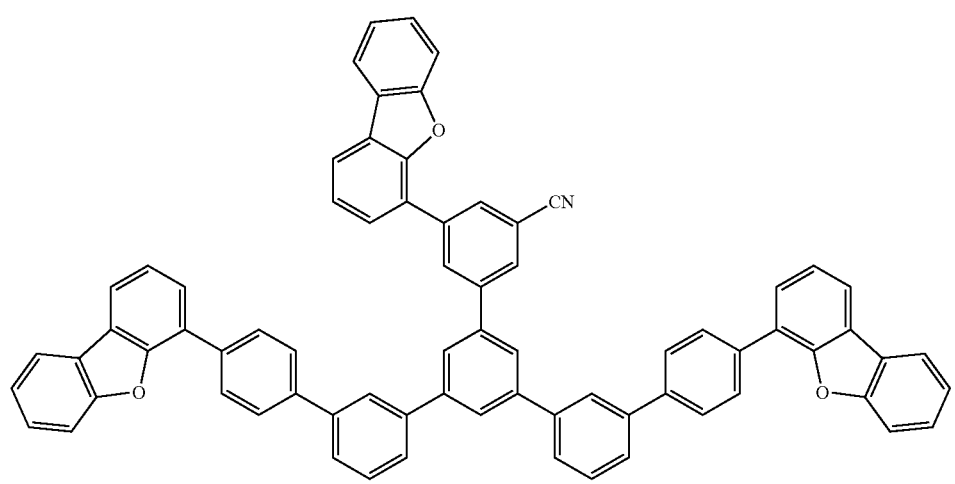

-continued
compound 1A-43
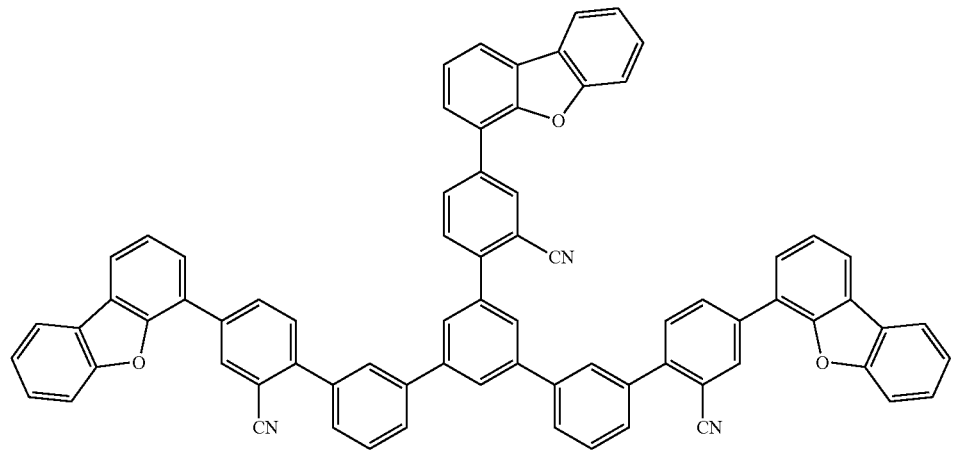
compound 1A-44
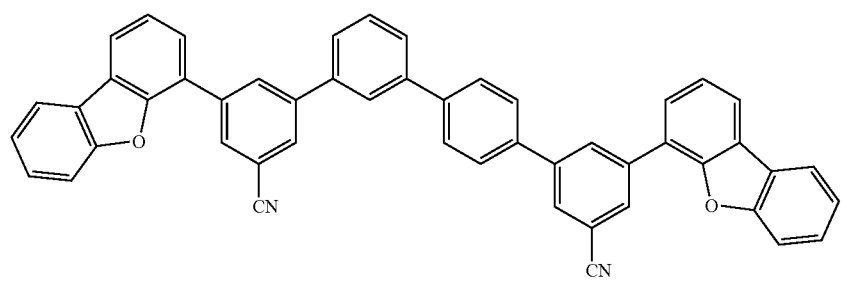
compound 1A-45
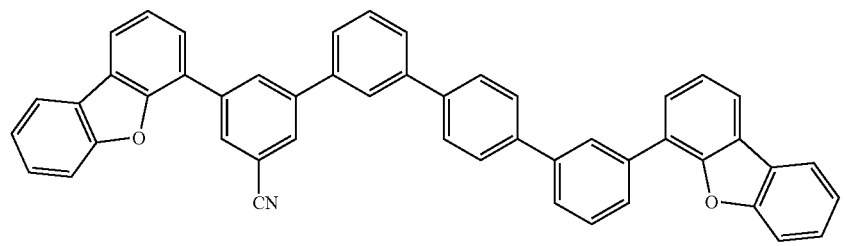
compound 1A-46
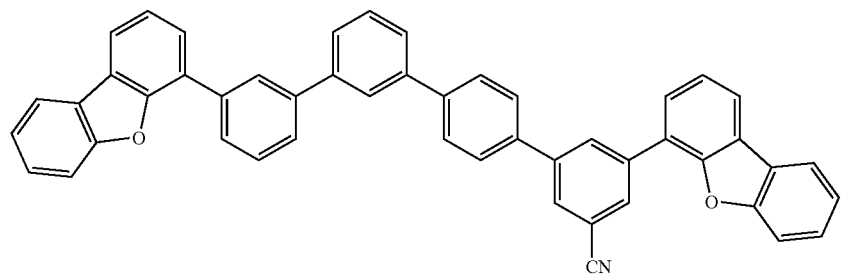
compound 1A-47
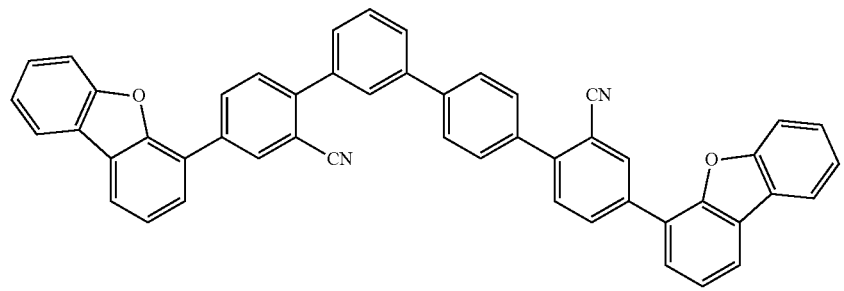

-continued
compound 1A-48
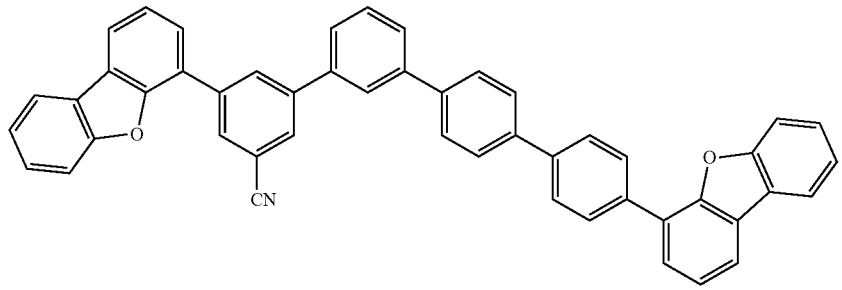
Compound 1A-49
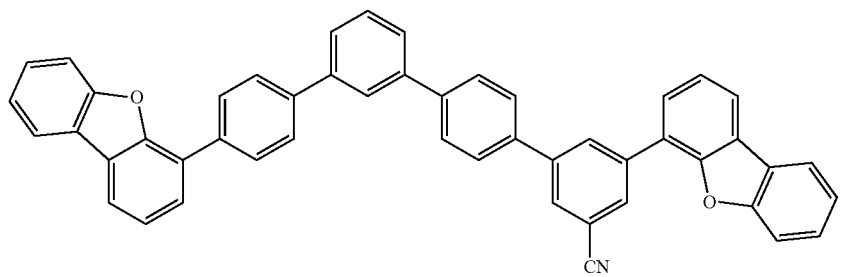
[Chem. 28]
Compound 2A-1
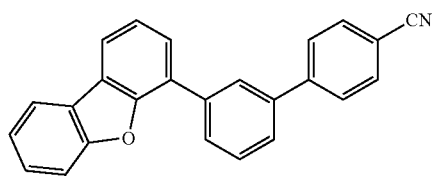
Compound 2A-2
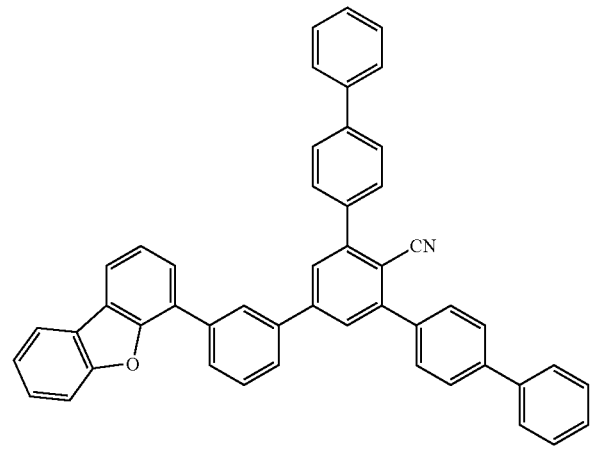
Compound 2A-3
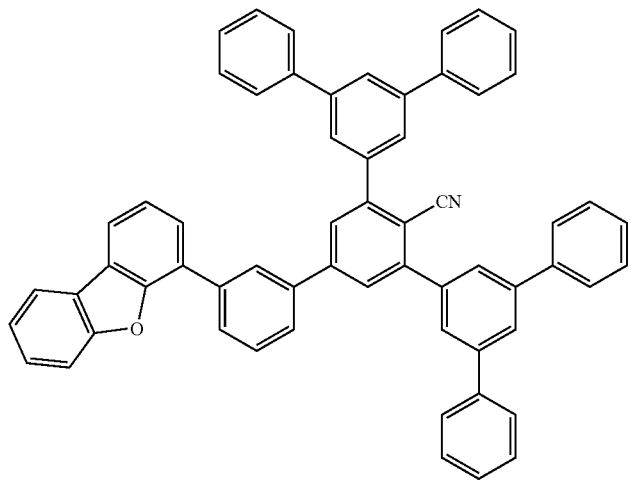

-continued
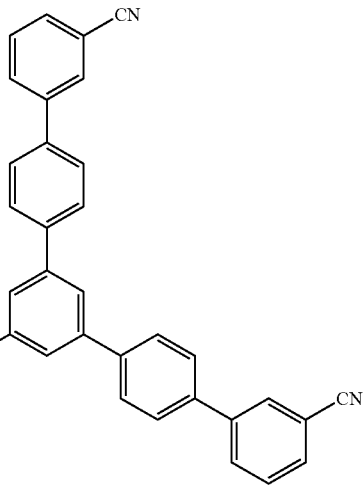
Compound 2A-4
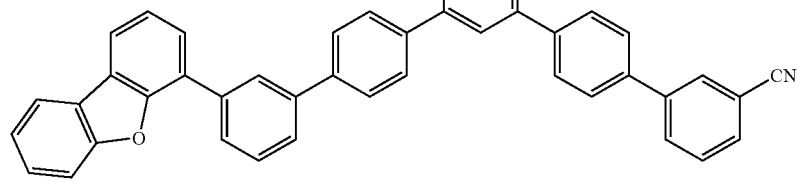
Compound 2A-5
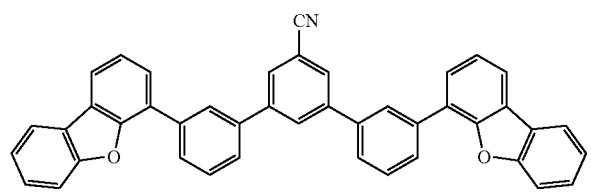
Compound 2A-6
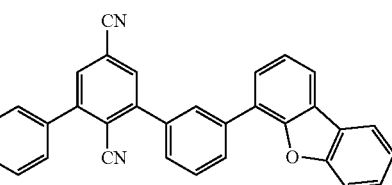
Compound 2A-7
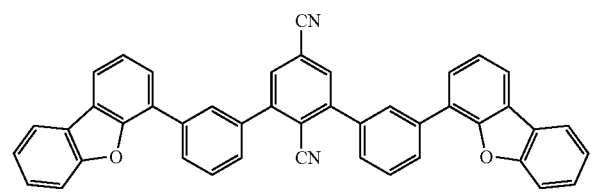
Compound 2A-8
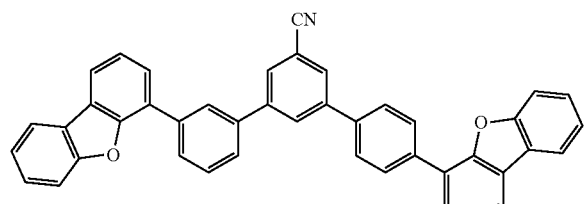
Compound 2A-9
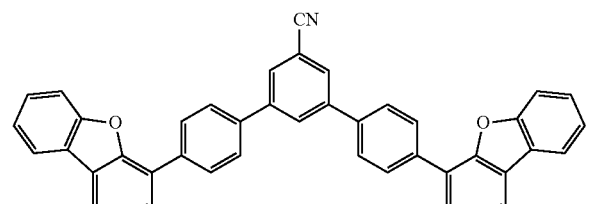
Compound 2A-10
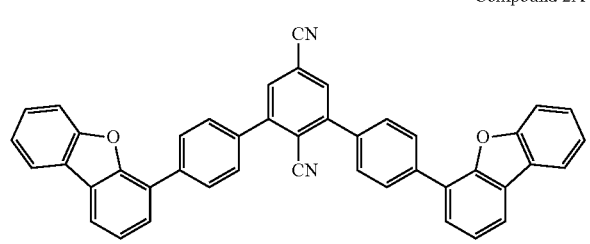
Compound 2A-11
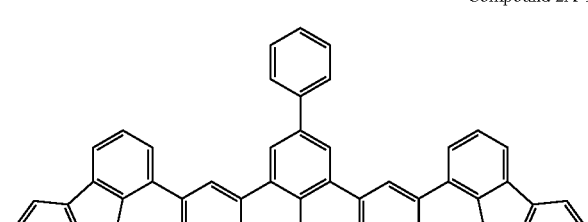
Compound 2A-12
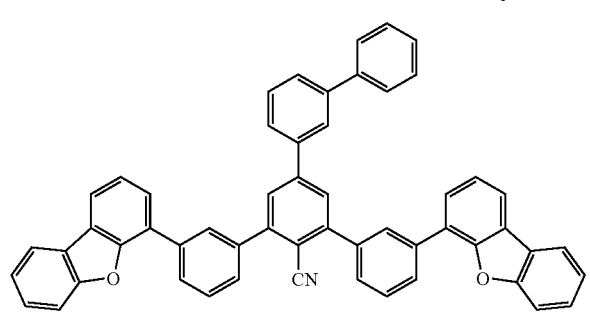
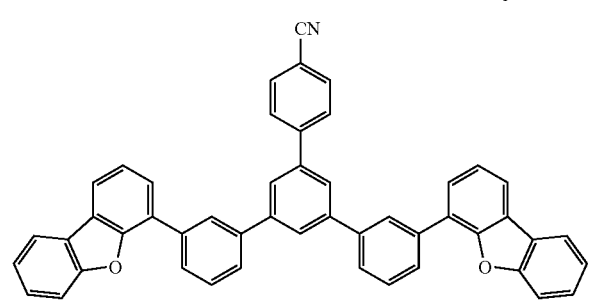

-continued
Compound 2A-13
Compound 2A-14
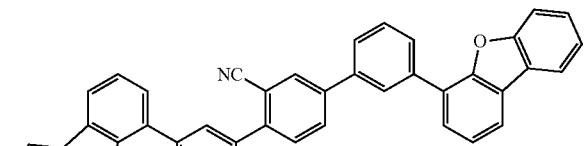
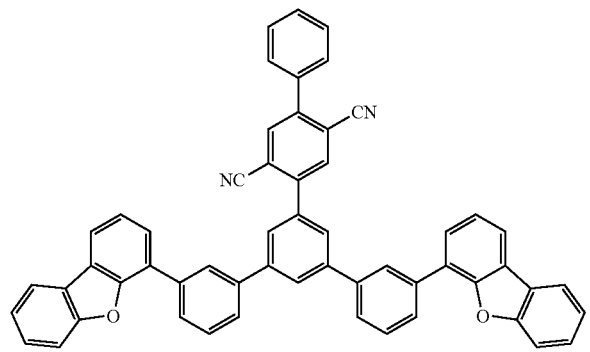
Compound 2A-15
Compound 2A-16
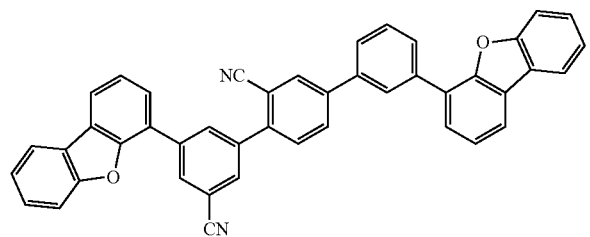
Compound 2A-17
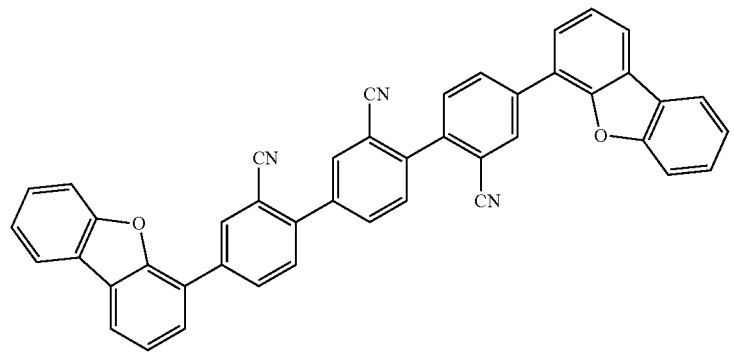
[Chem. 29]
Compound 1B-1
Compound 1B-2
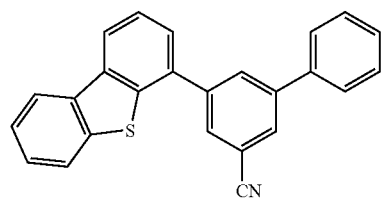
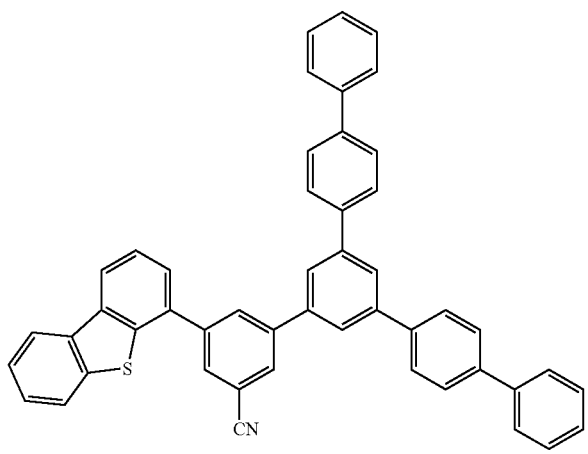

-continued
Compound 1B-3
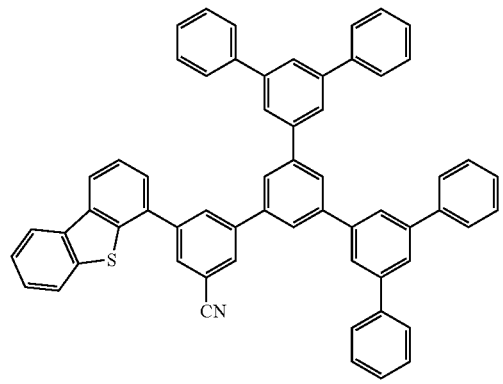
Compound 1B-4
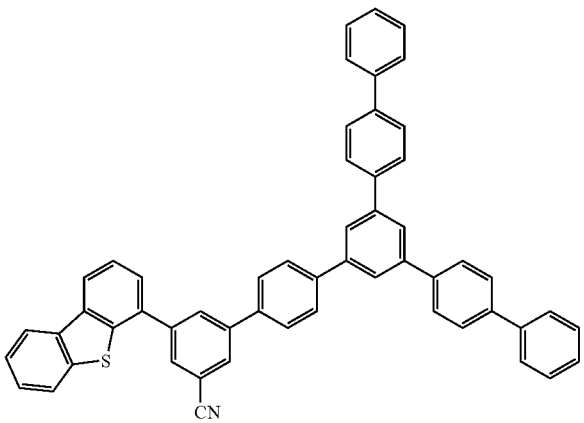
Compound 1B-5
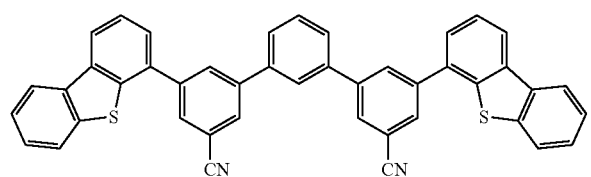
Compound 1B-6
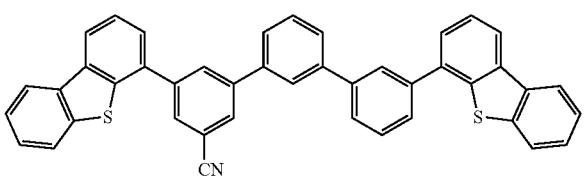
Compound 1B-7
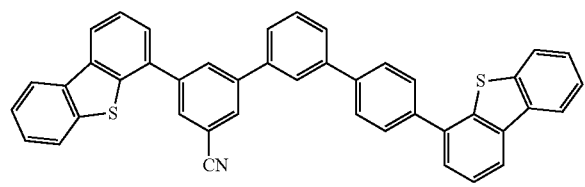
Compound 1B-8
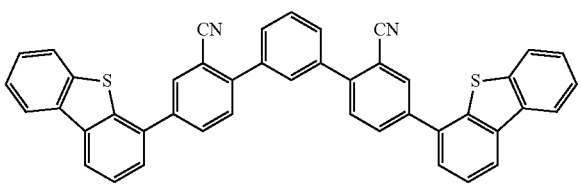
Compound 1B-9
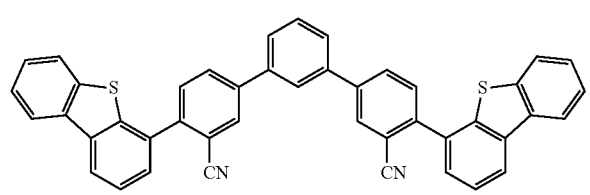
Compound 1B-10
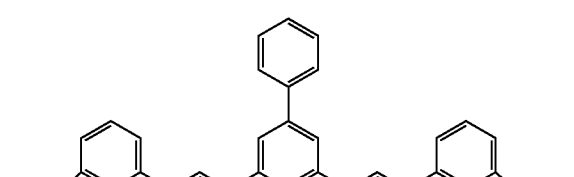
Compound 1B-11
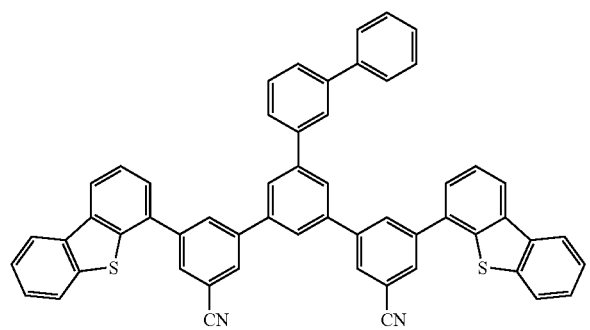
Compound 1B-12
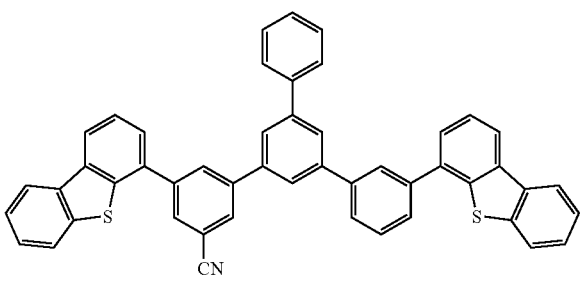

Compound 1B-13

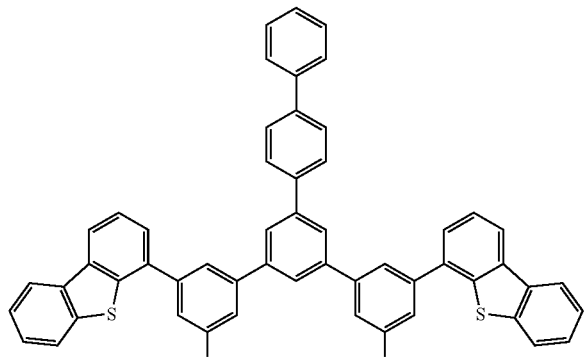

Compound 1B-14

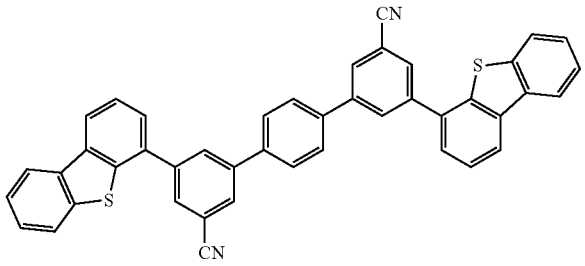

Compound 1B-15

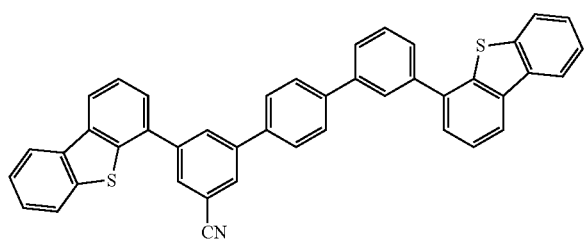

Compound 1B-16

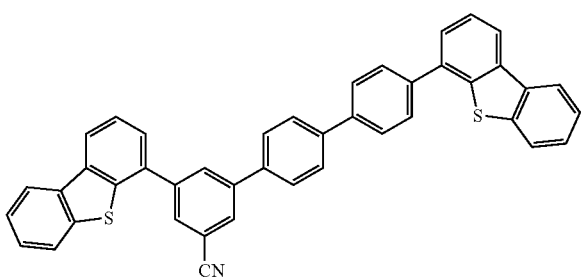

Compound 1B-17

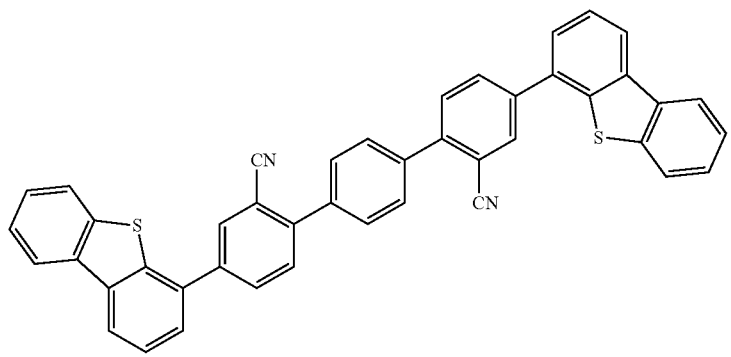

Examples of the triphenylene derivative include a compound represented by the following general formula (Tp-1).

[Chem. 30]

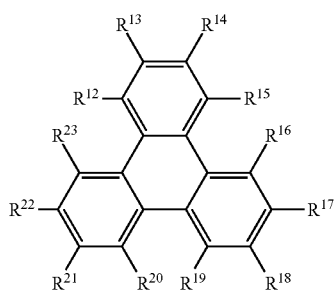

(Tp-1)

In the general formula (Tp-1), $R^{12}$ to $R^{23}$ each independently represent a hydrogen atom, an alkyl group, or a phenyl group which may be substituted with an alkyl group, a phenyl group, a fluorenyl group, a naphthyl group, or a triphenylenyl group, a fluorenyl group, a naphthyl group, or a triphenylenyl group. However, there is no case where $R^{12}$ to $R^{23}$ are all hydrogen atoms.

Examples of the alkyl group represented by $R^{12}$ to $R^{23}$ include a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group, each of which is substituted or unsubstituted; preferably a methyl group, an ethyl group, an isopropyl group, a tert-butyl group, and a cyclohexyl group; and more preferably a methyl group, an ethyl group, and a tert-butyl group.

As $R^{12}$ to $R^{23}$, an alkyl group having 1 to 4 carbon atoms, a phenyl group, a fluorenyl group, a naphthyl group, or a triphenylenyl group, which may be substituted with an alkyl group having 1 to 4 carbon atoms, a phenyl group, a fluorenyl group, a naphthyl group, or a triphenylenyl group (there may be further substituted with an alkyl group, a phenyl group, a fluorenyl group, a naphthyl group, or a triphenylenyl group) is still more preferred; and benzene rings which may be substituted with a phenyl group, a fluorenyl group, a naphthyl group, or a triphenylenyl group (these may be further substituted with an alkyl group, a phenyl group, a fluorenyl group, a naphthyl group, or a triphenylenyl group) are particularly preferred.

The total number of the aryl rings in the general formula (Tp-1) is preferably from 2 to 8, and preferably from 3 to 5. With the number in these ranges, a good amorphous thin film can be formed, and thus, the solubility in a solvent, and the sublimation and deposition suitability become better.

$R^{12}$ to $R^{23}$ each independently have a total number of carbon atoms of preferably from 20 to 50, and more preferably from 20 to 36. Within these ranges, an amorphous thin film with good quality can be formed and thus, the solubility in a solvent, and the sublimation and deposition suitability become better.

Hereinbelow, specific examples of the compound represented by the general formula (Tp-1) are shown below, but are not limited thereto.

[Chem. 31]

TpH-1

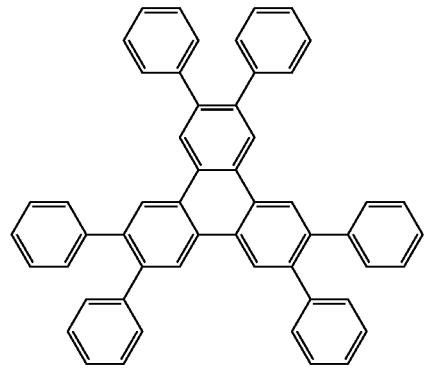

TpH-2

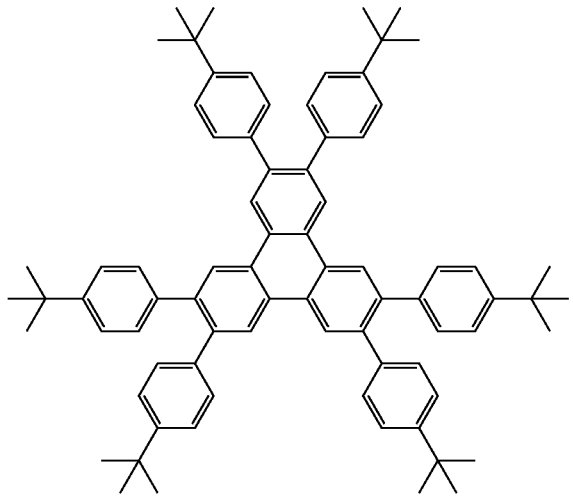

TpH-3

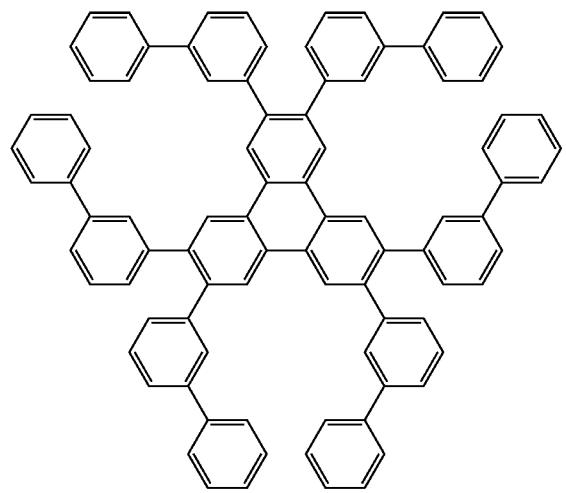

TpH-4

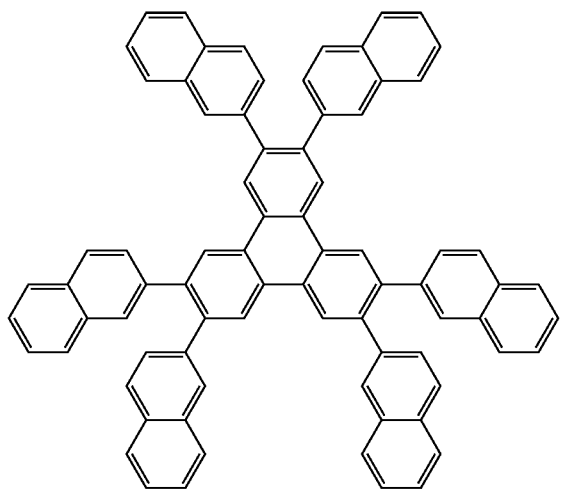

-continued
TpH-5
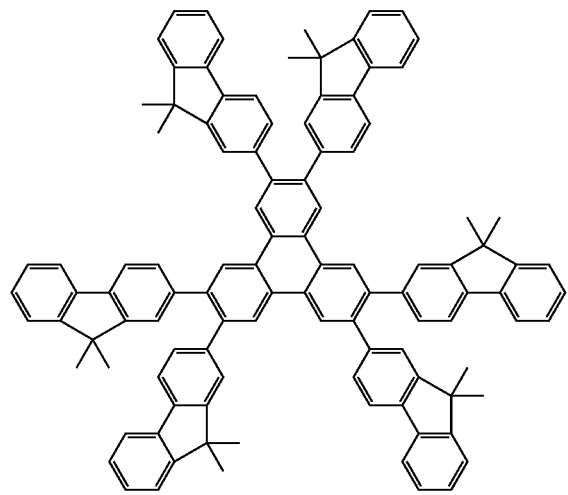
TpH-6
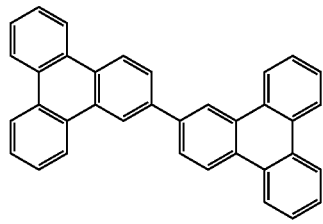
TpH-7
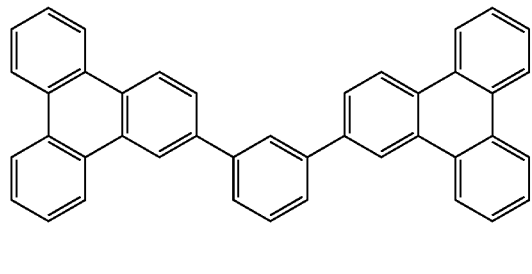
TpH-8
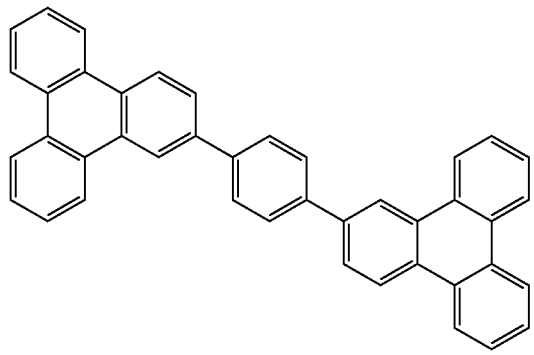
TpH-9
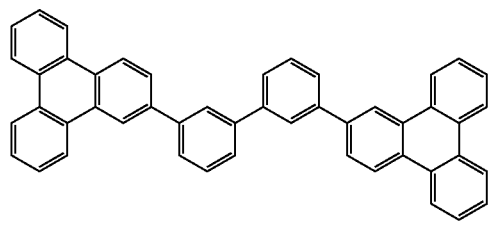
TpH-10
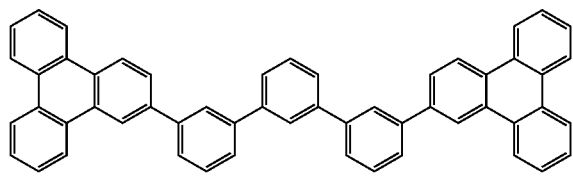
TpH-11
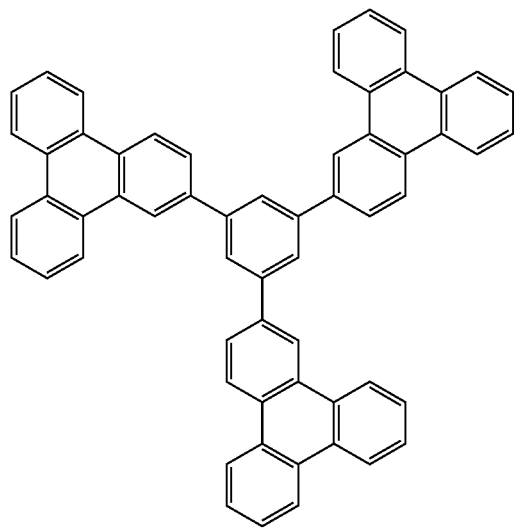
TpH-12
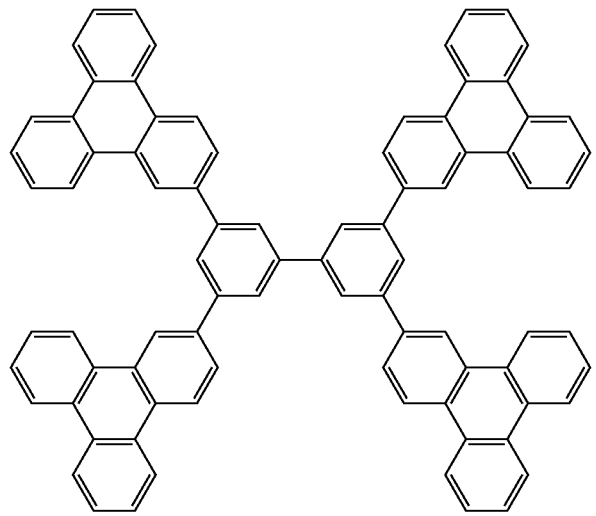

[Chem. 32]
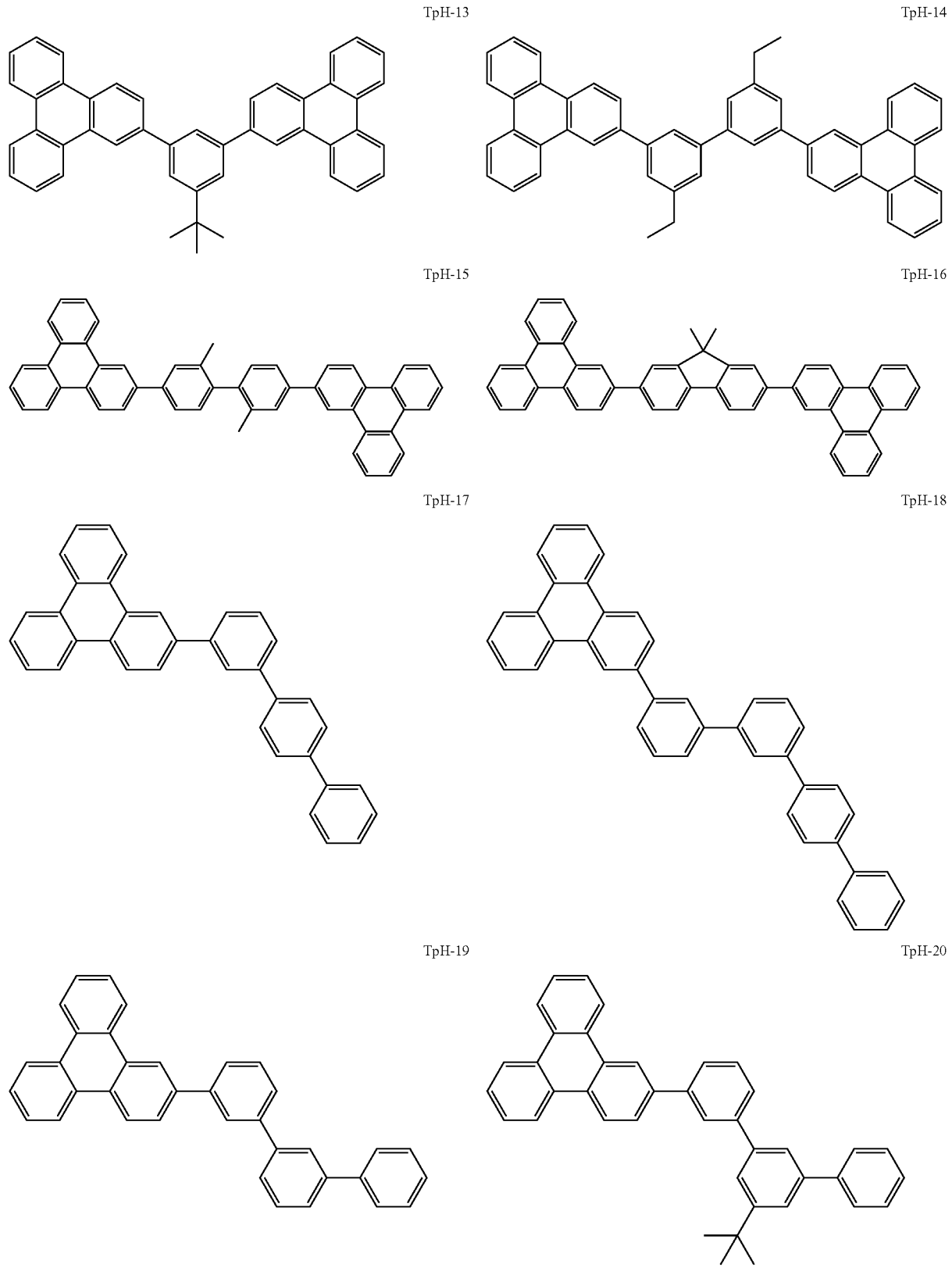

TpH-21
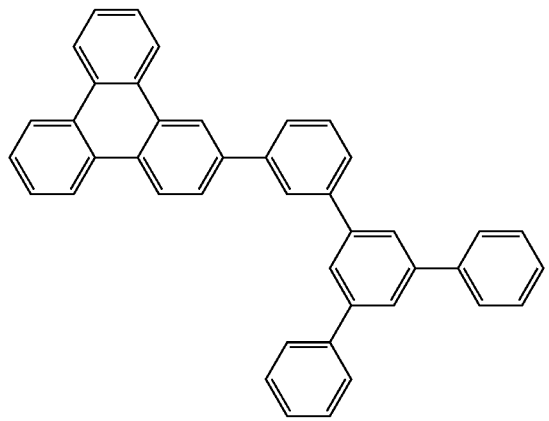

TpH-22
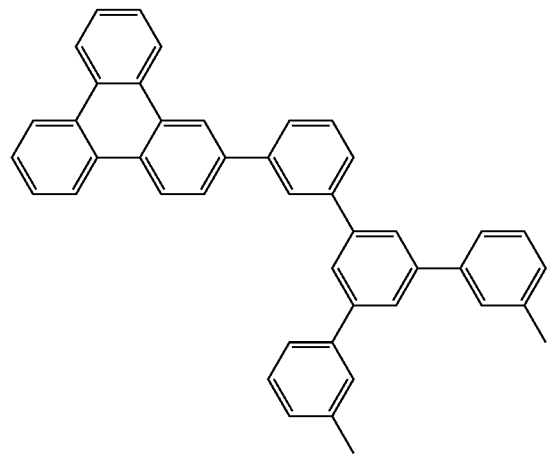

TpH-23
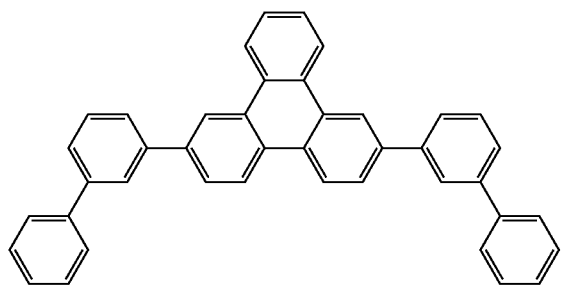

TpH-24
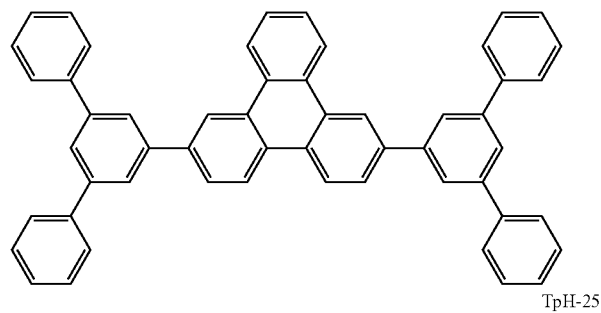

TpH-25
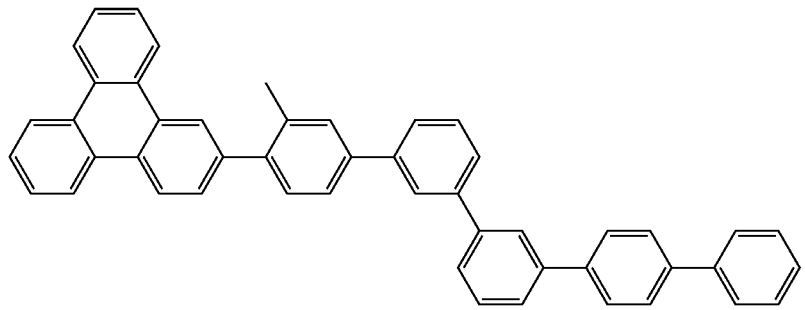

The compounds can be synthesized by the methods described in WO05/013388, WO06/130598, WO09/021, 107, US2009/0009065, WO09/008,311, and WO04/018587.

(Charge Transporting Layer)

The charge transporting layer refers to a layer in which charges move when voltage is applied to the organic electroluminescent element. Specific examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, which is formed by a coating method, it becomes possible to prepare an organic electroluminescent element with low cost and high efficiency.

(Hole Injecting Layer and Hole Transporting Layer)

The hole injecting layer and the hole transporting layer are layers having a function of receiving holes from the anode or the anode side and transporting them to the cathode side.

In addition, with respect to the hole injecting layer and the hole transporting layer, the detailed descriptions in paragraph Nos. [0165] to [0167] of JP-A-2008-270736 can be applied to the present invention.

Further, the following compounds can also be preferably used as a hole injecting material.

[Chem. 33]

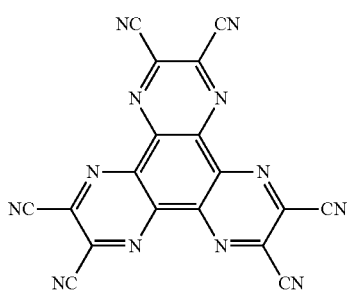

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include tetracyanoquinodimethane (TCNQ), tetrafluorotetracyanoquinodimethane ($F_4$-TCNQ), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer.

(Charge Generating Layer)

As the compound which forms the charge generating layer, the same compounds as the compounds used in the hole injecting layer can be used.

(Electron Injecting Layer and Electron Transporting Layer)

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, the compound represented by the general formula (1) of the present invention can be used. The layer preferably contains, as the other materials, aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, and the like.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one kind or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(Hole Blocking Layer)

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $T_1$ energy of the organic compound in the film state constituting the hole blocking layer prevents the energy movement of excitons produced in the light emitting layer, and thus, does not lower the luminous efficiency, it is preferably higher than the $T_1$ energy of the light emitting material.

Examples of the organic compounds constituting the hole blocking layer include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 5 nm to 200 nm, and still more preferably from 10 nm to 100 nm.

The hole blocking layer may have either a single layer structure composed of one kind or two or more kinds of the above-described materials or a multilayer structure composed of a plurality of layers having the same composition or different compositions.

(Electron Blocking Layer)

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

In order that the $T_1$ energy of the organic compound in the film state constituting the electron blocking layer prevents the energy movement of excitons produced in the light emitting layer, and thus, does not lower the luminous efficiency, it is preferably higher than the $T_1$ energy of the light emitting material.

As the organic compound constituting the electron blocking layer, for example, those exemplified above as the hole transporting material can be used.

The thickness of the electron blocking layer is preferably from 1 nm to 500 nm, more preferably from 5 nm to 200 nm, and still more preferably from 10 nm to 100 nm.

The electron blocking layer may have either a single layer structure composed of one kind or two or more kinds of from the above-described materials or a multilayer structure composed of a plurality of layers having the same composition or different compositions.

[Compound Represented by General Formula (HT-1)]

In the organic electroluminescent element of the present invention, it is preferable that the pair of electrodes include an anode, and at least one organic layer be included between the light emitting layer and the anode, and it is also preferable that the organic layer contains at least one kind of a compound represented by the following general formula (HT-1). The triarylamine compound represented by the following general formula (HT-1) is preferably used as a hole transporting material.

[Chem. 34]

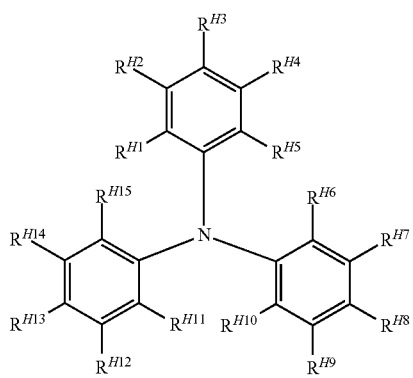

General formula (HT-1)

In the general formula (HT-1), $R^{H1}$ to $R^{H15}$ each independently represent a hydrogen atom or a substituent.

In the case where $R^{H1}$ to $R^{H15}$ each represent a substituent, examples of the substituent include the substituents selected from the Substituent Group A, among which an alkyl group, an aryl group, an amino group, or a heteroaryl group is preferred, and an alkyl group, an aryl group, or an arylamino group is more preferred. The substituent may be further substituted, and the specific examples and the preferred range of the additional substituent are the same as in the case where $R^{H1}$ to $R^{H15}$ each represent a substituent.

At least two adjacent groups out of $R^{H1}$ to $R^{H15}$ may form a ring via a single bond or a linking group. Preferred examples of the linking group include an oxygen atom, a sulfur atom, and an alkylene group.

From the viewpoint of heat resistance and durability, it is preferable that at least one of $R^{H1}$ to $R^{H5}$ and at least one of $R^{H6}$ to $R^{H10}$ be each an aryl group. Specific examples of the compound represented by the general formula (HT-1) are shown below, but are not limited thereto.

[Chem. 35]

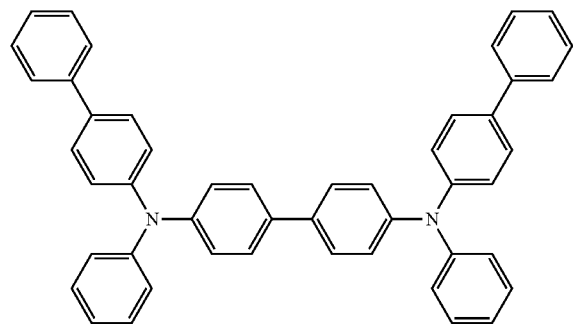

(HTL-1)

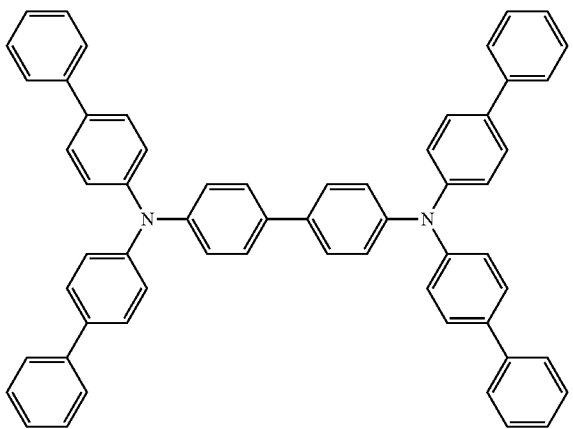

(HTL-2)

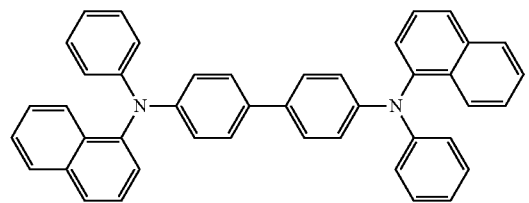

(HTL-3)

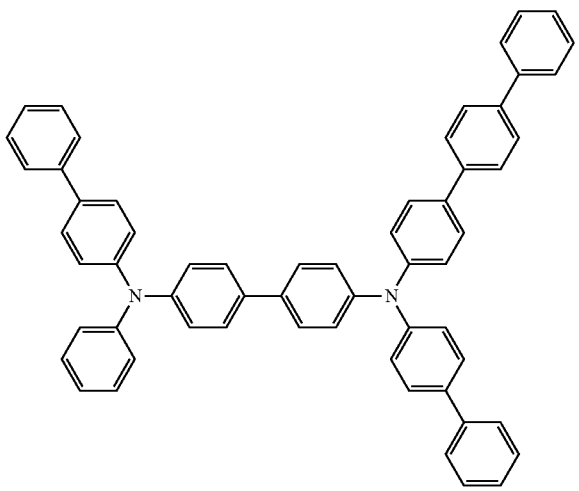

(HTL-4)

(HTL-5)
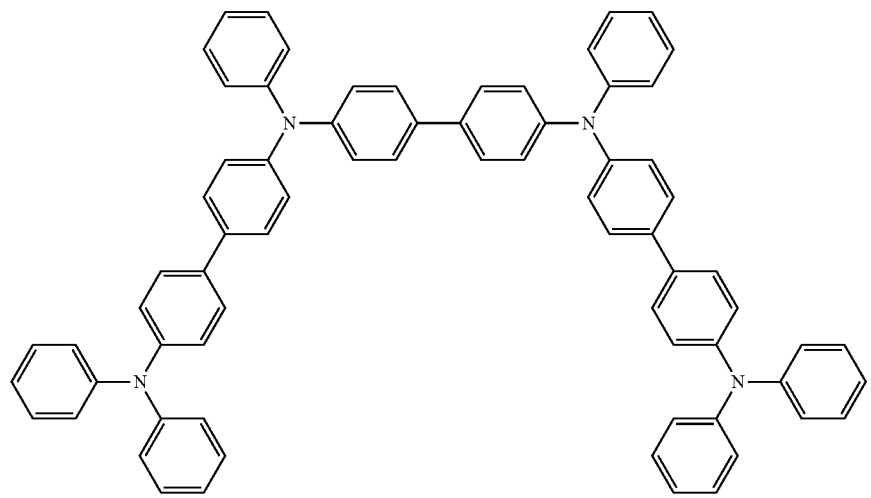
(HTL-6)　　　　　　　　　　(HTL-7)
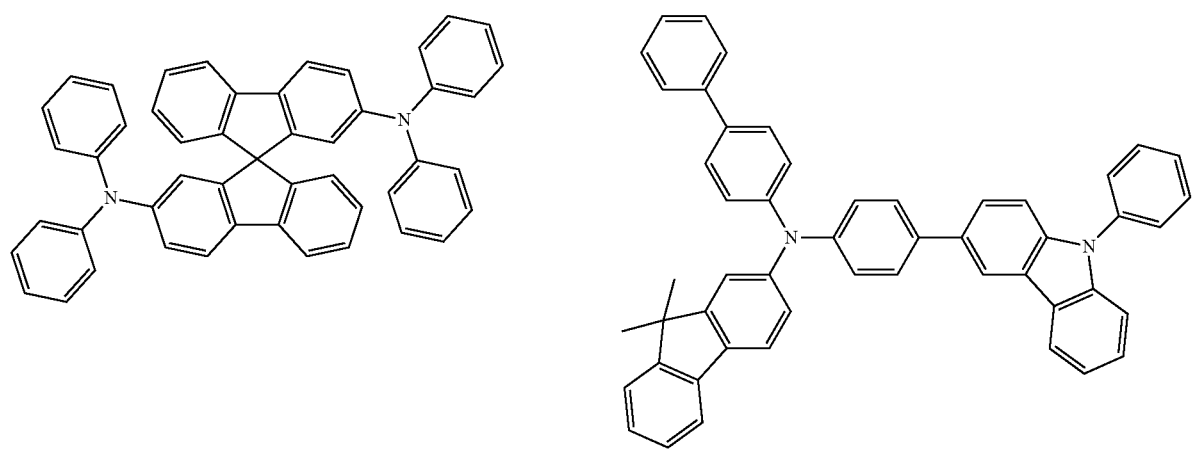
(HTL-8)
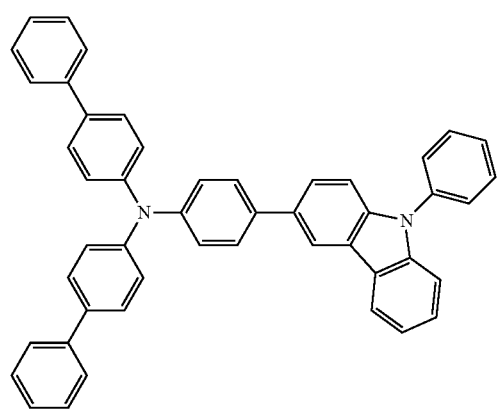

-continued (HTL-9) (HTL-10)

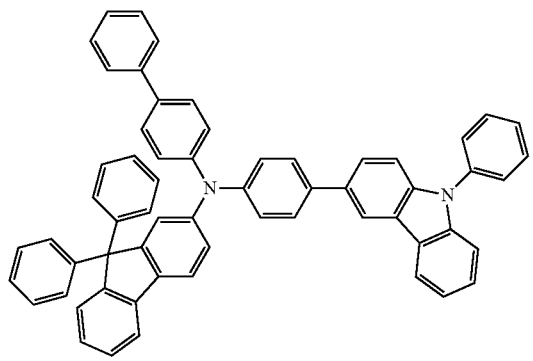
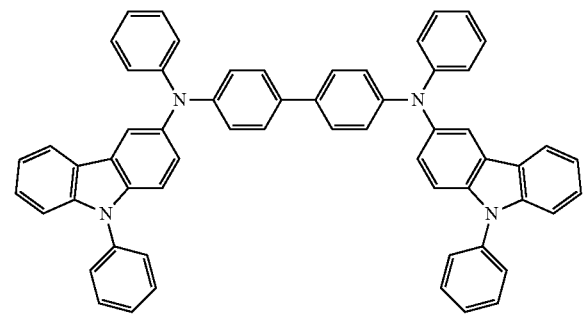

(HTL-11) (HTL-12)

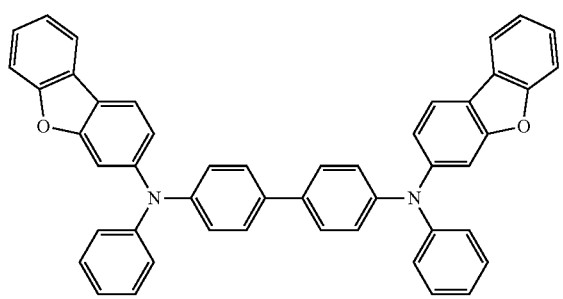
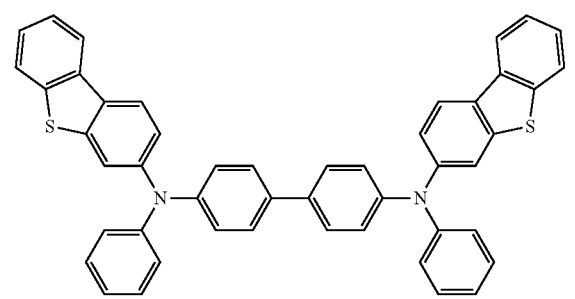

(HTL-13) (HTL-14)

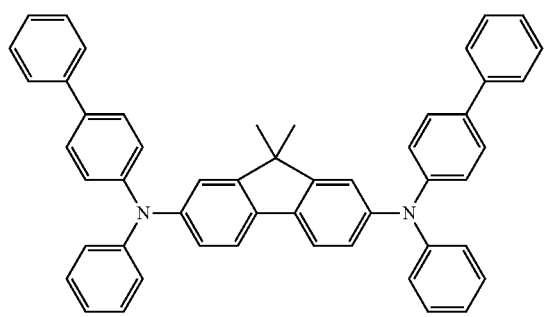
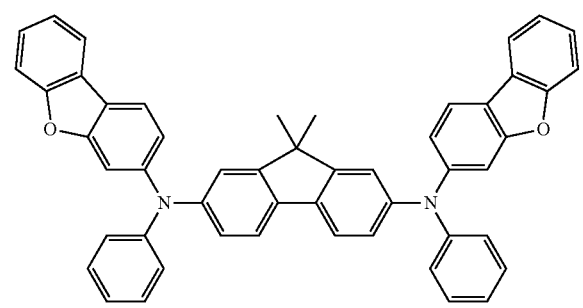

[Compound Represented by General Formula (O-1)]

The light emitting element of the present invention preferably includes at least one organic layer between the light emitting layer and the cathode, and the organic layer preferably contains at least one of compounds represented by the following general formula (O-1), from the viewpoint of the efficiency or driving voltage of an element. Hereinbelow, the general formula (O-1) will be described.

[Chem. 37]

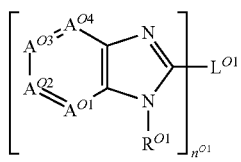

(O-1)

In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6.

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. In the case where the aryl group of $R^{O1}$ has a substituent, examples of the substituent preferably include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ be C—$R^A$; it is more preferable that $A^{O1}$ be a nitrogen atom, and $A^{O2}$ to $A^{O4}$ be C—$R^A$; and it is still more preferable that $A^{O1}$ be a nitrogen atom, $A^{O2}$ to $A^{O4}$ be C—$R^A$, and $R^A$'s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents any of a divalent to hexavalent linking group with an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 38]

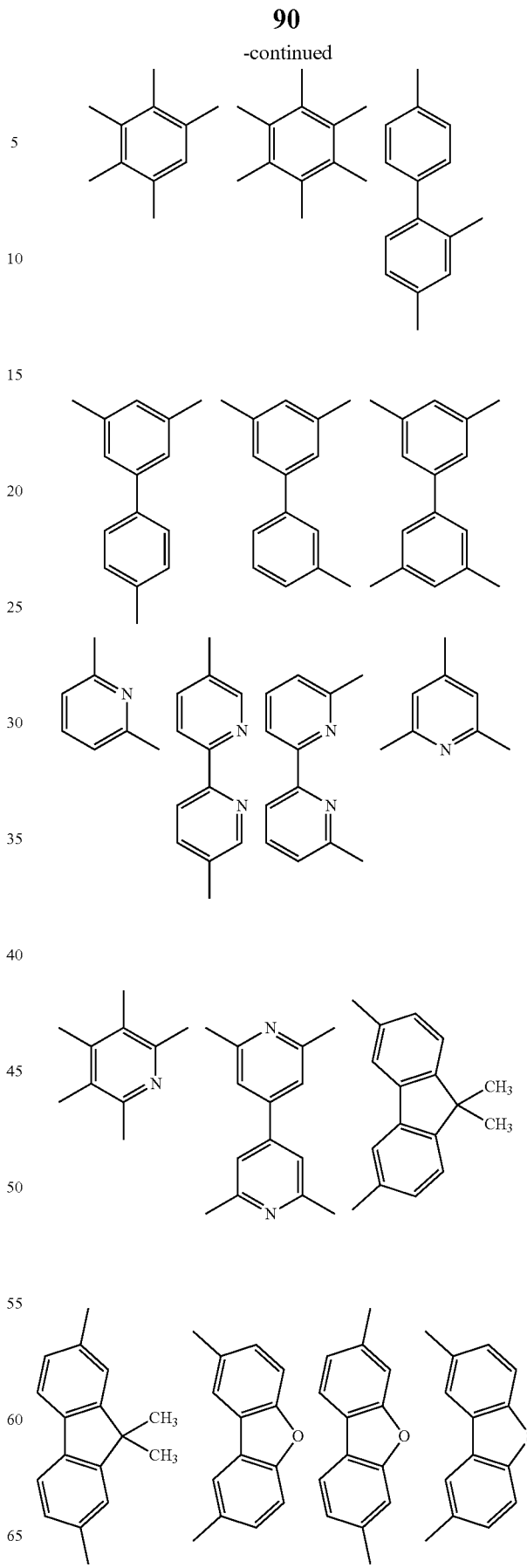

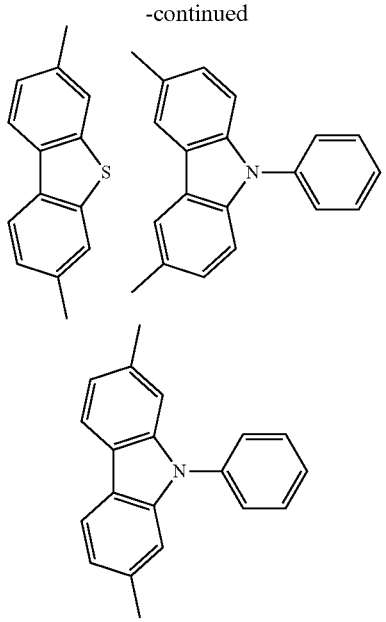

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The compound represented by the general formula (O-1) is more preferably a compound represented by the following general formula (O-2).

[Chem. 39]

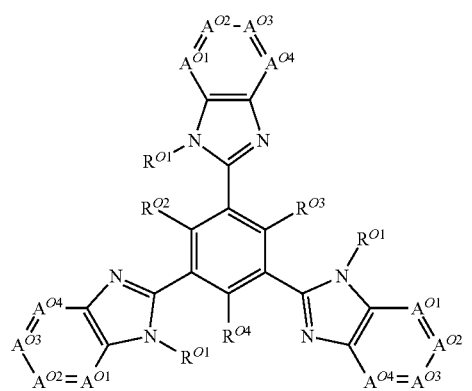

(O-2)

In the general formula (O-2), $R^{O1}$ represents an alkyl group, an aryl group, or a heteroaryl group. $R^{O2}$ to $R^{O4}$ each independently represent a hydrogen atom, an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^{O1}$'s, $A^{O1}$'s to $A^{O4}$'s, and $R^A$'s may be the same as or different from each other.

$R^{O1}$ and $A^{O1}$ to $A^{O4}$ have the same meaning as $R^{O1}$ and $A^{O1}$ to $A^{O4}$ in the general formula (O-1), and their preferred ranges are also the same.

$R^{O2}$ to $R^{O4}$ each independently represent a hydrogen atom, an alkyl group (preferably having 1 to 8 carbon atoms), an aryl group (preferably having 6 to 30 carbon atoms), or a heteroaryl group (preferably having 4 to 12 carbon atoms), and these may have a substituent selected from the Substituent Group A as described above. $R^{O2}$ to $R^{O4}$ are preferably each a hydrogen atom, an alkyl group, or an aryl group, more preferably a hydrogen atom or an aryl group, and most preferably a hydrogen atom.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but are not limited thereto. In the following structural formulae, Ph represents a phenyl group.

[Chem. 40]

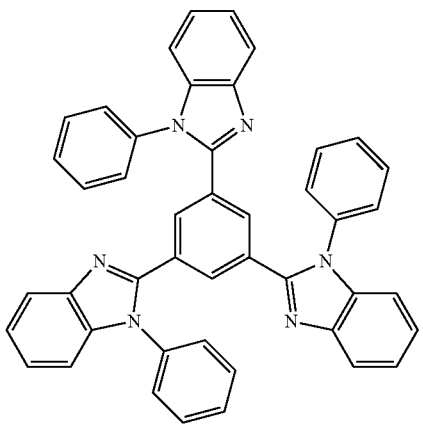

OM-1

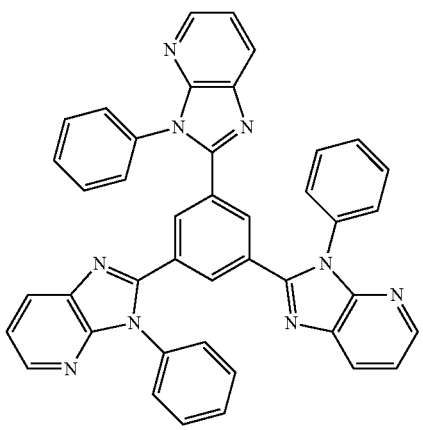

OM-2

OM-3
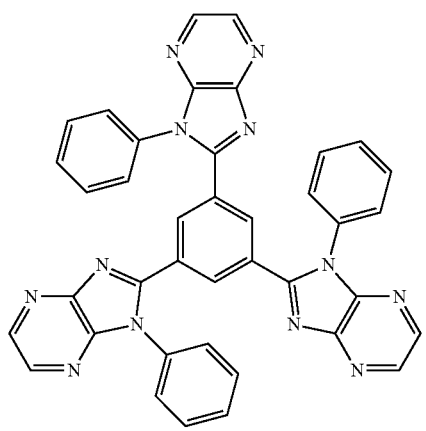
OM-6
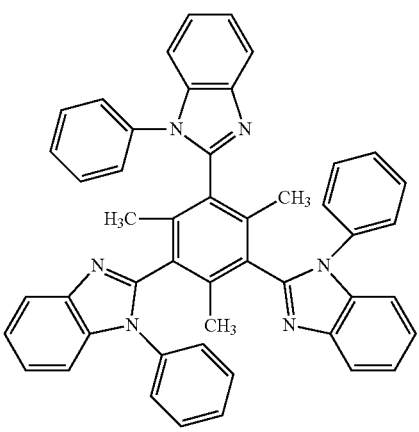
OM-4
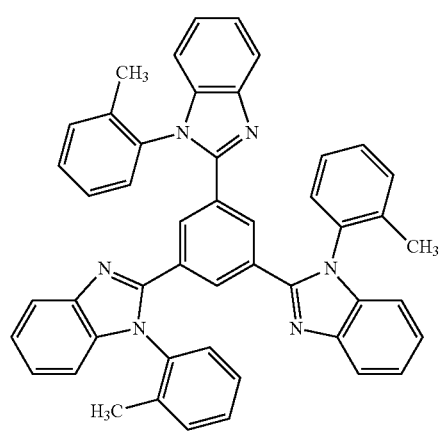
OM-7
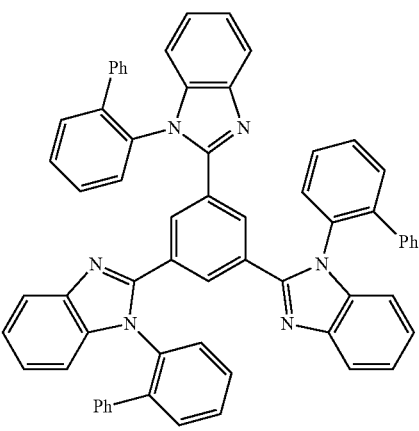
OM-5
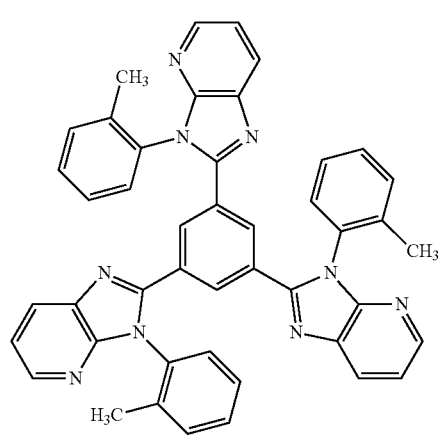
OM-8
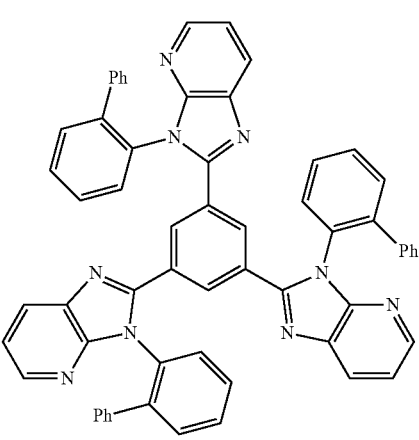

OM-9
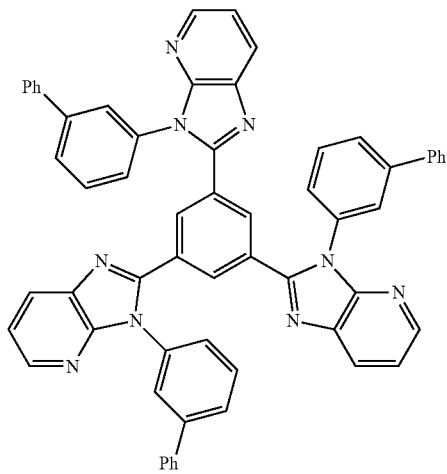
[Chem. 41]
OM-10
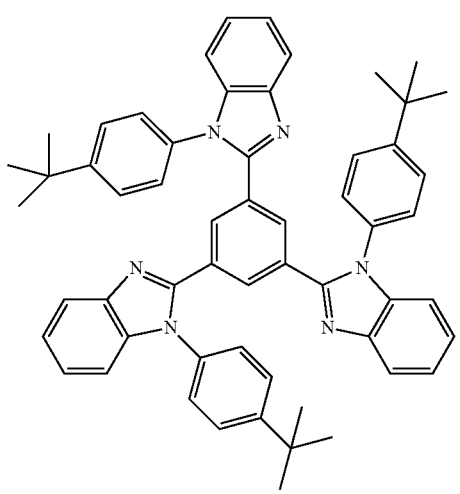
OM-11
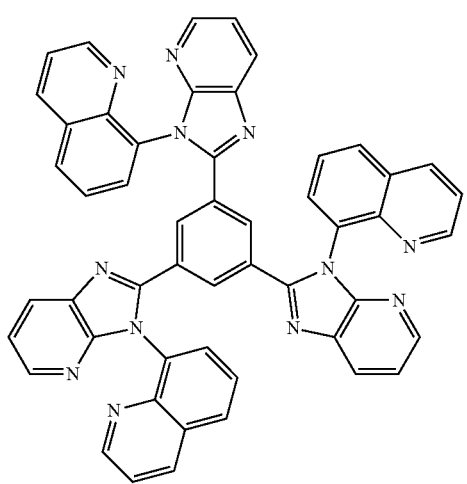
OM-12
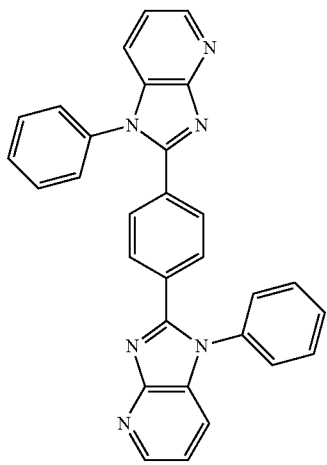
OM-13
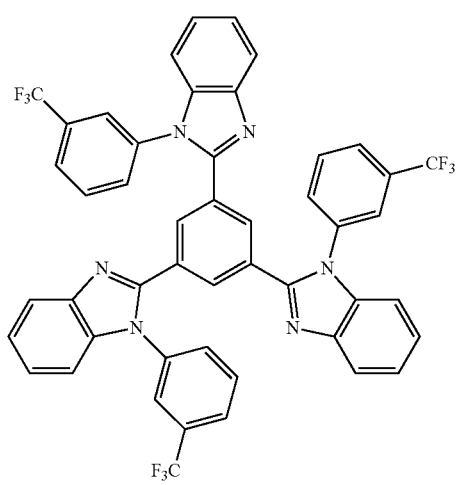
OM-14
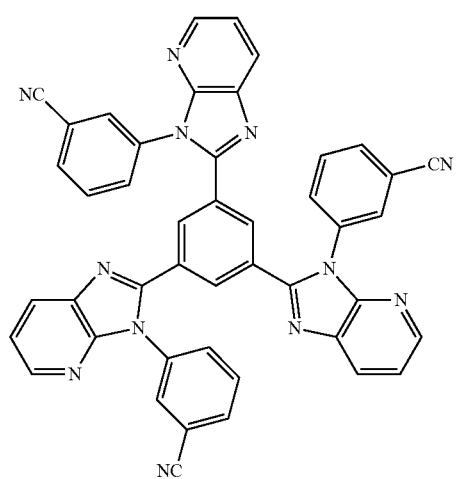

-continued

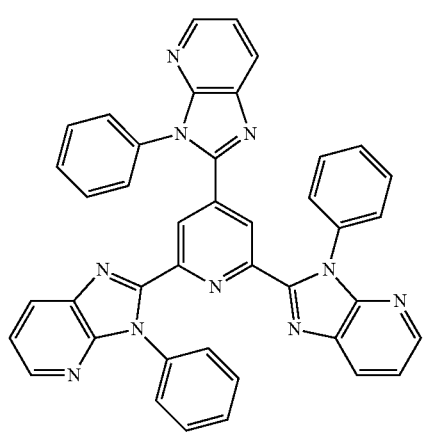

OM-15

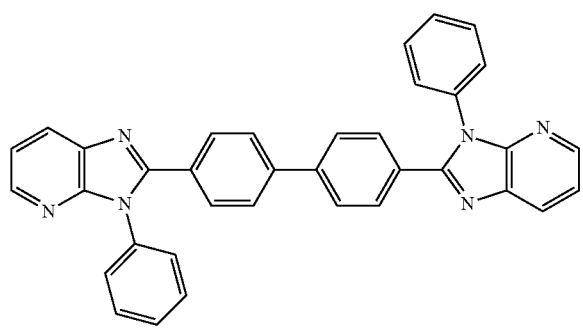

OM-16

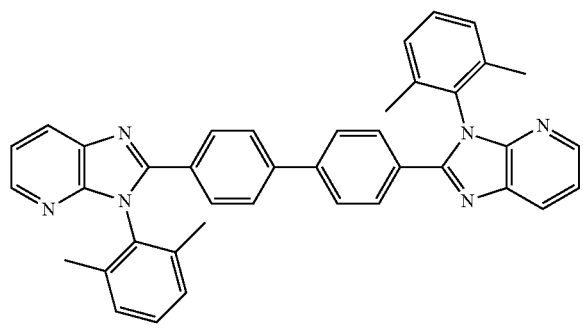

OM-17

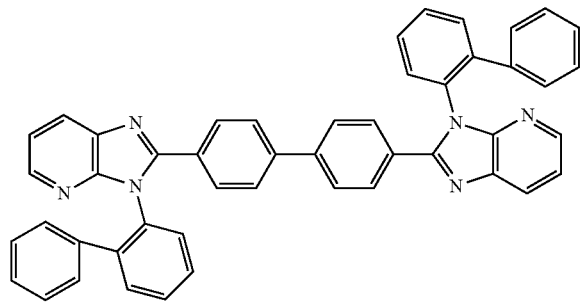

OM-18

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70% by mass to 100% by mass, and more preferably 85% by mass to 100% by mass, with respect to the total mass of the organic layer added.

(Protective Layer)

In the present invention, the entirety of the organic EL element may be protected by a protective layer.

For the protective layer, the detailed description in paragraph Nos. [0169] to [0170] of JP-A-2008-270736 can also be applied to the present invention.

(Sealing Enclosure)

For the element according to the present invention, the entirety of the element may be sealed using a sealing enclosure.

For the sealing enclosure, the detailed description in paragraph No. [0171] of JP-A-2008-270736 can be applied to the present invention.

(Driving)

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 7% or more, and more preferably 10% or more. As to the numerical value of the external quantum efficiency, a maximum value of the external quantum efficiency obtained when the element is driven at 20° C., or a value of the external quantum efficiency in the vicinity of 300 cd/m$^2$ to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Use of Element of the Present Invention>

The element of the present invention can be suitably used for display elements, displays, backlights, electrophotography, illumination light sources, recording light sources, exposure light sources, readout light sources, signs, billboards, interior decorations, optical communications, and the like, in particular, devices driven in a region of high-intensity luminescence, such as an illumination device and a display device.

(Light Emitting Device)

Next, the light emitting device of the present invention will be described with reference to FIG. 2.

The light emitting device of the present invention is formed by using the organic electroluminescent element.

Figure 2:
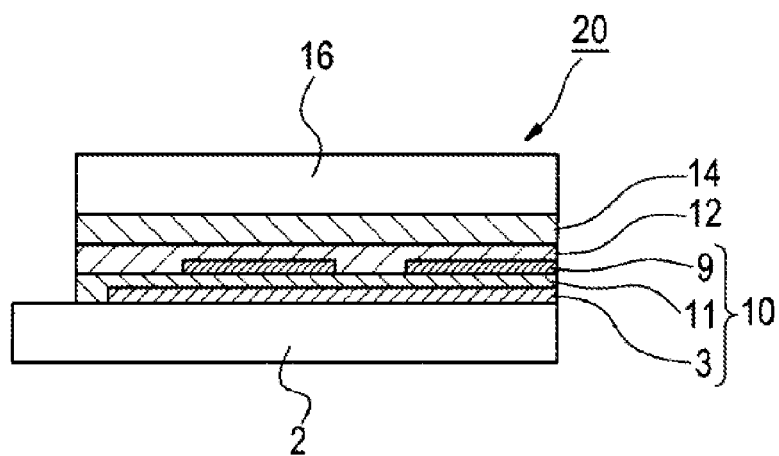
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate (supporting substrate) 2, an organic electroluminescent element 10, a sealing enclosure 16, and the like.

The organic electroluminescent element 10 is formed by laminating an anode (first electrode) 3, an organic layer 11, and a cathode (second electrode) 9 in this order on the substrate 2. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted.

Here, as the adhesive layer 14, a photocurable adhesive such as an epoxy resin, or a thermosetting adhesive can be used, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

(Illumination Device)

Next, the illumination device of the present invention will be described with reference to FIG. 3.

Figure 3:
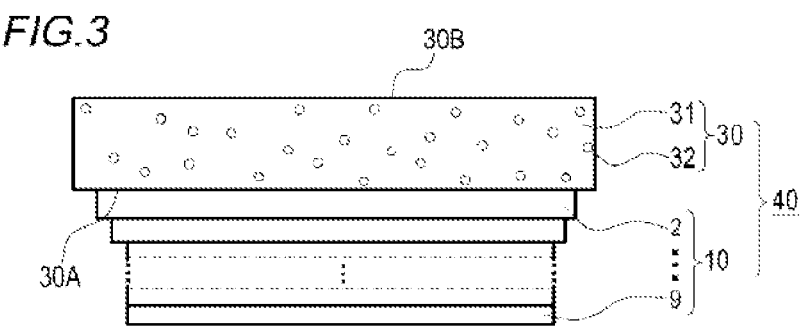
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the light scattering member 30, the incident light is scattered by the light scattering member 30 and the scattered light is output as illuminating light from the light outputting surface 30B.

EXAMPLES

Hereinbelow, the present invention will be described in more detail with reference to Examples, but the present invention is not limited thereto.

1. Synthesis Example (Compound (1-7))

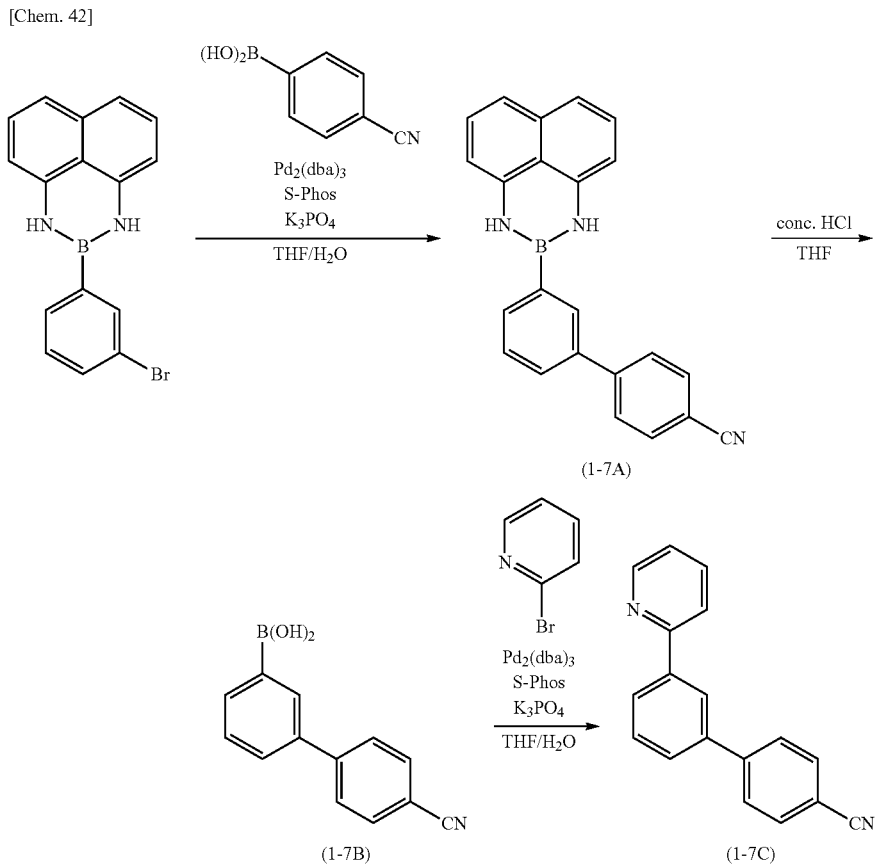

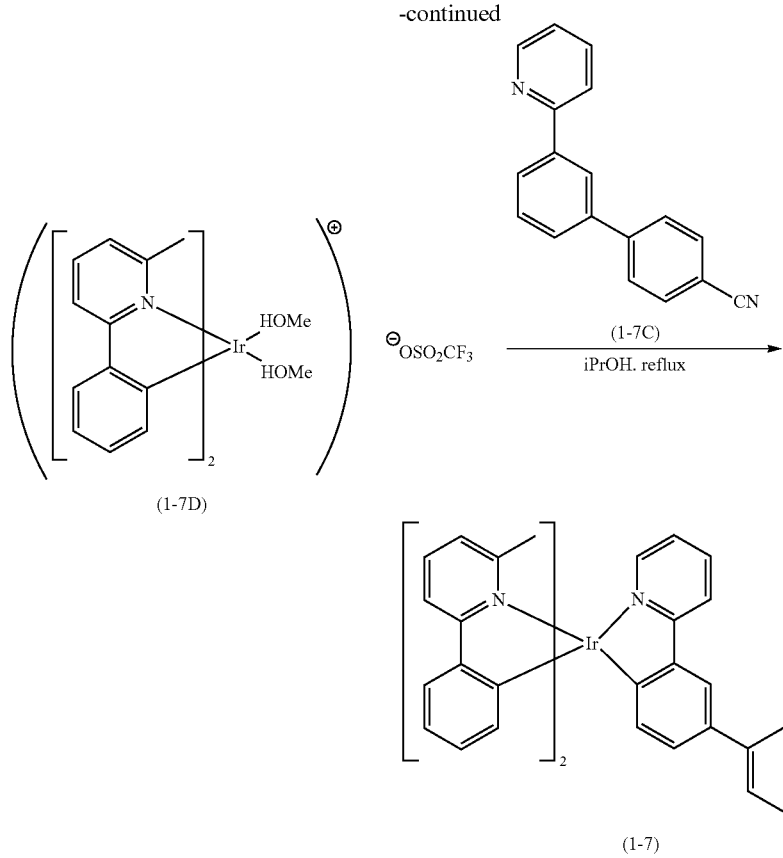

Synthesis of Compound (1-7A)

15 g of m-bromobenzeneboronic acid 1,8-diaminonaphthalene as a protective group, 29.6 g of potassium triphosphate, 3.8 g of 2-dicyclohexylphosphino-2',6'-dimethoxybiphenyl (S-phos), 75 ml of tetrahydrofuran (THF), and 75 ml of distilled water were put into a 500-ml 3-neck flask, and the mixture was stirred, degassed, and then purged with nitrogen. Under a nitrogen gas flow, 2.1 g of tris(dibenzylideneacetone) dipalladium (Pd$_2$(dba)$_3$) and 13.6 g of 4-cyanophenylboronic acid were added thereto, and the mixture was heated and refluxed in an oil bath at 80° C. for 5 hours. After returning to room temperature, 100 ml of toluene was added thereto, THF was evaporated under reduced pressure, and then the aqueous layer was removed. The organic layer was purified by column chromatography using a toluene/hexane eluent to obtain 9 g of a compound (1-7A).

Synthesis of Compound (1-7B)

9 g of the compound (1-7A), 90 ml of THF, and 9 ml of hydrochloric acid were put into a 3-neck flask, and the mixture was stirred at room temperature for 5 hours. The obtained precipitate was separated by filtration and the filtrate was washed with an aqueous hydrochloric acid solution 2 times. The residue was extracted with ethyl acetate and dried under reduced pressure to obtain 4.5 g of (1-7B).

Synthesis of Compound (1-7C)

3.2 g of 2-bromopyridine, 12.8 g of potassium triphosphate, 1.66 g of S-phos, 30 ml of THF, and 30 ml of distilled water were put into a 3-neck flask, and the mixture was stirred, degassed, and then purged with nitrogen. Under a nitrogen gas flow, 0.9 g of Pd$_2$ (dba)$_3$ and 4.5 g of the compound (1-7B) were added thereto, and the mixture was heated and refluxed in an oil bath at 80° C. for 5 hours. After returning to room temperature, 100 ml of toluene was added thereto, THF was evaporated under reduced pressure, and then the aqueous layer was removed. The organic layer was purified by column chromatography using a toluene/hexane eluent to obtain 3 g of a compound (1-7C).

Synthesis of Compound (1-7)

Figure 4:
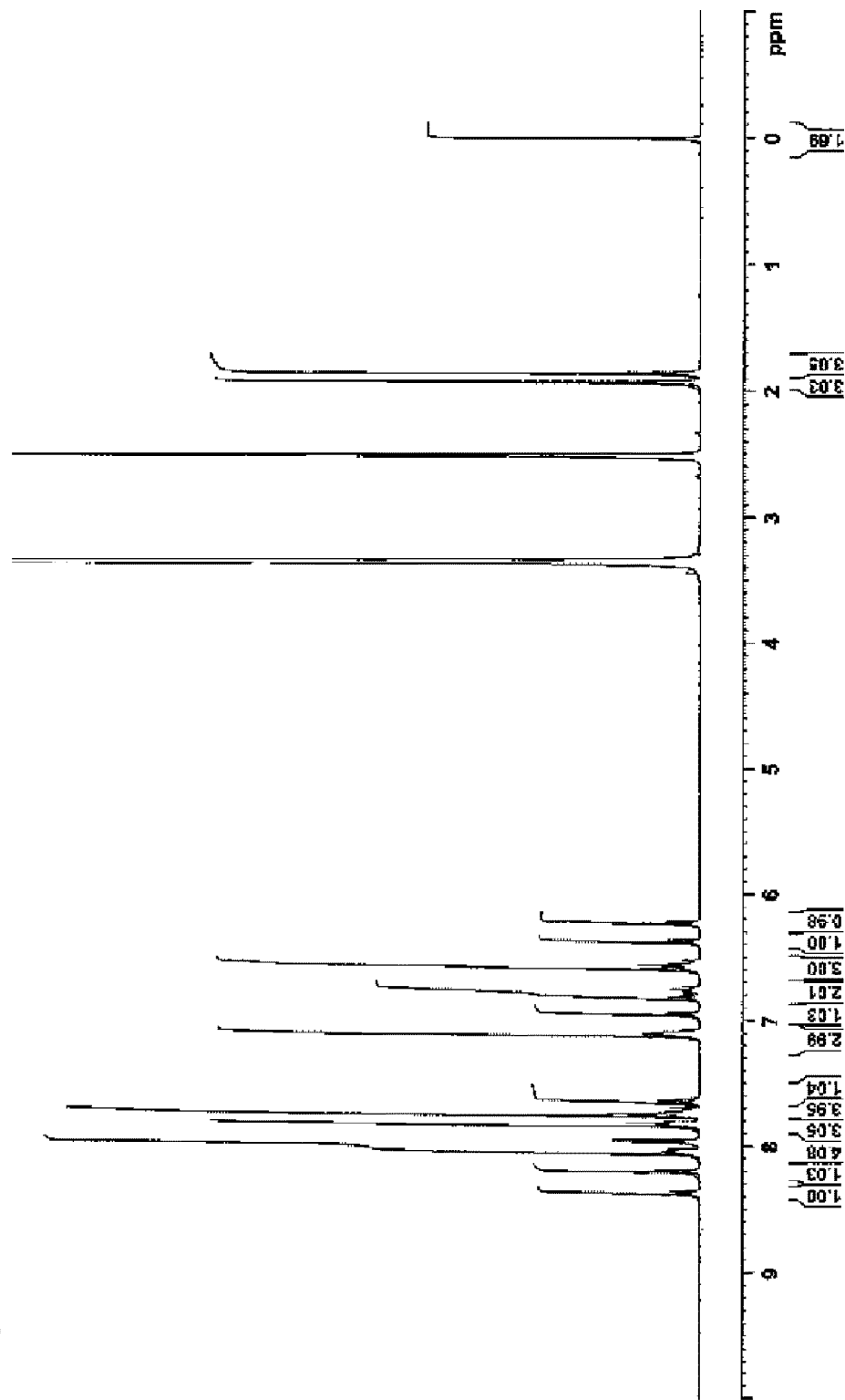
FIG. 4 is a view showing $^1$H-NMR data of the compound (1-7).

1.5 g of the compound (1-7D) and 30 ml of isopropanol were put into a 100-ml 3-neck flask. Under a nitrogen gas flow, 0.4 g of the compound (1-7C) was added thereto and the mixture was heated and refluxed in an oil bath at 95° C. for 16 hours. After returning to room temperature, the precipitate was filtered and washed with isopropanol. The filtrate was dissolved in 12 ml of chloroform and the solution was purified by silica gel column chromatography using a chloroform/hexane eluent. The solvent was evaporated, the residue was dissolved in dichloromethane, ethanol was then added thereto, and dichloromethane was evaporated in a rotary evaporator. The obtained precipitate was separated by filtration, washed with ethanol, and dried in vacuo to obtain 0.45 g of a yellow solid. The obtained yellow solid was purified by sublimation purification. Sublimation purification was carried out using TRS-1 manufactured by ULVAC-RIKO, Inc. The pressure was reduced to approximately $9.85 \times 10^{-3}$ Pa and adjusted to $8.12 \times 10^{-1}$ Pa under an argon gas flow, and then the temperature was raised to 300° C. to carry out sublimation purification. The crystals attached to a glass tube were collected using a spatula to obtain 0.33 g of a compound (1-7). The $^1$H-NMR data of the synthesized compound (1-7) are shown in FIG. 4.

Synthesis Scheme of Compound (1-5)
[Chem. 43]
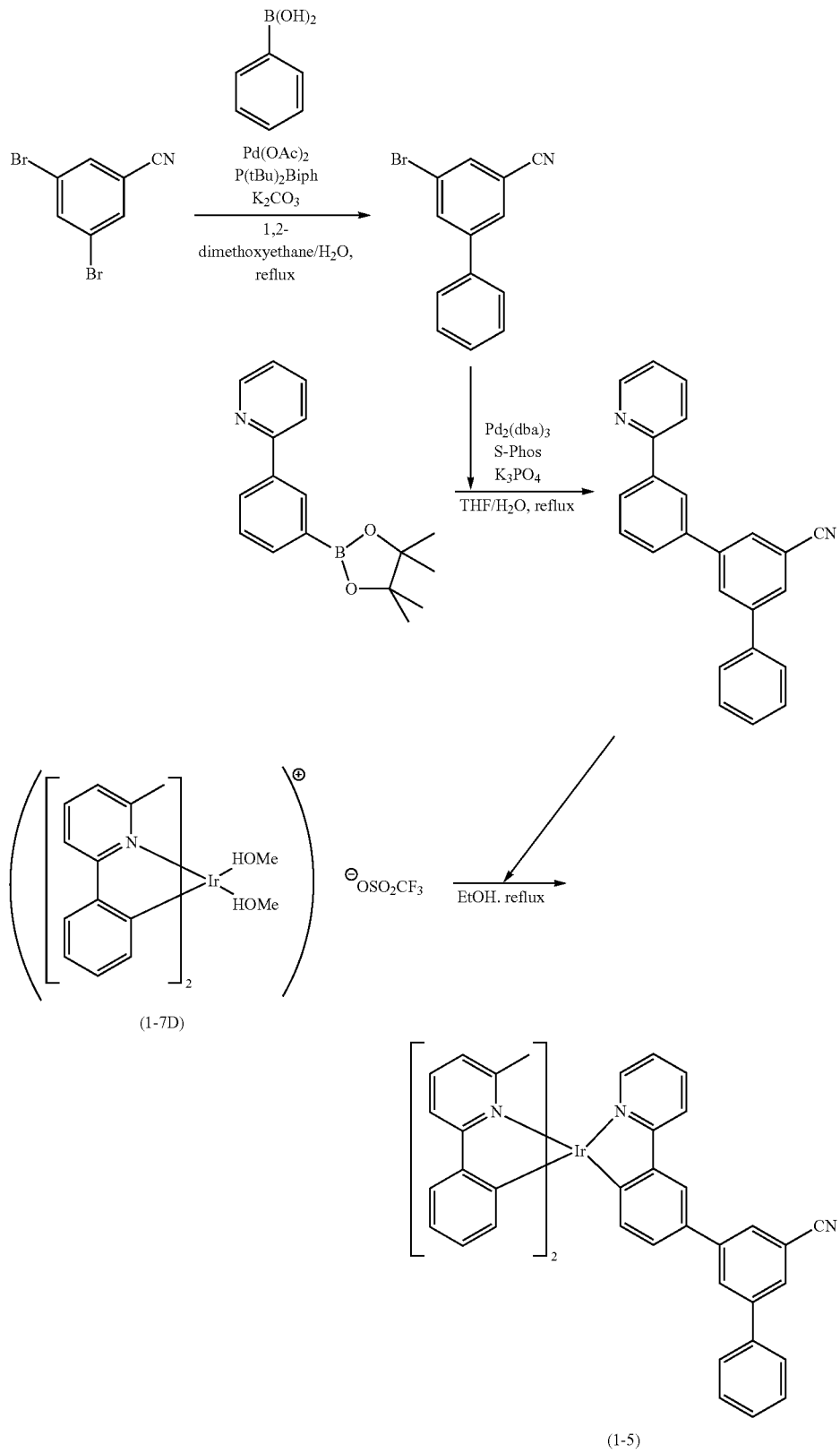

Synthesis Scheme of Compound (2-12)
[Chem. 44]
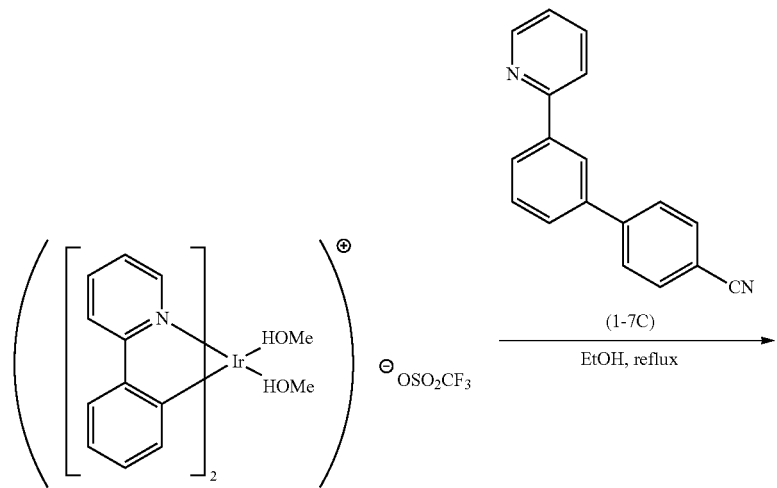
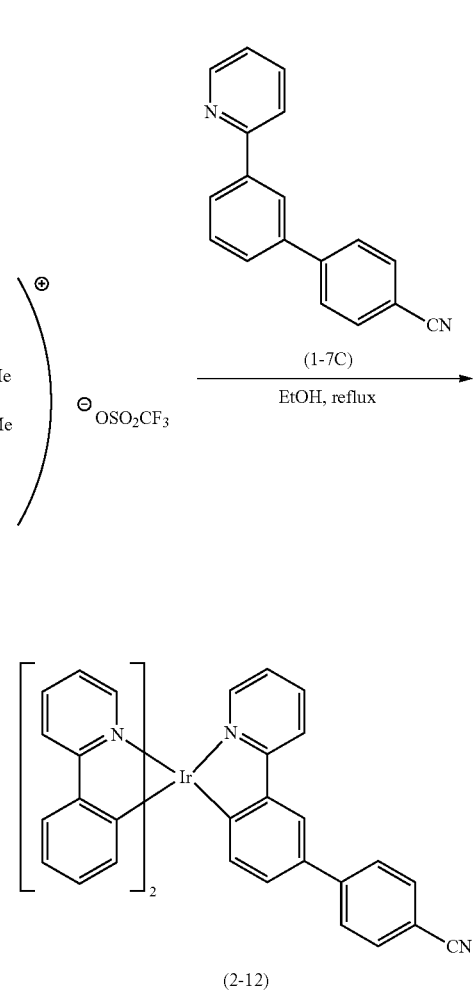
Synthesis Scheme of Compound (3-5)
[Chem. 45]
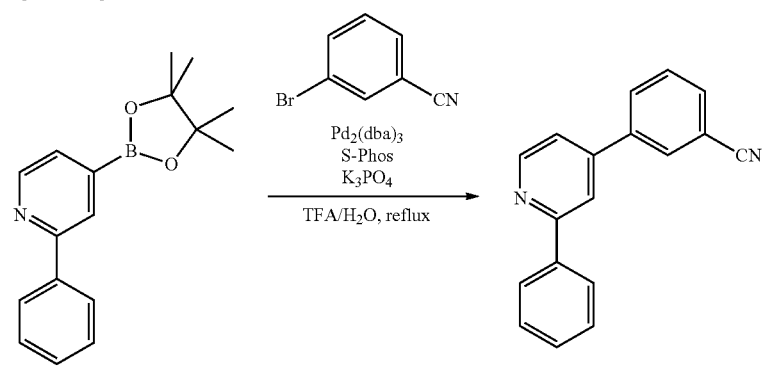

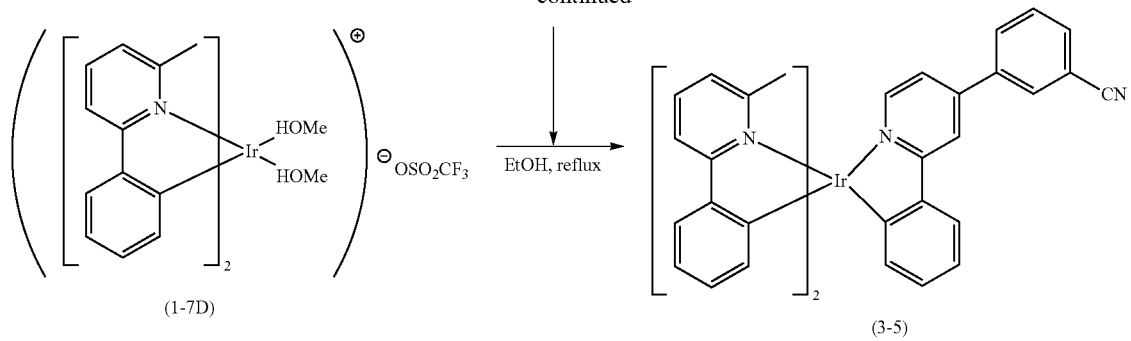
Synthesis Scheme of Compound (6-8)
[Chem. 46]
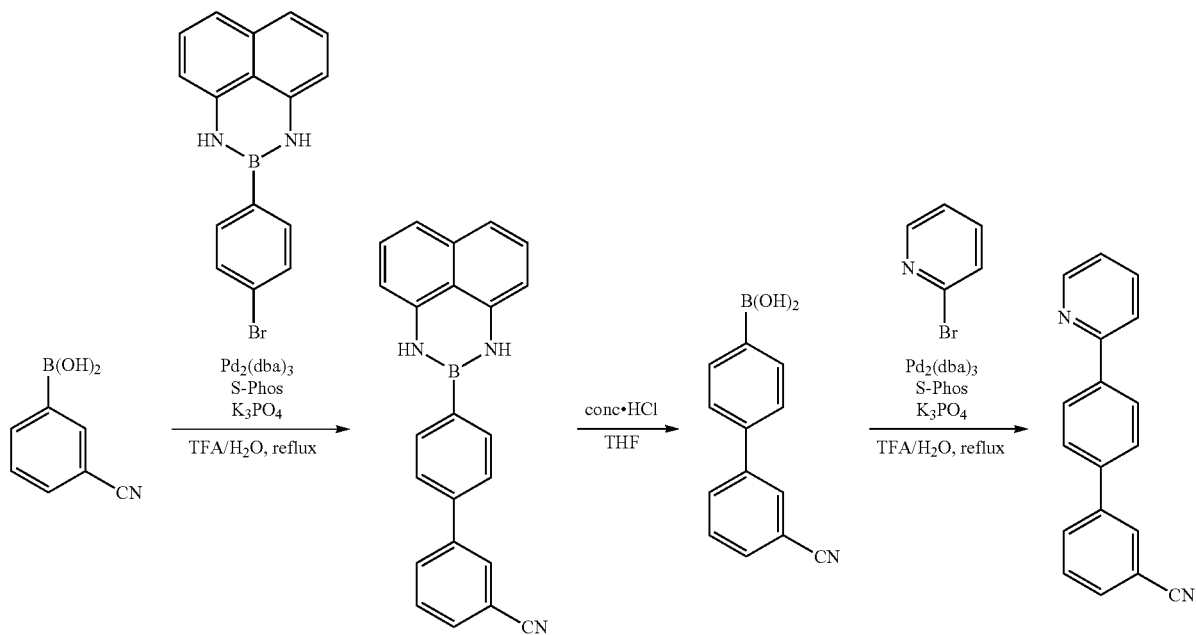
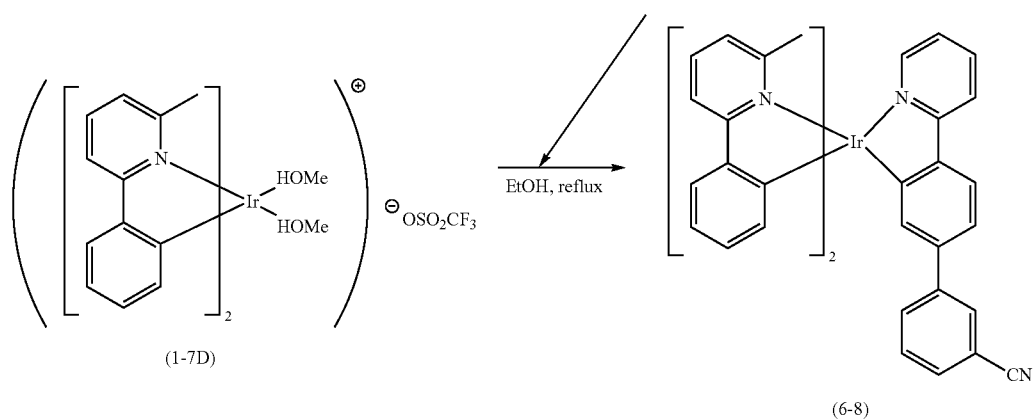

Synthesis Scheme of Compound (7-1)
[Chem. 47]
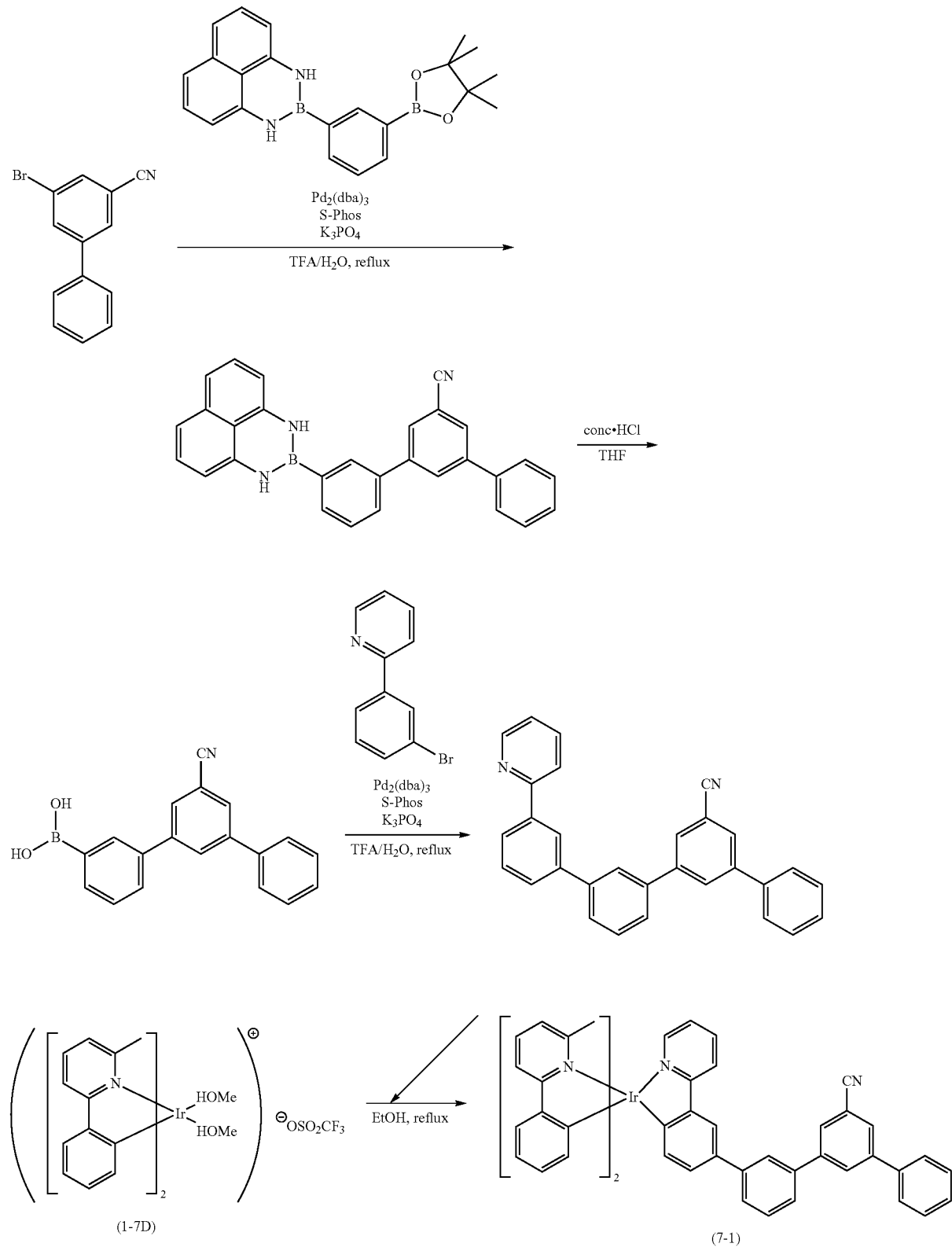

The other compounds can be synthesized according to the following scheme in the same manner as for the compound (1-7).

[Chem. 48]

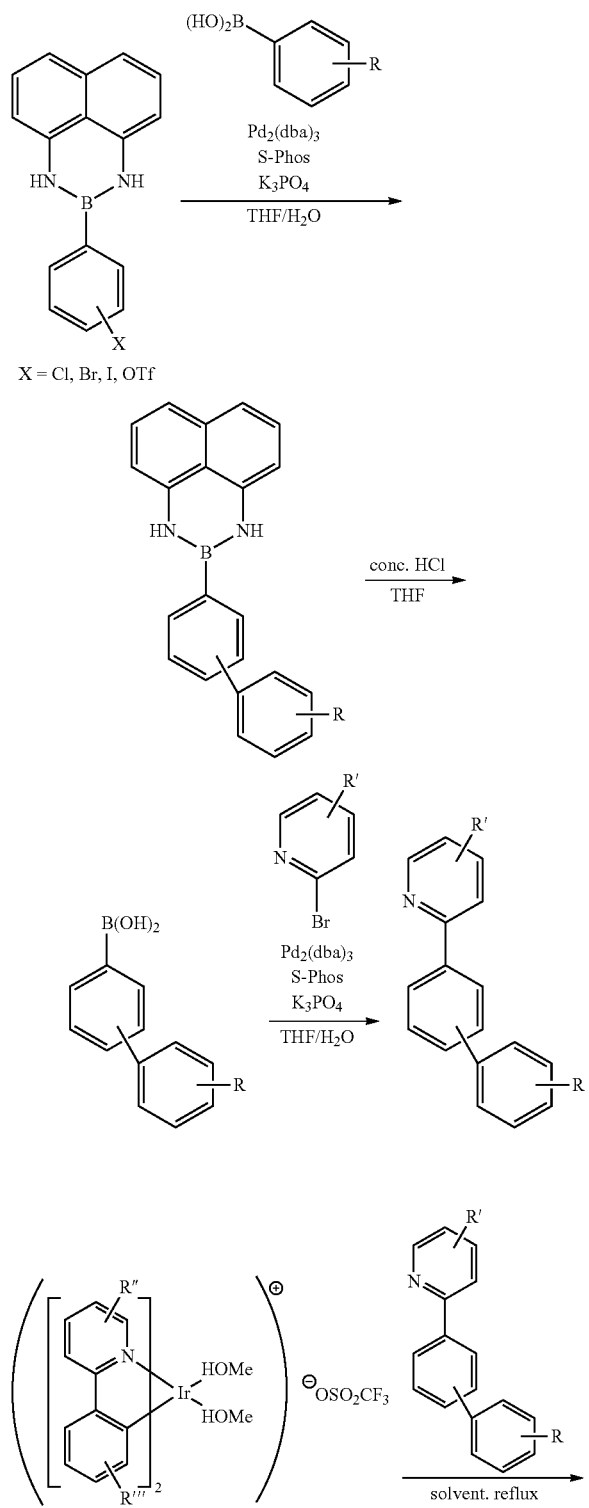

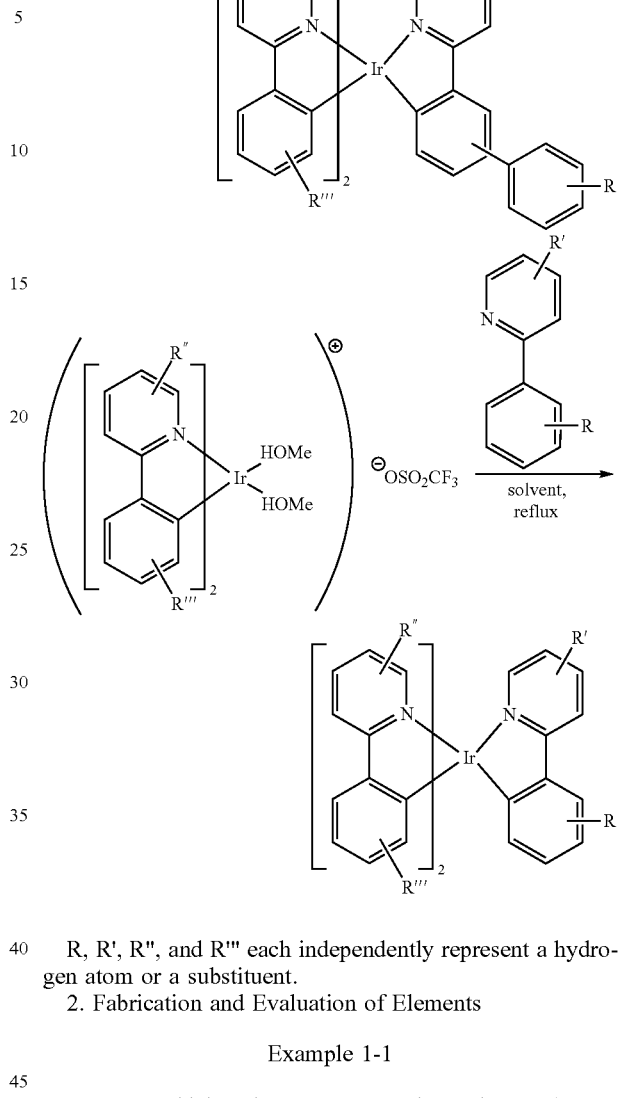

R, R', R", and R'" each independently represent a hydrogen atom or a substituent.

2. Fabrication and Evaluation of Elements

Example 1-1

A 0.5 mm-thick and 2.5 cm square glass substrate (manufactured by Geomatec Co., Ltd., surface resistance: 10Ω/☐ (Ω/square)) having an ITO film thereon was put in a cleaning container. After ultrasonic cleaning in 2-propanol, the glass substrate was subjected to a UV-ozone treatment for 30 minutes. The following organic layers were deposited sequentially on this transparent anode (ITO film) by a vacuum deposition method.

First layer (charge generating layer): Compound (A): Film thickness 10 nm

Second layer (hole transporting layer): HTL-1: Film thickness 30 nm

Third layer (light emitting layer): H-1 (host compound) and Compound (1-7) (light emitting material) (mass ratio of host compound:light emitting material=85:15): Film thickness 40 nm Fourth layer (electron transporting layer): ETL-1: Film thickness 40 nm 1 nm of lithium fluoride and 100 nm of metallic aluminum were deposited in this order thereon to form a cathode.

This laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba Ltd.) to obtain an element of Example 1.

Examples 1-2 to 1-10 and Comparative Examples 1-1 to 1-5

In the same manner as in Example 1-1 except that the compound (1-7) of the third layer was replaced by a compound shown in Table 1 below in the fabrication of the element of Example 1-1, elements of Examples 1-2 to 1-10 and Comparative Examples 1-1 to 1-5 were fabricated.

These elements were evaluated in terms of efficiency, durability, and driving voltage by the following methods, and the results are shown in Table 1 below.

(Driving Voltage)

Light was emitted by applying a direct current voltage to each element to give a luminance of 3500 cd/m$^2$. The voltage applied at that time was taken as an index for evaluation of a driving voltage. A case where the driving voltage is less than 5.5 V was taken as A, a case where the driving voltage is 5.5 V or more and less than 7 V was taken as B, a case where the driving voltage is 7 V or more was taken as C, and the results are shown in Table 1 below.

(External Quantum Efficiency)

Light was emitted by applying a direct current voltage to each of the elements using a source measure unit 2400 manufactured by TOYO Corporation. The luminance was measured using a luminance meter BM-8 manufactured by Topcon Corporation. The luminous spectrum and the light emitting peak wavelength were measured using a spectrum analyzer PMA-11 manufactured by Hamamatsu Photonics K. K. Based on these values, the external quantum efficiency at a luminance in the vicinity of 3500 cd/m$^2$ was calculated by using a luminance conversion method.

A case where the external quantum efficiency is 15% or more was taken as A, a case where the external quantum efficiency is 10% or more and less than 15% was taken as B, a case where the external quantum efficiency is less than 10% was taken as C, and the results are shown in Table 1 below.

(Durability)

Light was continuously emitted by applying a direct current voltage to each of the elements to give a luminance of 3500 cd/m$^2$ at room temperature (20° C.), and the time taken until the luminance became 3395 cd/m$^2$ was taken as an index for durability. How many times the durability time is taken until the luminance became 3395 cd/m$^2$ is than the durability time for the element in which the light emitting material was replaced by a comparative compound (E-1) (Comparative Example 1-1) was calculated, and shown in Table 1 below. A indicates 2 times or more, B indicates 1.5 times or more and less than 2 times, C indicates 1.1 times or more and less than 1.5 times, D indicates 0.5 times or more and less than 1 time, and E indicates less than 0.5 times.

(Possibility of Sublimation Purification of Light Emitting Material)

Sublimation purification was carried out using TRS-1 manufactured by ULVAC-RIKO, Inc. The pressure was reduced to approximately 7.0×10$^{-2}$ Pa, and the temperature was raised until the sublimation occurred. The crystals attached to a glass tube were collected using a spatula. A case where 10% or more of the weight before the sublimation can be collected was denoted as "possible" and a case where less than 10% of the weight before the sublimation can be collected was denoted as "impossible". The results are shown in Table 1.

Examples 2-1 to 6-7 and Comparative Examples 2-1 to 6-1

In the same manner as for the fabrication of the element of Example 1-1 except that the materials of the hole transporting layer, the light emitting materials, and the host compounds were changed as shown in Tables 2 to 6 below, the elements of Examples 2-1 to 6-7 and Comparative Examples 2-1 to 6-1 were fabricated and evaluated in the same manner as in Example 1-1. Further, as for the durability time, how many times the durability time was than the bases (1.0), which are Comparative Example 2-1 in Table 2, Comparative Example 3-1 in Table 3, Comparative Example 4-1 in Table 4, Comparative Example 5-1 in Table 5, and Comparative Example 6-1 in Table 6, respectively, are shown.

TABLE 1

| | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 1-1 | HTL-1 | (1-7) | H-1 | Possible | B | B | A |
| Example 1-2 | HTL-1 | (1-3) | H-1 | Possible | B | B | A |
| Example 1-3 | HTL-1 | (1-5) | H-1 | Possible | B | B | B |
| Example 1-4 | HTL-1 | (1-6) | H-1 | Possible | B | B | A |
| Example 1-5 | HTL-1 | (2-3) | H-1 | Possible | B | B | B |
| Example 1-6 | HTL-1 | (2-7) | H-1 | Possible | B | B | B |
| Example 1-7 | HTL-1 | (2-8) | H-1 | Possible | B | B | B |
| Example 1-8 | HTL-1 | (2-12) | H-1 | Possible | B | B | B |
| Example 1-9 | HTL-1 | (3-5) | H-1 | Possible | B | B | B |
| Example 1-10 | HTL-1 | (6-8) | H-1 | Possible | B | B | B |
| Comparative Example 1-1 | HTL-1 | (E-1) | H-1 | Possible | B | B | 1.0 |
| Comparative Example 1-2 | HTL-1 | (E-2) | H-1 | Possible | B | B | E |
| Comparative Example 1-3 | HTL-1 | (E-3) | H-1 | Possible | B | C | E |

TABLE 1-continued

|  | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Comparative Example 1-4 | HTL-1 | (E-4) | H-1 | Possible | B | C | E |
| Comparative Example 1-5 | HTL-1 | (E-5) | H-1 | Impossible | — | — | — |

TABLE 2

|  | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 2-1 | HTL-1 | (1-7) | H-2 | Possible | B | B | C |
| Comparative Example 2-1 | HTL-1 | (E-1) | H-2 | Possible | B | B | 1.0 |

TABLE 3

|  | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 3-1 | HTL-1 | (1-7) | H-3 | Possible | B | B | C |
| Comparative Example 3-1 | HTL-1 | (E-1) | H-3 | Possible | B | B | 1.0 |

TABLE 4

|  | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 4-1 | HTL-1 | (1-7) | H-4 | Possible | A | B | A |
| Example 4-2 | HTL-1 | (2-3) | H-4 | Possible | A | B | B |
| Example 4-3 | HTL-1 | (2-7) | H-4 | Possible | A | B | A |
| Example 4-4 | HTL-1 | (2-8) | H-4 | Possible | A | B | A |
| Example 4-5 | HTL-7 | (2-12) | H-4 | Possible | A | B | A |
| Example 4-6 | HTL-7 | (3-5) | H-4 | Possible | A | B | A |
| Comparative Example 4-1 | HTL-1 | (E-1) | H-4 | Possible | A | B | 1.0 |

TABLE 5

|  | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 5-1 | HTL-1 | (1-7) | H-5 | Possible | B | B | B |
| Comparative Example 5-1 | HTL-1 | (E-1) | H-5 | Possible | B | B | 1.0 |

TABLE 6

| | Hole transporting layer | Light emitting material (third layer) | Host compound | Possibility of sublimation purification of light emitting material | Driving voltage | External quantum efficiency | Durability vs (E-1) (times) |
|---|---|---|---|---|---|---|---|
| Example 6-1 | HTL-1 | (1-7) | H-6 | Possible | A | B | A |
| Example 6-2 | HTL-7 | (2-3) | H-6 | Possible | A | B | A |
| Example 6-3 | HTL-7 | (2-7) | H-6 | Possible | A | B | A |
| Example 6-4 | HTL-7 | (2-8) | H-6 | Possible | A | B | A |
| Example 6-5 | HTL-7 | (2-12) | H-6 | Possible | A | B | A |
| Example 6-6 | HTL-7 | (3-5) | H-6 | Possible | A | B | A |
| Example 6-7 | | (7-1) | H-6 | Possible | A | B | A |
| Comparative Example 6-1 | HTL-1 | (E-1) | H-6 | Possible | A | B | 1.0 |

From Tables 1 to 6 above, it was found that an organic electroluminescent element having excellent efficiency at a low driving voltage and excellent durability is obtained by using the compound represented by the general formula (1) of the present invention as a light emitting material.

Further, it was found that the organic electroluminescent element using the compound represented by the general formula (1) has improved durability in the case of using a host material having a cyano group, and can be driven at a lowered voltage as well.

In addition, the light emitting peak wavelength of the organic electroluminescent elements fabricated in Examples 1-1 to 6-7 was from 500 nm to 550 nm. Further, as seen from Table 1, in Comparative Example 1-5, it was impossible to deposit the light emitting material, and thus, an element could not be fabricated.

In the cases of a light emitting device, a display device, and an illumination device, it is necessary to emit light at a high luminance instantly through a high current intensity at each pixel portion. In this regard, the light emitting element of the present invention is designed to increase the luminous efficiency in such a case, and accordingly, it can be advantageously used.

In addition, the element of the present invention has excellent durability and is thus suitable for a light emitting device, a display device, and an illumination device.

[Chem. 49]

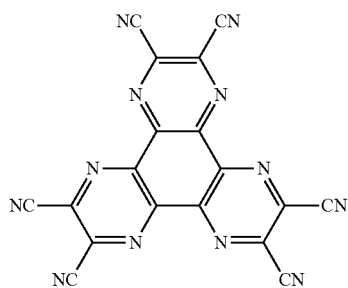

Compound (A)

[Chem. 50]

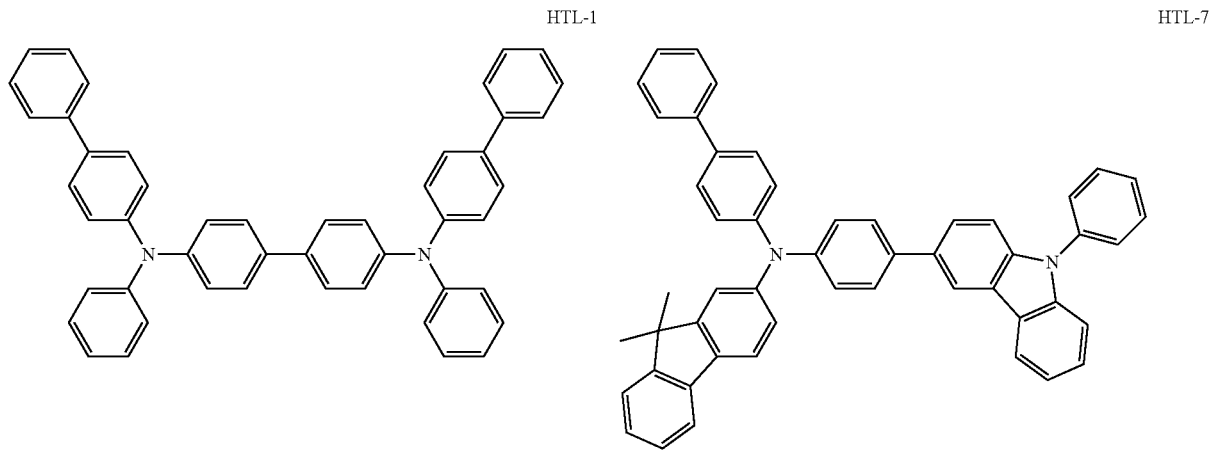

HTL-1          HTL-7

[Chem. 51]
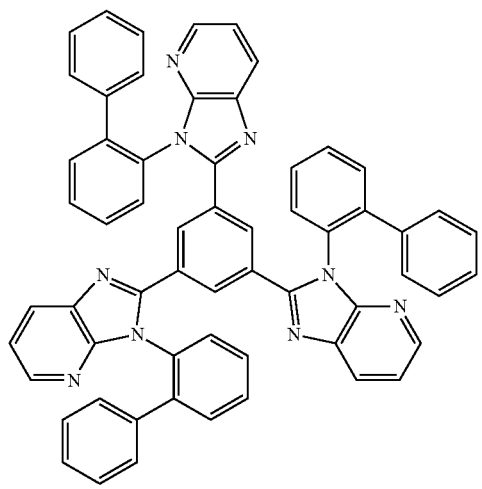
ETL-1
[Chem. 52]
Host compound
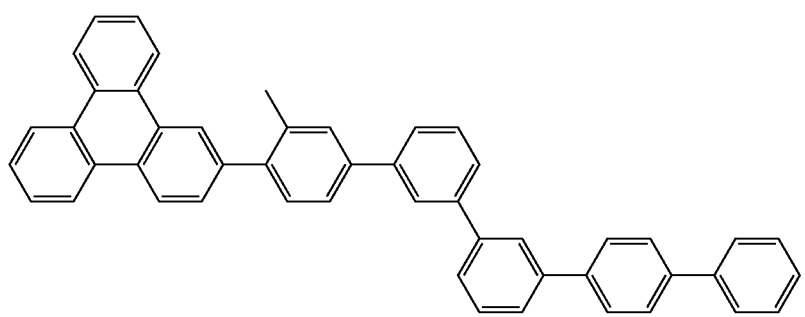
H-1
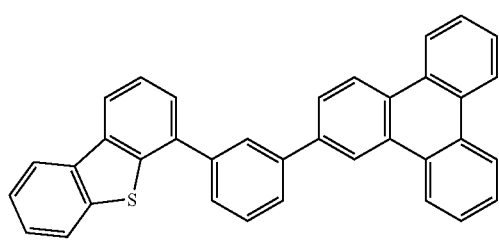
H-2
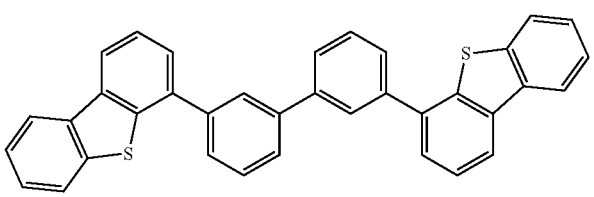
H-3
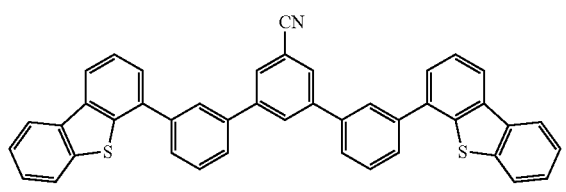
H-4
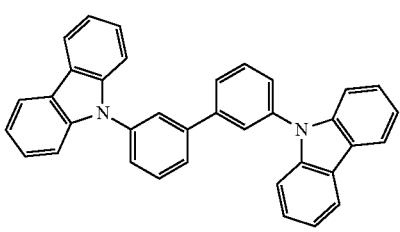
H-5

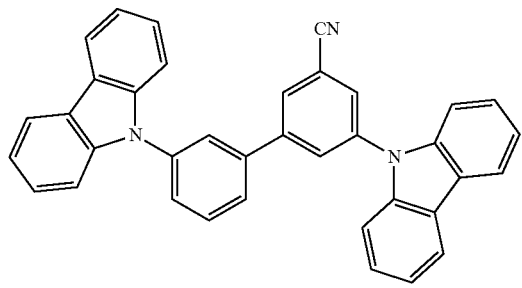

Light Emitting Materials Used in Comparative Examples

[Chem. 53]

E-1

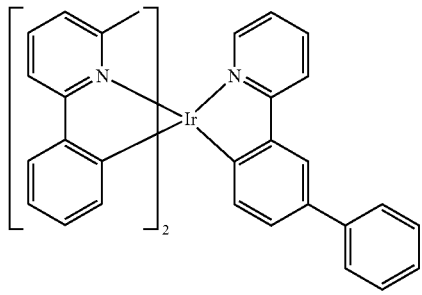

E-2

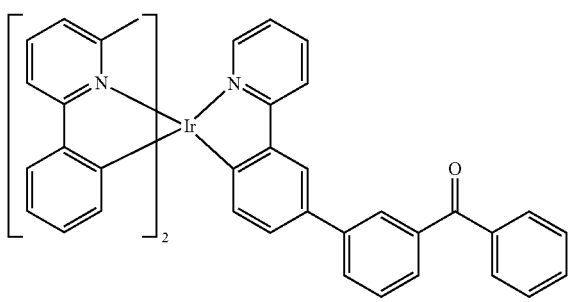

E-3

E-4

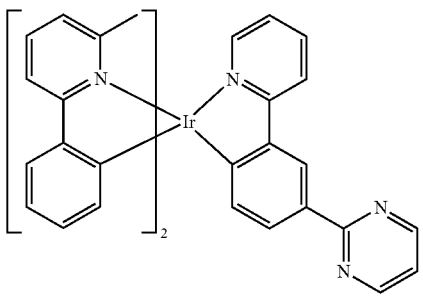

E-5

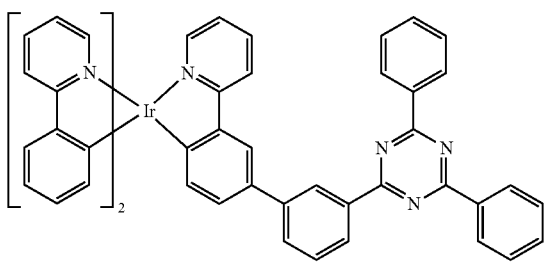

INDUSTRIAL APPLICABILITY

According to the present invention, an organic electroluminescent element having a low driving voltage, excellent efficiency, and excellent durability can be provided. Further, a light emitting device, a display device, and an illumination device each using the organic electroluminescent element can be provided.

In addition, according to the present invention, an iridium complex used for the preparation of the organic electroluminescent element having a low driving voltage, excellent efficiency, and excellent durability can be provided.

The present invention is described above in detail and with reference to specific embodiments, but various changes and modifications will be apparent to persons skilled in the art without departing from the spirit and scope of the present invention.

The present application is based on Japanese Patent Application No. 2011-218507 filed on Sep. 30, 2011, the contents of which are incorporated herein by reference.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT (ORGANIC EL ELEMENT)
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
30A: LIGHT INCIDENT SURFACE
30B: LIGHT OUTPUTTING SURFACE
31: TRANSPARENT SUBSTRATE
32: FINE PARTICLES
40: ILLUMINATION DEVICE

The invention claimed is:

1. An organic electroluminescence device, comprising:
a substrate;
a pair of electrodes including an anode and a cathode, disposed on the substrate; and
at least one organic layer including a light emitting layer, disposed between the electrodes,
wherein at least one kind of compound represented by the following general formula (1) is contained in at least one of the organic layers:

general formula (1)

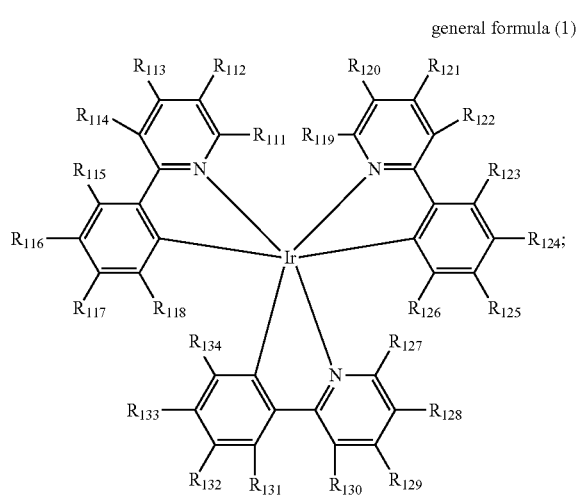

wherein $R_{111}$ to $R_{134}$ each independently represent a hydrogen atom or a substituent; at least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, at least two adjacent groups out of $R_{123}$ to $R_{126}$, at least two adjacent groups out of $R_{127}$ to $R_{130}$, $R_{130}$ and $R_{131}$, or at least two adjacent groups out of $R_{131}$ to $R_{134}$ may be bonded to each other to form a ring, provided that at least one of $R_{119}$ to $R_{134}$ represents a group represented by the following general formula (A); and that none of $R_{111}$ to $R_{118}$ represent a group represented by general formula (A);

General Formula (A)

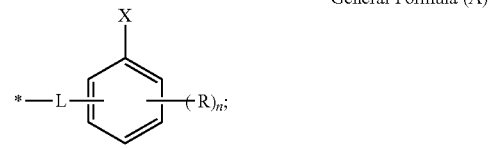

X represents a cyano group or a trifluoromethyl group; L represents a single bond or a divalent linking group; R represents a substituent; when a plurality of R's are present, they may be the same as or different from each other; n represents an integer of 0 to 4; * represents a binding site.

2. The organic electroluminescent element according to claim 1, wherein the compound represented by the general formula (1) is a compound represented by the following general formula (2):

formula (2)

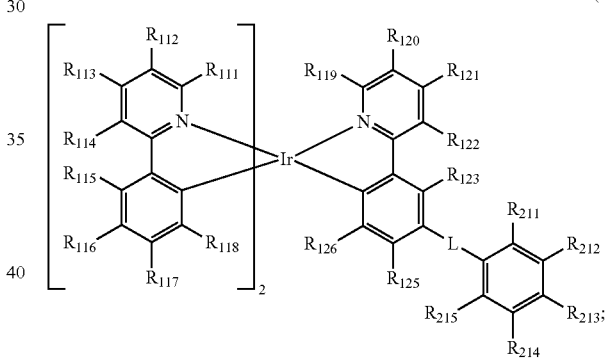

wherein $R_{111}$ to $R_{123}$, $R_{125}$, $R_{126}$, and $R_{211}$ to $R_{215}$ each independently represent a hydrogen atom or a substituent; two groups out of $R_{111}$ to $R_{118}$ may be each the same as or different from each other; at least two adjacent groups out of $R_{111}$ to $R_{114}$, $R_{114}$ and $R_{115}$, at least two adjacent groups out of $R_{115}$ to $R_{118}$, at least two adjacent groups out of $R_{119}$ to $R_{122}$, $R_{122}$ and $R_{123}$, or $R_{125}$ and $R_{126}$, may be bonded to each other to form a ring; L represents a single bond or a divalent linking group, provided that at least one of $R_{211}$ to $R_{215}$ represents a cyano group or a trifluoromethyl group.

3. The organic electroluminescent element according to claim 1, wherein X in the general formula (A) represents a cyano group.

* * * * *